United States Patent [19]
Behan et al.

[11] Patent Number: 6,150,393
[45] Date of Patent: Nov. 21, 2000

[54] SMALL MOLECULE MODULATORS OF NON-ENDOGENOUS, CONSTITUTIVELY ACTIVATED HUMAN SEROTONIN RECEPTORS

[75] Inventors: Dominic P. Behan, San Diego; Derek T. Chalmers, Cardiff; Nigel R. A. Beeley, Solana Beach, all of Calif.; Richard J. Foster, Cornwall, United Kingdom; Robert C. Glen, Glencoe; Michael S. Lawless, St. Charles, both of Mo.; Chen W. Liaw, San Diego, Calif.; Qian Liu, Ballwin, Mo.; Frederique Menzaghi, San Diego, Calif.; Joseph F. Russo, Murrieta, Calif.; Julian R. Smith, Devon, United Kingdom; William J. Thomsen, Del Mar, Calif.

[73] Assignee: Arena Pharmaceuticals, Inc., San Diego, Calif.

[21] Appl. No.: 09/418,721

[22] Filed: Oct. 15, 1999

Related U.S. Application Data

[63] Continuation-in-part of application No. 09/292,069, Apr. 14, 1999.
[60] Provisional application No. 60/152,708, Sep. 7, 1999, provisional application No. 60/112,909, Dec. 18, 1998, provisional application No. 60/123,000, Mar. 5, 1999, provisional application No. 09/292,071, Apr. 14, 1999, and provisional application No. 09/292,072, Apr. 14, 1999.

[51] Int. Cl.$^7$ ...................... A61K 31/415; C07D 231/16
[52] U.S. Cl. .................... 514/406; 548/375.1; 548/377.1
[58] Field of Search .............................. 548/375.1, 377.1; 514/406

[56] References Cited

U.S. PATENT DOCUMENTS

| | | | |
|---|---|---|---|
| 4,985,352 | 1/1991 | Julius et al. | 435/6 |
| 5,661,024 | 8/1997 | Kao et al. | 435/240.2 |

FOREIGN PATENT DOCUMENTS

| | | |
|---|---|---|
| 2135253 | 5/1996 | Canada . |
| 4-124178 | 4/1992 | Japan . |
| WO 96/23783 | 8/1996 | WIPO . |

OTHER PUBLICATIONS

Koyanagi et al., CA 117:171439, 1992.
Barluenga, J. et al., "A New and Specific Method for the Monomethylation of Primary Amines," *J. Chem. Soc. Chem. Commun.*, 1984, 20, 1334–1335.
Batey, R.A. et al., "An Efficient New Protocol for the Formation of Unsymmetrical Tri–and Tetrasubstituted Ureas," *Tetra. Lett.*, 1998, 39, 6267–6270.
Bernatowicz, M. et al., "A Comparison of Acid Labile Linkage Agents for the Synthesis of Peptide C–Terminal Amides," *Tetra. Lett.*, 1989, 30(35), 4645–4648.
Carter, H.E. et al., "Carbobenzoxy Chloride and Derivatives," *Org. Syn. Coll.*, 1955, vol. 3, 167–169.
Casey, C. et al., "Constitutively Active Mutant 5HT$_{2A}$ Serotonin Receptors: Inverse Agonist Activity of Classical 5HT$_{2A}$ Antogonists," *Society for Neuroscience Abstracts*, 1996, 22(3), Abstract No. 699.10.
Gutsche, C.D. et al., "2–Phenylcycloheptanone," *Org. Syn. Coll.*, 1963, vol. 4, 780–783.
Herrick–Davis, K. et al., "Activating Mutations of the Serotonin 5–HT$_{2C}$ Receptor," *J. Neurochem.*, 1997, 69(3), 1138–1144.
Herrick–Davis, K. et al., "Constitutively Active 5HT2C Serotonin Receptor Created by Site–Directed Mutagenesis," *Society for Neuroscience Abstracts*, 1996, 22(3), Abstract No. 699.18.
Konig, W. et al., "A New Method for Synthesis of Peptides: Activation of the Carboxyl Group with Dicyclohexylcarbodiimide using 1–Hydroxybenzotriazoles as Additives," *Chem. Ber.*, 1970, 103, 788–798 (English abstract included).
Marchini, P. et al., "Sodium Borohydride–Carboxylic Acid Systems. Useful Reagents for the Alkylation of Amines," *J. Org. Chem.*, 1975, 40(23), 3453–3456.
Sahgal, A. (ed.), "Practical behavorial neuroscience: problems, pitfalls and suggestions," in *Behaviorial Neuroscience: A Practical Approach*, IRL Press, New York, 1993, vol. 1, 1–8.
Sheehan, J.C. et al., "1–Ethyl–3–(3–Dimethylamiono)Propylcarbodiimide Hydrochloride and Methiodide," *Org. Syn. Coll.*, 1973, vol. 5, 555–558.
Soresnon et al., "Characterization of the 5–HT$_2$ Receptor Antagonist MDL 100907 as a Putative Atypical Antipsychotic: Behavorial, Electrophysiological and Neurochemical Studies," *J. Pharmacol. Exp. Ther.*, 1993, 266(2), 684–691.
White, E., "Deamination of Amines. 2–Phenylethyl Benzoate Via the Nitrosoamide Decomposition," *Org. Syn. Coll.*, 1973, vol. 5, 336–339.

*Primary Examiner*—Laura L. Stockton
*Attorney, Agent, or Firm*—Woodcock Washburn Kurtz Mackiewiz & Norris LLP

[57] ABSTRACT

Disclosed herein are non-endogenous, constitutively activated forms of the human 5-HT$_{2A}$ and human 5-HT$_{2C}$ receptors and uses of such receptors to screen candidate compounds. Further disclosed herein are candidate compounds identified by the screening method which act at the 5HT$_{2A}$ receptors. Yet further disclosed is a new class of compounds which act at the 5HT$_{2A}$ receptors.

12 Claims, 8 Drawing Sheets

7A-116081

7B-CLOZAPINE

*Xho I (1312) to Sca I (3049) is identical to pRc/RSV Xho I (3045) to 4782.
*Sca I (3049) to 4070 is identical to pCDM7 Amp ScaI (2524) to 3545.
*multiple cloning site includes Hind III to Sac I of pBluescript II.
*110 to 1312 is identical to pCMD7 Amp 76 to 1278.
*Sac I and Spe I in MCS are not unique.

SMALL MOLECULE MODULATORS OF NON-ENDOGENOUS, CONSTITUTIVELY ACTIVATED HUMAN SEROTONIN RECEPTORS

This application is a Continuation-In-Part of U.S. Ser. No. 09/292,069 filed Apr. 14, 1999, now pending which claims the benefit of U.S. Provisional No. 60/152,708, filed Sep. 7, 1999, U.S. Provisional No. 60/112,909, filed Dec. 18, 1998, U.S. Provisional No. 60/123,000 filed Mar. 5, 1999, U.S. Ser. No. 09/292,071, U.S. Ser. Nos. 09/292,072 and 09/292,069, all filed Apr. 14, 1999, is hereby claimed.

FIELD OF THE INVENTION

The present invention relates to small molecule modulators of non-endogenous, constitutively active serotonin receptors thereof; preferably, the small molecule modulators are preferentially selective for the human $5HT_{2A}$ receptor over the human $5HT_{2C}$ receptor, and most preferably, the small molecule modulators are inverse agonists to the $5HT_{2A}$ receptor.

BACKGROUND OF THE INVENTION

I. G protein-coupled receptors

G protein-coupled receptors share a common structural motif. All these receptors have seven sequences of between 22 to 24 hydrophobic amino acids that form seven alpha helices, each of which spans the membrane. The transmembrane helices are joined by strands of amino acids having a larger loop between the fourth and fifth transmembrane helix on the extracellular side of the membrane. Another larger loop, composed primarily of hydrophilic amino acids, joins transmembrane helices five and six on the intracellular side of the membrane. The carboxy terminus of the receptor lies intracellularly with the amino terminus in the extracellular space. It is thought that the loop joining helices five and six, as well as, the carboxy terminus, interact with the G protein. Currently, Gq, Gs, Gi and Go are G proteins that have been identified. The general structure of G protein-coupled receptors is shown in FIG. 1.

Under physiological conditions, G protein-coupled receptors exist in the cell membrane in equilibrium between two different states or conformations: an "inactive" state and an "active" state. As shown schematically in FIG. 2, a receptor in an inactive state is unable to link to the intracellular transduction pathway to produce a biological response. Changing the receptor conformation to the active state allows linkage to the transduction pathway and produces a biological response.

A receptor may be stabilized in an active state by an endogenous ligand or an exogenous agonist ligand. Recent discoveries such as, including but not exclusively limited to, modifications to the amino acid sequence of the receptor provide means other than ligands to stabilize the active state conformation. These means effectively stabilize the receptor in an active state by simulating the effect of a ligand binding to the receptor. Stabilization by such ligand-independent means is termed "constitutive receptor activation."

II. Serotonin receptors

Receptors for serotonin (5-hydroxytryptamine, 5-HT) are an important class of G protein-coupled receptors. Serotonin is thought to play a role in processes related to learning and memory, sleep, thermoregulation, mood, motor activity, pain, sexual and aggressive behaviors, appetite, neurodegenerative regulation, and biological rhythms. Not surprisingly, serotonin is linked to pathophysiological conditions such as anxiety, depression, obsessive-compulsive disorders, schizophrenia, suicide, autism, migraine, emesis, alcoholism, and neurodegenerative disorders. With respect to on anti-psychotic treatment approaches focused on the serotonin receptors, these types of therapeutics can generally be divided into two classes, the "typical" and the "atypical." Both have anti-psychotic effects, but the typicals also include concomitant motor-related side effects (extra pyramidal syndromes, e.g., lip-smacking, tongue darting, locomotor movement, etc). Such side effects are thought to be associated with the compounds interacting with other receptors, such as the human dopamine D2 receptor in the nigro-striatal pathway. Therefore, an atypical treatment is preferred. Haloperidol is considered a typical anti-psychotic, and clozapine is considered an atypical anti-psychotic.

Serotonin receptors are divided into seven subfamilies, referred to as 5-HT1 through 5-HT7, inclusive. These subfamilies are further divided into subtypes. For example, the 5-HT2 subfamily is divided into three receptor subtypes: $5\text{-}HT_{2A}$, $5\text{-}HT_{2B}$, and $5\text{-}HT_{2C}$. The human $5\text{-}HT_{2C}$ receptor was first isolated and cloned in 1987, and the human $5\text{-}HT_{2A}$ receptor was first isolated and cloned in 1990. These two receptors are thought to be the site of action of hallucinogenic drugs. Additionally, antagonists to the $5\text{-}HT_{2A}$ and $5\text{-}HT_{2C}$ receptors are believed to be useful in treating depression, anxiety, psychosis, and eating disorders.

U.S. Pat. No. 4,985,352 describes the isolation, characterization, and expression of a functional cDNA clone encoding the entire human 5-HT1C receptor (now known as the $5\text{-}HT_{2C}$ receptor). U.S. Pat. No. 5,661,012 describes the isolation, characterization, and expression of a functional cDNA clone encoding the entire human $5\text{-}HT_{2A}$ receptor.

Mutations of the endogenous forms of the rat $5\text{-}HT_{2A}$ and rat $5\text{-}HT_{2C}$ receptors have been reported to lead to constitutive activation of these receptors ($5\text{-}HT_{2A}$: Casey, C. et al. (1996) Society for Neuroscience Abstracts, 22:699.10, hereinafter "Casey"; 5-HT2C: Herrick-Davis, K., and Teitler, M. (1996) Society for Neuroscience Abstracts, 22:699.18, hereinafter "Herrick-Davis 1"; and Herrick-Davis, K. et al. (1997) J. Neurochemistry 69(3): 1138, hereinafter "Herrick-Davis-2"). Casey describes a mutation of the cysteine residue at position 322 of the rat $5\text{-}HT_{2A}$ receptor to lysine (C322K), glutamine (C322Q), and arginine (C322R) which reportedly led to constitutive activation. Herrick-Davis 1 and Herrick-Davis 2 describe mutations of the serine residue at position 312 of the rat $5\text{-}HT_{2C}$ receptor to phenylalanine (S312F) and lysine (S312K), which reportedly led to constitutive activation.

SUMMARY OF THE INVENTION

The present invention relates to small molecule modulators of non-endogenous, constitutively activated forms of the human $5\text{-}HT_{2A}$ and human $5\text{-}HT_{2C}$ receptors that are, preferably, preferentially selective for the $5\text{-}HT_{2A}$ receptor, and most preferably, have inverse agonist characteristics at the receptor.

BRIEF DESCRIPTION OF THE DRAWINGS

In the following figures, bold typeface indicates the location of the mutation in the non-endogenous, constitutively activated receptor relative to the corresponding endogenous receptor.

TABLE 1

Figure 1:
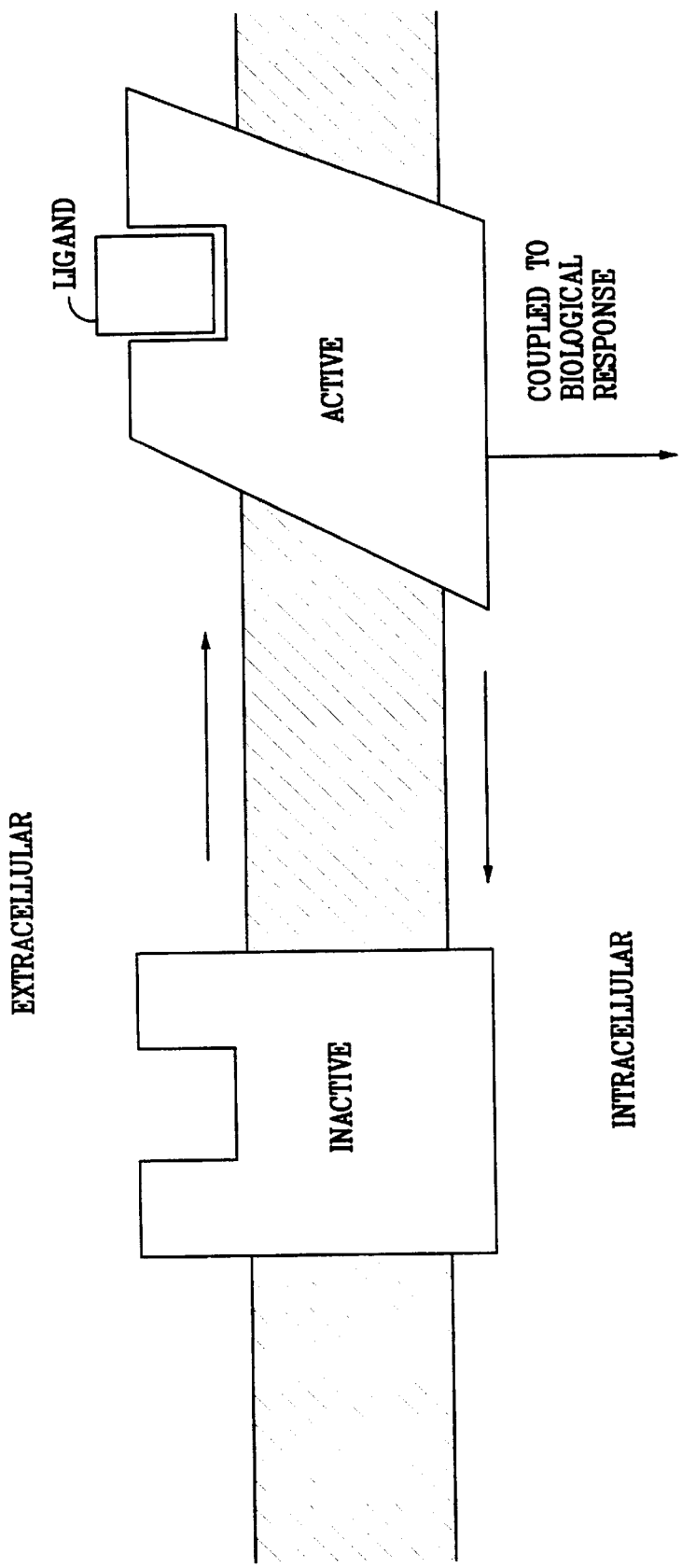
FIG. 1 shows a generalized structure of a G protein-coupled receptor with the numbers assigned to the transmembrane helices, the intracellular loops, and the extracellular loops.
Figure 2:
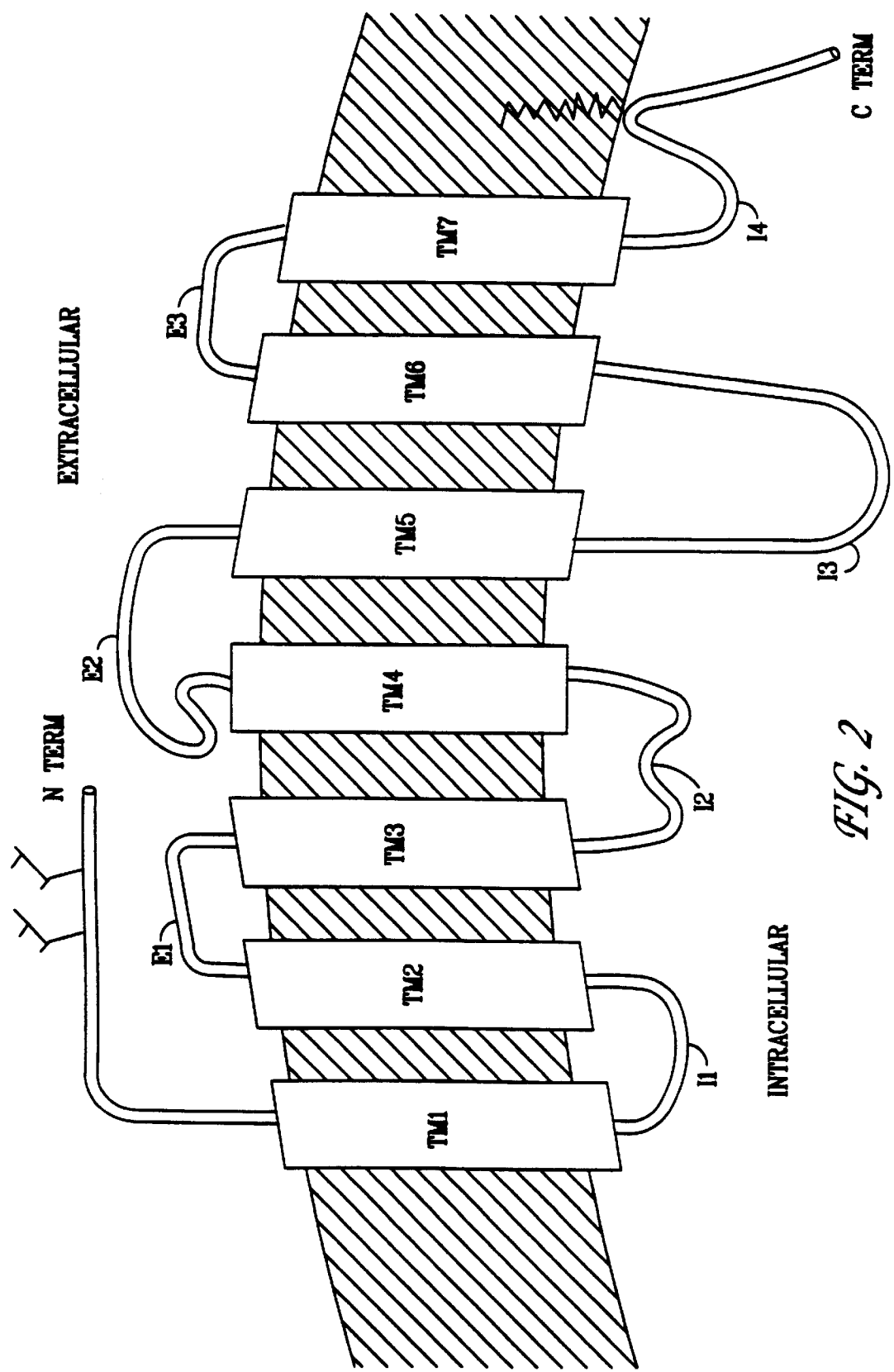
FIG. 2 schematically shows the active and inactive states for a typical G protein-coupled receptor and the linkage of the active state to the second messenger transduction pathway.

| ALANINE | ALA | A |
| ARGININE | ARG | R |
| ASPARAGINE | ASN | N |
| ASPARTIC ACID | ASP | D |
| CYSTEINE | CYS | C |
| GLUTAMIC ACID | GLU | E |
| GLUTAMINE | GLN | Q |
| GLYCINE | GLY | G |
| HISTIDINE | HIS | H |
| ISOLEUCINE | ILE | I |
| LEUCINE | LEU | L |
| LYSINE | LYS | K |
| METHIONINE | MET | M |
| PHENYLALANINE | PHE | F |
| PROLINE | PRO | P |
| SERINE | SER | S |
| THREONINE | THR | T |
| TRYPTOPHAN | TRP | W |
| TYROSINE | TYR | Y |
| VALINE | VAL | V |

PARTIAL AGONISTS shall mean moieties which activate the intracellular response when they bind to the receptor to a lesser degree/extent than do agonists, or enhance GTP binding to membranes to a lesser degree/extent than do agonists.

ANTAGONIST shall mean moieties that competitively bind to the receptor at the same site as the agonists but which do not activate the intracellular response initiated by the active form of the receptor, and can thereby inhibit the intracellular responses by agonists or partial agonists. ANTAGONISTS do not diminish the baseline intracellular response in the absence of an agonist or partial agonist.

CANDIDATE COMPOUND shall mean a molecule (for example, and not limitation, a chemical compound) which is amenable to a screening technique.

COMPOSITION shall mean a material comprising at least two compounds or two components; for example, and not limitation, a Pharmaceutical Composition is a Composition.

COMPOUND EFFICACY shall mean a measurement of the ability of a compound to inhibit or stimulate receptor functionality, as opposed to receptor binding affinity.

CONSTITUTIVELY ACTIVATED RECEPTOR shall mean a receptor subject to constitutive receptor activation.

CONSTITUTIVE RECEPTOR ACTIVATION shall mean stabilization of a receptor in the active state by means other than binding of the receptor with its endogenous ligand or a chemical equivalent thereof.

CONTACT or CONTACTING shall mean bringing at least two moieties together, whether in an in vitro system or an in vivo system.

ENDOGENOUS shall mean a material that a mammal naturally produces. ENDOGENOUS in reference to, for example and not limitation, the term "receptor" shall mean that which is naturally produced by a mammal (for example, and not limitation, a human) or a virus. In contrast, the term NON-ENDOGENOUS in this context shall mean that which is not naturally produced by a mammal (for example, and not limitation, a human) or a virus. For example, and not limitation, a receptor which is not constitutively active in its endogenous form, but when manipulated becomes constitutively active, is most preferably referred to herein as a "non-endogenous, constitutively activated receptor." Both terms can be utilized to describe both "in vivo" and "in vitro" systems. For example, and not a limitation, in a screening approach, the endogenous or non-endogenous receptor may be in reference to an in vitro screening system. As a further example and not limitation, where the genome of a mammal has been manipulated to include a non-endogenous constitutively activated receptor, screening of a candidate compound by means of an in vivo system is viable.

INHIBIT or INHIBITING, in relationship to the term "response" shall mean that a response is decreased or prevented in the presence of a compound as opposed to in the absence of the compound.

INVERSE AGONISTS shall mean moieties that bind the endogenous form of the receptor or to the constitutively activated form of the receptor, and which inhibit the baseline intracellular response initiated by the active form of the receptor below the normal base level of activity which is observed in the absence of agonists or partial agonists, or decrease GTP binding to membranes. Preferably, the baseline intracellular response is inhibited in the presence of the inverse agonist by at least 30%, more preferably by at least 50%, and most preferably by at least 75%, as compared with the baseline response in the absence of the inverse agonist.

LIGAND shall mean an endogenous, naturally occurring molecule specific for an endogenous, naturally occurring receptor.

PHARMACEUTICAL COMPOSITION shall mean a composition comprising at least one active ingredient, whereby the composition is amenable to investigation for a specified, efficacious outcome in a mammal (for example, and not limitation, a human). Those of ordinary skill in the art will understand and appreciate the techniques appropriate for determining whether an active ingredient has a desired efficacious outcome based upon the needs of the artisan.

STIMULATE or STIMULATING, in relationship to the term "response" shall mean that a response is increased in the presence of a compound as opposed to in the absence of the compound.

DETAILED DESCRIPTION

I. Particularly preferred mutations

For convenience, the sequence information regarding the non-endogenous, constitutively active human $5\text{-HT}_{2A}$ and $5\text{-HT}_{2C}$ receptors are referred to by identifiers as set forth in Table 2:

TABLE 2

| IDENTIFIER | RECEPTOR | SEQ.ID.NO: |
|---|---|---|
| AP-1 cDNA | $5\text{-HT}_{2C}$ | 22 |
| AP-1 | $5\text{-HT}_{2C}$ | 23 |
| AP-3 cDNA | $5\text{-HT}_{2A}$ | 24 |
| AP-3 | $5\text{-HT}_{2A}$ | 25 |
| AP-4 cDNA | $5\text{-HT}_{2A}$ | 26 |
| AP-4 | $5\text{-HT}_{2A}$ | 27 |

As will be discussed in greater detail below, a mutation analogous to that reported by Casey (C322K) was utilized in the human $5\text{-HT}_{2A}$ receptor and is referred to herein as AP-2. However, AP-2 did not lead to sufficient constitutive activation to allow for utilization in screening techniques.

II. Generic G Protein-Coupled Receptor screening assay techniques

When a G protein receptor becomes constitutively active, it binds to a G protein (Gq, Gs, Gi, Go) and stimulates the binding of GTP to the G protein. The G protein then acts as a GTPase and slowly hydrolyzes the GTP to GDP, whereby the receptor, under normal conditions, becomes deactivated. However, constitutively activated receptors continue to exchange GDP to GTP. A non-hydrolyzable analog of GTP, [$^{35}$S]GTPγS, can be used to monitor enhanced binding to membranes which express constitutively activated receptors. It is reported that [$^{35}$S]GTPγS can be used to monitor G protein coupling to membranes in the absence and presence of ligand. An example of this monitoring, among other examples well-known and available to those in the art, was reported by Traynor and Nahorski in 1995. The preferred use of this assay system is for initial screening of candidate compounds because the system is generically applicable to all G protein-coupled receptors regardless of the particular G protein that interacts with the intracellular domain of the receptor.

III. Confirmation of G Protein-Coupled Receptor site screening assay techniques

Once candidate compounds are identified using the "generic" G protein-coupled receptor assay (i.e. an assay to select compounds that are agonists, partial agonists, or inverse agonists), further screening to confirm that the compounds have interacted at the receptor site is preferred. For example, a compound identified by the "generic" assay may not bind to the receptor, but may instead merely "uncouple" the G protein from the intracellular domain. Thus, by further screening those candidate compounds, which have been identified using a "generic" assay in an agonist and/or antagonist competitive binding assay, further refinement in the selection process is provided.

Lysergic acid diethylamide (LSD) is a well-known agonist of the $5\text{-HT}_{2A}$ and $5\text{-HT}_{2C}$ receptors, while mesulergine is a well-known antagonist to the $5\text{-HT}_{2C}$ receptor. Accordingly, in most preferred embodiments, an agonist (LSD) and/or antagonist (mesulergine) competitive binding assay(s) is used to further screen those compounds selected from the "generic" assay for confirmation of serotonin receptor binding.

IV. Specified G Protein assay techniques

The art-accepted physiologically mediated pathway for the human $5\text{-HT}_{2A}$ and $5\text{-HT}_{2C}$ receptors is via Gq. Intracellular accumulation of IP3 can be used to confirm constitutive activation of these types of Gq coupled receptors (see Herrick-Davis-1). As a result, "IP3 accumulation" assays can be used to further screen those compounds selected from an agonist and/or antagonist competitive binding assay.

V. Pharmaceutical compositions

Candidate compounds selected for further development can be formulated into pharmaceutical compositions using techniques well known to those in the art. Suitable pharmaceutically-acceptable carriers are available to those in the art; for example, see Remington's Pharmaceutical Sciences, 16$^{th}$ Edition, 1980, Mack Publishing Co., (Oslo et al., eds.)

EXAMPLES

The following examples are presented for purposes of elucidation, and not limitation, of the present invention. While specific nucleic acid and amino acid sequences are disclosed herein, those of ordinary skill in the art are credited with the ability to make minor modifications to these sequences while achieving the same or substantially similar results reported below. It is intended that equivalent, non-endogenous, constitutively activated human serotonin receptor sequences include those having eighty-five percent (85%) homology, more preferably having ninety percent (90%) homology, and most preferably having ninety-five percent (95%) homology to the disclosed sequences.

Example 1

Generation of Non-Endogenous, Constitutively Activated Human Serotonin Receptors $5\text{-HT}_{2C}$ and $5\text{-HT}_{2A}$ A. Construction of constitutively active $5\text{-HT}_{2C}$ receptor cDNA 1. Endogenous Human $5\text{-HT}_{2C}$ The cDNA encoding endogenous human $5\text{-HT}_{2C}$ receptor was obtained from human brain poly-A$^+$ RNA by RT-PCR.

The 5' and 3' primers were derived from the 5' and 3' untranslated regions and contained the following sequences:

5'-GACCTCGAGGTTGCTTAAGACTGAAGCA-3' (SEQ.ID.NO.:1)
5'-ATTTCTAGACATATGTAGCTTGTACCGT-3' (SEQ.ID.NO.:2)

PCR was performed using either TaqPlus™ precision polymerase (Stratagene) or rTth™ polymerase (Perkin Elmer) with the buffer systems provided by the manufacturers, 0.25 M of each primer, and 0.2 mM of each of the four (4) nucleotides. The cycle condition was 30 cycles of 94° C. for 1 minute, 57° C. for 1 minute and 72° C. for 2 minutes. The 1.5 kb PCR fragment was digested with Xho I and Xba I and subcloned into the Sal I-Xba I site of pBluescript.

The derived cDNA clones were fully sequenced and found to correspond to published sequences.

2. AP-1 cDNA

The cDNA containing a S310K mutation (AP-1 cDNA) in the third intracellular loop of the human $5\text{-}HT_{2C}$ receptor was constructed by replacing the Sty I restriction fragment containing amino acid 310 with synthetic double stranded oligonucleotides encoding the desired mutation. The sense strand sequence utilized had the following sequence:

5'-CTAGGGGCACCATGCAGGCTATCAACAATGAAA GAAAAGCTAAGAAAGTC-3' (SEQ. ID.NO: 3)
and the antisense strand sequence utilized had the following sequence:

5'-CAAGGACTTTCTTAGCTTTTCTTTCATTGTTGA TAGCCTGCATGGTGCCC-3' (SEQ. ID. NO: 4).

B. Construction of constitutively active $5\text{-}HT_{2A}$ receptor cDNA

1. Endogenous Human $5\text{-}HT_{2A}$

The cDNA encoding endogenous human $5\text{-}HT_{2A}$ receptor was obtained by RT-PCR using human brain poly-A$^+$ RNA; a 5' primer from the 5' untranslated region with a Xho I restriction site:

5'-GACCTCGAGTCCTTCTACACCTCATC-3' (SEQ.ID.NO:5)

and a 3' primer from the 3' untranslated region containing an Xba I site:

5'-TGCTCTAGATTCCAGATAGGTGAAAA CTTG-3' (SEQ.ID.NO:6).

PCR was performed using either TaqPlus™ precision polymerase (Stratagene) or rTth™ polymerase (Perkin Elmer) with the buffer systems provided by the manufacturers, 0.25 µM of each primer, and 0.2 mM of each of the four (4) nucleotides. The cycle condition was 30 cycles of 94° C. for 1 minute, 57° C. for 1 minute and 72° C. for 2 minutes. The 1.5 kb PCR fragment was digested with Xba I and subcloned into the Eco RV-Xba I site of pBluescript.

The resulting cDNA clones were fully sequenced and found to encode two amino acid changes from the published sequences. The first change is a T25N mutation in the N-terminal extracellular domain and the second change is an H452Y mutation. These mutations are likely to represent sequence polymorphisms rather than PCR errors since the cDNA clones having the same two mutations were derived from two independent PCR procedures using Taq polymerase from two different commercial sources (TaqPlus™ Stratagene and rTth™ Perkin Elmer).

2. Human $5\text{-}HT_{2A}$ (C322K; AP-2)

The cDNA containing the point mutation C322K in the third intracellular loop was constructed by using the Sph I restriction enzyme site, which encompasses amino acid 322. For the PCR procedure, a primer containing the C322K mutation:

5'-CAAAGAAAGTACTGGGCATCGTCTTCTTCCT-3' (SEQ.ID.NO:7)

was used along with the primer from the 3' untranslated region set forth above as SEQ.ID.NO:6. The resulting PCR fragment was then used to replace the 3' end of the wild type 5-HT2A cDNA by the T4 polymerase blunted Sph I site. PCR was performed using pfu polymerase (Stratagene) with the buffer system provided by the manufacturer and 10% DMSO, 0.25 mM of each primer, 0.5 mM of each of the 4 nucleotides. The cycle conditions were 25 cycles of 94° C. for 1 minute, 60° C. for 1 minute, and 72° C. for 1 minute.

3. AP-3 cDNA

The human $5\text{-}HT_{2A}$ cDNA with intracellular loop 3 (IC3) or IC3 and cytoplasmic tail replaced by the corresponding human $5\text{-}HT_{2C}$ cDNA was constructed using PCR-based mutagenesis.

(a) Replacement of IC3 Loop

The IC3 loop of human $5\text{-}HT_{2A}$ cDNA was first replaced with the corresponding human $5\text{-}HT_{2C}$ cDNA. Two separate PCR procedures were performed to generate the two fragments, Fragment A and Fragment B, that fuse the $5\text{-}HT_{2C}$ IC3 loop to the transmembrane 6 (TM6) of $5\text{-}HT_{2A}$. The 237 bp PCR fragment, Fragment A, containing $5\text{-}HT_{2C}$ IC3 and the initial 13 bp of $5\text{-}HT_{2A}$ TM6 was amplified by using the following primers:

5'-CCGCTCGAGTACTGCGCCGACAAGCTTTGAT-3' (SEQ.ID.NO:8)
5'-CGATGCCCAGCACTTTCGAAGCTTTTCTTTCAT TGTTG-3' (SEQ.ID.NO:9)

The template used was human $5\text{-}HT_{2C}$ cDNA.

The 529 bp PCR fragment, Fragment B, containing the C-terminal 13 bp of IC3 from $5\text{-}HT_{2C}$ and the C-terminal of $5\text{-}HT_{2A}$ starting at beginning of TM6, was amplified by using the following primers:

5'-AAAAGCTTCGAAAGTGCTGGGCATCGTCTTCTT CCT-3' (SEQ.ID.NO:10)
5'-TGCTCTAGATTCCAGATAGGTGAAAACTTG-3' (SEQ.ID.NO: 11)

The template used was human $5\text{-}HT_{2A}$ cDNA.

Second round PCR was performed using Fragment A and Fragment B as co-templates with SEQ.ID.NO:8 and SEQ.ID.NO:11 (it is noted that the sequences for SEQ.ID-.NOS.: 6 and 11 are the same) as primers. The resulting 740 bp PCR fragment, Fragment C, contained the IC3 loop of human $5\text{-}HT_{2C}$ fused to TM6 through the end of the cytoplasmic tail of human $5\text{-}HT_{2A}$. PCR was performed using pfu™ polymerase (Stratagene) with the buffer system provided by the manufacturer, and 10% DMSO, 0.25 mM of each primer, and 0.5 mM of each of the four (4) nucleotides. The cycle conditions were 25 cycles of 94° C. for 1 minute, 57° C. (1st round PCR) or 60° C. (2nd round PCR) for 1 minute, and 72° C. for 1 minute (1st round PCR) or 90 seconds (2nd round PCR).

To generate a PCR fragment containing a fusion junction between the human 5-HT2A TM5 and the IC3 loop of 5-HT$_{2C}$, four (4) primers were used. The two external primers, derived from human 5-HT2A, had the following sequences:

5'-CGTGTCTCTCCTTACTTCA-3' (SEQ.ID.NO:12)

The other primer used was SEQ.ID.NO.:6 (see note above regarding SEQ.ID.NOS. 6 and 11). The first internal primer utilized was an antisense strand containing the initial 13 bp of IC3 of 5-HT$_{2C}$ followed by the terminal 23 bp derived from TM5 of 5-HT$_{2A}$:

5'-TCGGCGCAGTACTTTGATAGTTAGAAAGTAGGT GAT-3' (SEQ.ID.NO:13)

The second internal primer was a sense strand containing the terminal 14 bp derived from TM5 of 5-HT$_{2A}$ followed by the initial 24 bp derived from IC3 of 5-HT$_{2C}$:

5'-TTCTAACTATCAAAGTACTGCGCCGACAAGCTT TGATG-3' (SEQ.ID.NO:14).

PCR was performed using endogenous human 5-HT2A and a co-template, Fragment C, in a 50 ml reaction volume containing 1× pfu buffer, 10% DMSO, 0.5 mM of each of the four (4) nucleotides, 0.25 mM of each external primer (SEQ.ID.NOS. 11 and 12), 0.06 mM of each internal primer (SEQ.ID.NOS. 13 and 14) and 1.9 units of pfu polymerase (Stratagene). The cycle conditions were 25 cycles of 94° C. for 1 minute, 52° C. for 1 minute, and 72° C. for 2 minutes and 10 seconds. The 1.3 kb PCR product was then gel purified and digested with Pst I and Eco RI. The resulting 1 kb PstI-Eco RI fragment was used to replace the corresponding fragment in the endogenous human 5-HT$_{2A}$ sequence to generate the mutant 5-HT$_{2A}$ sequence encoding the IC3 loop of 5-HT$_{2C}$.

(b) Replacement of the cytoplasmic tail

To replace the cytoplasmic tail of 5-HT$_{2A}$ with that of 5-HT$_{2C}$, PCR was performed using a sense primer containing the C-terminal 22 bp of TM7 of endogenous human 5-HT$_{2A}$ followed by the initial 21 bp of the cytoplasmic tail of endogenous human 5-HT$_{2C}$:

5'-TTCAGCAGTCAACCCACTAGTCTATACTCTGTT CAACAAAATT-3' (SEQ.ID.NO:15)

The antisense primer was derived from the 3' untranslated region of endogenous human 5-HT2C:

5'-ATTTCTAGACATATGTAGCTTGTACCGT-3' (SEQ.ID.NO:16).

The resulting PCR fragment, Fragment D, contained the last 22 bp of endogenous human 5-HT$_{2A}$ TM7 fused to the cytoplasmic tail of endogenous human 5-HT$_{2C}$. Second round PCR was performed using Fragment D and the co-template was endogenous human 5-HT2A that was previously digested with Acc I to avoid undesired amplification. The antisense primer used was SEQ.ID.NO:16 (the sequences for SEQ.ID.NOS. 16 and 2 are the same) and the sense primer used was derived from endogenous human 5-HT$_{2A}$:

5'-ATCACCTACTTTCTAACTA-3' (SEQ.ID.NO:17).

PCR conditions were as set forth in Example 1B3(a) for the first round PCR, except that the annealing temperature was 48° C. and the extension time was 90 seconds. The resulting 710 bp PCR product was digested with Apa I and Xba I and used to replace the corresponding Apa I-Xba I fragment of either (a) endogenous human 5-HT$_{2A}$, or (b) 5-HT$_{2A}$ with 2C IC3 to generate (a) endogenous human 5-HT$_{2A}$ with endogenous human 5-HT$_{2C}$ cytoplasmic tail and (b) AP-3, respectively.

4. AP-4 cDNA

This mutant was created by replacement of the region of endogenous human 5-HT$_{2A}$ from amino acid 247, the middle of TM5 right after Pro$^{246}$, to amino acid 337, the middle of TM6 just before Pro$^{338}$, by the corresponding region of AP-1 cDNA. For convenience, the junction in TM5 is referred to as the "2A-2C junction," and the junction in TM6 is referred to as the "2C-2A junction."

Three PCR fragments containing the desired hybrid junctions were generated. The 5' fragment of 561 bp containing the 2A-2C junction in TM5 was generated by PCR using endogenous human 5-HT$_{2A}$ as template, SEQ.ID.NO:12 as the sense primer, and the antisense primer was derived from 13 bp of 5-HT$_{2C}$ followed by 20 bp of 5-HT$_{2A}$ sequence:

5'-CCATAATCGTCAGGGGAATGAAAAATGACACAA-3' (SEQ.ID.NO:18)

The middle fragment of the 323 bp contains endogenous human 5-HT$_{2C}$ sequence derived from the middle of TM5 to the middle of TM6, flanked by 13 bp of 5-HT$_{2A}$ sequences from the 2A-2C junction and the 2C-2A junction. This middle fragment was generated by using AP-1 cDNA as a template, a sense primer containing 13 bp of 5-HT$_{2A}$ followed by 20 bp of 5-HT$_{2C}$ sequences across the 2A-2C junction and having the sequence:

5'-ATTTTTCATTCCCCTGACGATTATGGTGATTAC-3' (SEQ.ID.NO:19);

and an antisense primer containing 13 bp of 5-HT$_{2A}$ followed by 20 bp of 5-HT$_{2C}$ sequences across the 2C-2A junction and having the sequence:

5'-TGATGAAGAAAGGGCACCACATGATCAGAA ACA-3' (SEQ.ID.NO:20).

The 3' fragment of 487 bp containing the 2C-2A junction was generated by PCR using endogenous human 5-HT$_{2A}$ as a template and a sense primer having the following sequence from the 2C-2A junction:

5'-GATCATGTGGTGCCCTTTCTTCATCACAAACAT-3' (SEQ.ID.NO:21)

and the antisense primer was SEQ.ID.NO:6 (see note above regarding SEQ.ID.NOS. 6 and 11).

Two second round PCR reactions were performed separately to link the 5' and middle fragment (5'M PCR) and the middle and 3' fragment (M3' PCR). The 5'M PCR co-template used was the 5' and middle PCR fragment as described above, the sense primer was SEQ.ID.NO:12 and the antisense primer was SEQ.ID.NO:20. The 5'M PCR procedure resulted in an 857 bp PCR fragment.

The M3' PCR used the middle and M3' PCR fragment described above as the co-template, SEQ.ID.NO: 19 as the sense primer and SEQ.ID.NO:6 (see note above regarding SEQ.ID.NOS. 6 and 11) as the antisense primer, and generated a 784 bp amplification product. The final round of PCR was performed using the 857 bp and 784 bp fragments from the second round PCR as the co-template, and SEQ.ID.NO:12 and SEQ.ID.NO: 6 (see note above regarding SEQ.ID.NOS. 6 and 11) as the sense and the antisense primer, respectively. The 1.32 kb amplification product from the final round of PCR was digested with Pst I and Eco RI. Then resulting 1 kb Pst I-Eco RI fragment was used to replace the corresponding fragment of the endogenous human $5\text{-}HT_{2A}$ to generate mutant $5\text{-}HT_{2A}$ with $5\text{-}HT_{2C}$: C310K/IC3. The Apa I-Xba fragment of AP3 was used to replace the corresponding fragment in mutant $5\text{-}HT_{2A}$ with $5\text{-}HT_{2C}$: C310K/IC3 to generate AP4.

Example 2

Receptor Expression

A. pCMV

Figure 8:
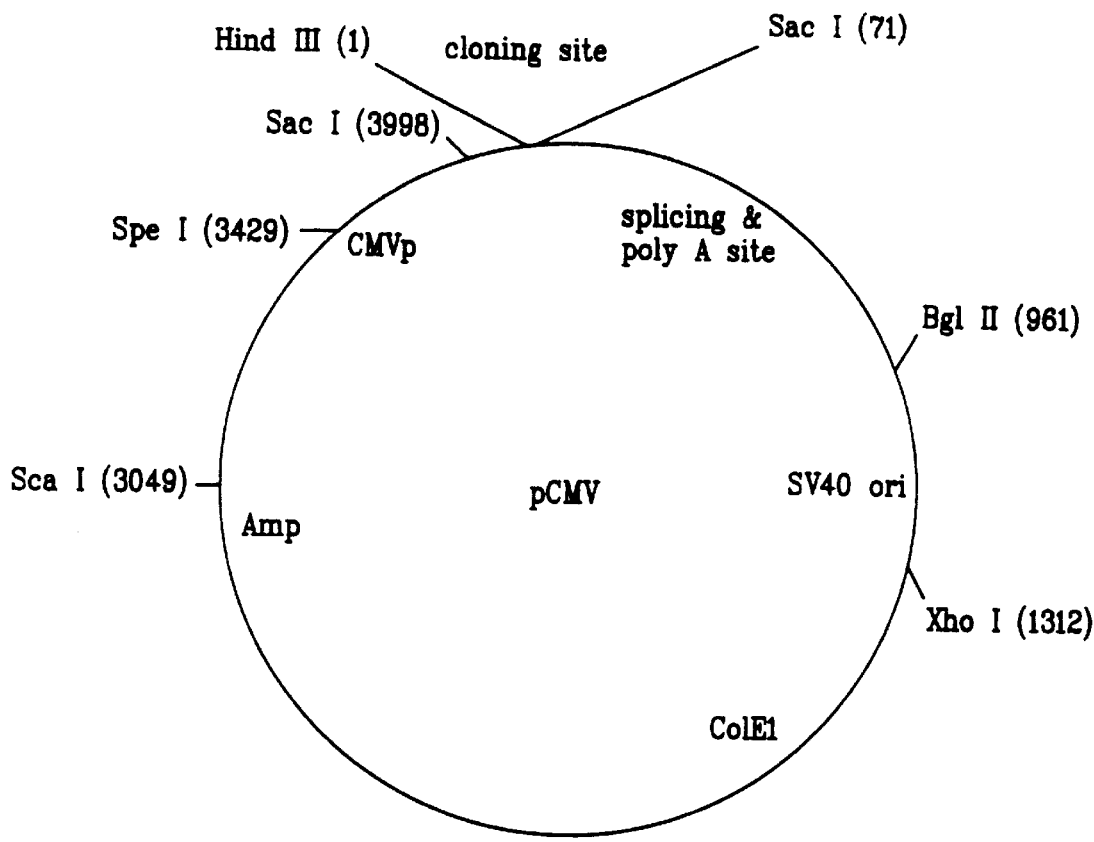
FIG. 8 is a representation of the preferred vector, pCMV, used herein.

Although a variety of expression vectors are available to those in the art, for purposes of utilization for both the endogenous and non-endogenous receptors discussed herein, it is most preferred that the vector utilized be pCMV. This vector was deposited with the American Type Culture Collection (ATCC) on Oct. 13, 1998 (10801 University Blvd., Manassas, Va. 20110-2209 USA) under the provisions of the Budapest Treaty for the International Recognition of the Deposit of Microorganisms for the Purpose of Patent Procedure. The DNA was tested by the ATCC and determined to be viable. The ATCC has assigned the following deposit number to pCMV: ATCC #203351. See FIG. 8.

B. Transfection procedure

For the generic assay ($[^{35}S]GTP\gamma S$; Example 3) and the antagonist binding assay (mesulergine; Example 4), transfection of COS-7 or 293T cells was accomplished using the following protocol.

On day one, $5 \times 10^6$ COS-7 cells or $1 \times 10^7$ 293T cells per 150 mm plate were plated out. On day two, two reaction tubes were prepared (the proportions to follow for each tube are per plate): tube A was prepared by mixing 20 μg DNA (e.g., pCMV vector; pCMV vector AP-1 cDNA, etc.) in 1.2 ml serum free DMEM (Irvine Scientific, Irvine, Calif.); tube B was prepared by mixing 120 μl lipofectamine (Gibco BRL) in 1.2 ml serum free DMEM. Tubes A and B were then admixed by inversions (several times), followed by incubation at room temperature for 30–45 min. The admixture is referred to as the "transfection mixture". Plated COS-7 cells were washed with 1× PBS, followed by addition of 10 ml serum free DMEM. 2.4 ml of the transfection mixture was then added to the cells, followed by incubation for 4 hrs at 37° C./5% $CO_2$. The transfection mixture was then removed by aspiration, followed by the addition of 25 ml of DMEM/ 10% Fetal Bovine Serum. Cells were then incubated at 37° C./5% $CO_2$. After 72 hr incubation, cells were then harvested and utilized for analysis.

Example 3

Protocol: GTP Membrane Binding Scintillation Proximity Assay

The advantages of using $[^{35}S]GTP\gamma S$ binding to measure constitutive activation are that: (a) $[^{35}S]GTP\gamma S$ binding is generically applicable to all G protein-coupled receptors; and (b) $[^{35}S]GTP\gamma S$ binding is proximal at the membrane surface, thereby making it less likely to pick-up molecules which affect the intracellular cascade. The assay utilizes the ability of G protein-coupled receptors to stimulate $[^{35}S]GTP\gamma S$ binding to membranes expressing the relevant receptors. Therefore, the assay may be used to directly screen compounds at the disclosed serotonin receptors.

A scintillation proximity assay can be utilized to monitor the binding of $[^{35}S]GTP\gamma S$ to membranes expressing, e.g., the endogenous human $5\text{-}HT_{2C}$ receptor expressed in COS cells. In brief, a preferred protocol for the assay is such that the assay was incubated in 20 mM HEPES, pH 7.4, binding buffer with 0.3 nM $[^{35}S]GTP\gamma S$ and 12.5 μg membrane protein and 1 μM GDP for 30 minutes. Wheatgerm agglutinin beads (25 μl; Amersham) were then added and the mixture was incubated for another 30 minutes at room temperature. The tubes were then centrifuged at 1500×g for 5 minutes at room temperature and then counted in a scintillation counter. Serotonin, which as the endogenous ligand activates the $5\text{-}HT_{2C}$ receptor, stimulated $[^{35}S]GTP\gamma S$ binding to the membranes in a concentration dependant manner (data not shown). The stimulated binding can be completely inhibited by 30 μM mianserin, a compound considered as a classical $5\text{-}HT_{2C}$ antagonist, but also known as a $5\text{-}HT_{2C}$ inverse agonist (data not shown).

Although this assay measures agonist-induced binding of $[^{35}S]GTP\gamma S$ to membranes and can be routinely used to measure constitutive activity of receptors, the present cost of wheatgerm agglutinin beads may be prohibitive. A less costly but equally applicable alternative also meets the needs of large-scale screening. Flash plates and Wallac™ scintistrips may be used to format a high throughput $[^{35}S]GTP\gamma S$ binding assay. This technique allows one to monitor the tritiated ligand binding to the receptor while simultaneously monitoring the efficacy via $[^{35}S]GTP\gamma S$ binding. This is possible because the Wallac™ beta counter can switch energy windows to analyze both tritium and $^{35}S$-labeled probes.

Also, this assay may be used for detecting of other types of membrane activation events that result in receptor activation. For example, the assay may be used to monitor $^{32}P$ phosphorylation of a variety of receptors (including G protein-coupled and tyrosine kinase receptors). When the membranes are centrifuged to the bottom of the well, the bound $[^{35}S]GTP\gamma S$ or the $^{32}P$-phosphorylated receptor will activate the scintillant coated on the wells. Use of Scinti® strips (Wallac™) demonstrate this principle. Additionally, this assay may be used for measuring ligand binding to receptors using radiolabeled ligands. In a similar manner, the radiolabeled bound ligand is centrifuged to the bottom of the well and activates the scintillant. The $[^{35}S]GTP\gamma S$ assay results parallel the results obtained in traditional second messenger assays of receptors.

In this assay, serotonin stimulates the binding of $[^{35}S]GTP\gamma S$ to the endogenous human $5\text{-}HT_{2C}$ receptor, while mianserin inhibits this response; furthermore, mianserin acts as a partial inverse agonist by inhibiting the basal constitutive binding of $[^{35}S]GTP\gamma S$ to membranes expressing the endogenous human $5\text{-}HT_{2C}$ receptor (data not shown). In this assay, there should be no agonist response in the absence of GDP since there is no GDP present to exchange for $[^{35}S]GTP\gamma S$. This assay system can be used to demonstrate the response of the native $5\text{-}HT_{2C}$ receptor, and to also measures the constitutive activation of other receptors.

Using this assay, enhanced binding of $[^{35}S]GTP\gamma S$ to membranes prepared from 293T cells expressing the control vector alone, the native human $5\text{-}HT_{2C}$ receptor or the AP-1 receptor was observed (data not shown). The total protein concentration used in the assay affects the total amount of

[$^{35}$S]GTPγS binding for each receptor. The c.p.m. differential between the pCMV transfected and the constitutively active mutant receptor increased from approximately 1000 c.p.m at 10 μg/well to approximately 6–8000 c.p.m. at 75 μg/well protein concentration.

The AP-1 receptor showed the highest level of constitutive activation followed by the wild type receptor, which also showed enhanced [$^{35}$S]GTPγS binding above basal. This is consistent with the ability of the endogenous human 5-HT$_{2C}$ receptor to accumulate intracellular IP3 in the absence of 5HT stimulation (Example 5) and is also consistent with published data claiming that the endogenous human 5-HT$_{2C}$ receptor has a high natural basal activity. Therefore, the AP-1 receptor demonstrates that constitutive activity may be measured by proximal [$^{35}$S]GTPγS binding events at the membrane interface.

Example 4

Protocol: Serotonin Receptor Agonist/Antagonist Competitive Binding Assay

Membranes were prepared from transfected COS-7 cells (see Example 2) by homogenization in 20 mM HEPES and 10 mM EDTA, pH 7.4 and centrifuged at 49,000×g for 15 min. The pellet was resuspended in 20 mM HEPES and 0.1 mM EDTA, pH 7.4, homogenized for 10 sec. using polytron homogenizer (Brinkman) at 5000 rpm and centrifuged at 49,000×g for 15 min. The final pellet was resuspended in 20 mM HEPES and 10 mM MgCl$_2$, pH 7.4, homogenized for 10 sec. using polytron homogenizer (Brinkman) at 5000 rpm.

Assays were performed in triplicate 200 μl volumes in 96 well plates. Assay buffer (20 mM HEPES and 10 mM MgCl$_2$, pH 7.4) was used to dilute membranes, $^3$H-LSD, $^3$H-mesulergine, serotonin (used to define non-specific for LSD binding) and mianserin (used to define non-specific for mesulergine binding). Final assay concentrations consisted of 1 nM $^3$H-LSD or 1 nM $^3$H-mesulergine, 50 μg membrane protein and 100 μm serotonin or mianserin. LSD assays were incubated for 1 hr at 37° C., while mesulergine assays were incubated for 1 hr at room temperature. Assays were terminated by rapid filtration onto Wallac Filtermat Type B with ice cold binding buffer using Skatron cell harvester. The radioactivity was determined in a Wallac 1205 BetaPlate counter.

Example 5

Protocol: Intracellular IP$_3$ Accumulation Assay

For the IP$_3$ accumulation assay, a transfection protocol different from the protocol set forth in Example 2 was utilized. In the following example, the protocols used for days 1–3 were slightly different for indicated conditions, as set forth below; the protocol for day 4 was the same for all conditions.

A. COS-7 and 293 Cells

On day one, COS-7 cells or 293 cells were plated onto 24 well plates, usually 1×10$^5$ cells/well or 2×10$^5$ cells/well, respectively. On day two, the cells were transfected by first mixing 0.25 ug DNA (see Example 2) in 50 μl serum-free DMEM/well and then 2 μl lipofectamine in 50 μl serum-free DMEM/well. The solutions ("transfection media") were gently mixed and incubated for 15–30 minutes at room temperature. The cells were washed with 0.5 ml PBS and then 400 μl of serum free media was mixed with the transfection media and added to the cells. The cells were then incubated for 3–4 hours at 37° C./5%CO$_2$. Then the transfection media was removed and replaced with 1 ml/well of regular growth media. On day 3, the media was removed and the cells were washed with 0.5 ml PBS. Then 0.5 ml inositol-free/serum-free media (GIBCO BRL) was added to each well with 0.25 μCi of $^3$H-myo-inositol/well and the cells were incubated for 16–18 hours overnight at 37° C./5%CO$_2$. Protocol A.

B. 293 Cells

On day one, 1×10$^7$ 293 cells per 150 mm plate were plated out. On day two, two reaction tubes were prepared (the proportions to follow for each tube are per plate): tube A was prepared by mixing 20 μg DNA (e.g., pCMV vector; pCMV vector AP-1 cDNA, etc.) in 1.2 ml serum free DMEM (Irvine Scientific, Irvine, Calif.); tube B was prepared by mixing 120 μl lipofectamine (Gibco BRL) in 1.2 ml serum free DMEM. Tubes A and B were then admixed by inversions (several times), followed by incubation at room temperature for 30–45 min. The admixture is referred to as the "transfection mixture". Plated 293 cells were washed with 1×PBS, followed by addition of 10 ml serum free DMEM. 2.4 ml of the transfection mixture was then added to the cells, followed by incubation for 4 hrs at 37° C./5% CO$_2$. On day 3, cells were trypsinized and counted, followed by plating of 1×10$^6$ cells/well (poly D-lysine treated 12-well plates). Cells were permitted to adhere to the wells, followed by one wash with 1×PBS. Thereafter, 0.5 μCi $^3$H-inositol in 1 ml inositol-free DMEM was added per well. Protocol B.

On day 4, the cells were washed with 0.5 ml PBS and then 0.45 ml of assay medium was added containing inositol-free/serum free media, 10 μM pargyline, 10 mM lithium chloride, or 0.4 ml of assay medium and 50 ul of 10× ketanserin (ket) to a final concentration of 10 μM. The cells were then incubated for 30 minutes at 37° C. Then the cells were washed with 0.5 ml PBS and 200 ul of fresh/ice cold stop solution (1M KOH; 18 mM Na-borate; 3.8 mM EDTA) was added/well. The solution was kept on ice for 5–10 minutes or until the cells were lysed and then neutralized by 200 μl of fresh/ice cold neutralization sol. (7.5% HCL). The lysate was then transferred into 1.5 ml microcentrifuge tubes and 1 ml of chloroform/methanol (1:2) was added/tube. The solution was vortexed for 15 seconds and the upper phase was applied to a Biorad AG1-X8 anion exchange resin (100–200 mesh). The resin was washed with water and 0.9 ml of the upper phase was loaded onto the column. The column was washed with 10 mls of 5 mM myo-inositol and 10 ml of 5 mM Na-borate/60 mM Na-formate. The inositol trisphosphates were eluted into scintillation vials containing 10 ml of scintillation cocktail with 2 ml of 0.1 M formic acid/1 M ammonium formate. The columns were regenerated by washing with 10 ml of 0.1 M formic acid/3M ammonium formate and rinsed twice with dd H$_2$O and stored at room temperature in water. Results are discussed below.

Example 7

Screening of Candidate Compounds Against Non-Endogenous, Constitutively Activated Human Serotonin Receptors: AP-1

Approximately 5,500 candidate compounds (Tripos, Inc., St. Louis, Mo.) were screened using the assay protocol of Example 3 (with AP-1 mutant receptor) for identification as inverse agonists against the receptor; for this assay, an arbitrary cut-off of at least 50% inhibition was established for identification of inverse agonists. Approximately 120 of these compounds evidenced at least 50% inhibition of [$^{35}$S]GTPγS binding at 10 μM candidate compound (data not shown).

Example 8

Screening of Selected Compounds to Confirm Receptor Binding: AP-1

The candidate compounds identified from Example 7 were then screened using the assay protocol of Example 4 (mesulergine), using the AP-1 mutant receptor. $IC_{50}$ (nM) values were determined; five of the nearly 120 compounds of Example 7 were determined to have potent binding affinity for the receptor. Results are summarized in Table 4.

TABLE 4

| Candidate Compound | $IC_{50}$ (nM) in Mesulergine Assay |
|---|---|
| 102461 | 205.0 |
| 102788 | 46.5 |
| 100341 | 209.0 |
| 100431 | 147.0 |
| 103487 | 1,810.0 |

Example 9a

General Screening Paradigm: Selection of Pre-Clinical Candidate Leads

The "primary" screen designed to directly identify human $5HT_{2A}/5HT_{2C}$ receptor inverse agonists consisted of a membrane-based GTPγS binding assay utilizing membranes prepared from COS7 cells transiently transfected with AP-1 human receptor. Candidate compounds (10 μM final assay concentration) directly identified as inhibiting receptor-mediated increases in GTPγS binding by greater than 50–75% (arbitrary cut-off value) were considered active "hits". Primary assay hits were then re-tested in the same assay to reconfirm their inverse agonist activity. If primary assay hits were reconfirmed active (50% or greater inhibition), and therefore directly identified as, e.g., an inverse agonist, one of two approaches were available: (a) so-called "directed libraries" could be created, i.e., additional candidate compounds were synthesized based upon the structures of the reconfirmed hits (geared towards, e.g., improvement in the characteristics of the compounds) whereby the directed library compounds were then evaluated for the ability to compete for radioligand binding to both mutant $5HT_{2C}$ (AP-1) and endogenous $5HT_{2A}$ receptors, or (b) the reconfirmed hits were then evaluated for the ability to compete for radioligand binding to both mutant $5HT_{2C}$ (AP-1) and endogenous $5HT_{2A}$ receptors. Thus, when approach (a) was used, because these directed library candidate compounds were based upon the structures of compounds that were directly identified from the membrane-based GTPγS binding assay, the directed library compounds were not re-tested in the membrane-based GTPγS binding assay but rather were then confirmed via the radioligand binding analysis. The radioligand binding analysis tests were initially performed at 10 μM test compound in triplicate and if the compound inhibited radiolabeled binding by 50% or more, the analysis was followed by eight concentration competition curves to determine Ki values. The last step in secondary assay evaluation was to determine if test compounds were capable of inhibiting AP-3 receptor-mediated accumulation of inositol phosphates (e.g., $IP_3$). This final assay confirms that the directly identified compounds retained inverse agonist properties.

Example 9b

Constitutively Activated Human $5HT_{2C}$ Receptor (AP-1) Mediated Facilitation of GTPγS Binding to COS7 Membranes This protocol is substantially the same as set forth above in Example 6.

Primary screening assays measuring GTPγS binding to membranes prepared from COS7 cells transiently transfected with human mutated $5HT_{2C}$ receptor (AP-1) were used to directly identify inverse agonists in screening libraries (Tripos, Inc.). Candidate compound screens were performed in a total assay volume of 200 μl using scintillant-coated Wallac Scintistrip™ plates. The primary assay was comprised of the following chemicals (at indicated final assay concentrations): 20 mM HEPES, pH 7.4, 100 mM NaCl, 20 mM $MgCl_2$, 0.2% saponin, 0.2 mM ascorbic acid, 1 μM GDP, 0.3 nM GTPγ$^{35}$S, and 12.5 μg of the above defined membranes. Incubations were performed for 60 minutes at ambient room temperature. The binding assay incubation was terminated by centrifugation of assay plates at 4,000 rpm for 15 minutes, followed by rapid aspiration of the reaction mixture and counting in a Wallac MicroBeta™ scintillation counter.

Primary screening of candidate compounds initially involved testing of 72 test compounds per assay plate (96-well plates were utilized), at a final assay concentration of 10 μM candidate compound, in single replicates. A total of sixteen wells of each plate were dedicated for an eight concentration clozapine (a confirmed $5HT_{2C/2A}$ inverse agonist) dose response curve (duplicate determinations at each concentration). Finally, a total of five assay wells of each plate were dedicated to define the negative control (AP-1 receptor expressing membranes without addition of candidate compounds) and three wells from each plate to define the positive control (membranes without AP-1 receptor).

Reconfirmation experiments involve re-testing candidate compounds in the same assay described above, except that candidate compounds were evaluated in triplicate, thus allowing evaluation of 24 compounds per 96-well assay plate. Similar to the primary assay plates, an eight concentration clozapine dose response curve (duplicate determinations at each concentration) and the same negative and positive control wells were also included within each 96-well plate.

Example 9c(1)

Competition Studies for Directly Identified Compounds: Mutated Human $5HT_{2C}$ Receptor (AP-1)

Radioligand binding competition experiments were performed in a total assay volume of 200 μl using standard 96-well microtiter plates. The final assay ingredients consisted of assay buffer (20 mM HEPES and 10 mM $MgCl_2$), 1 nM [$^3$H]mesulergine, and 50 μg of membranes (COS7 with AP-1 as defined above). Nonspecific [$^3$H]mesulergine binding was defined in the presence of 100 μM mianserin. Incubations were performed for 1 hour at 37° C. Receptor bound radioligand was resolved from free radioligand by rapid filtration of the assay mixture over a Wallac Filtermat™ Type B filter, followed by washing with ice-cold assay buffer using a Skatron™ cell harvester. Radioactivity was counted using a Wallac 1205 BetaPlate™ counter. Each assay plate contained five negative control wells (membranes expressing receptor and no candidate compound addition) and three positive control wells (each containing 100 μM mianserin). For one concentration tests, candidate compounds were diluted into assay buffer and screened at a final concentration of 10 μM, in triplicate. For $IC_{50}$ determinations, candidate compounds were diluted in assay buffer and eight different concentrations were evaluated, in triplicate. A total of 16 wells were designated for an eight concentration mianserin dose response curve evaluation for both assays.

Example 9c(2)

Competition Studies Wild Type Human $5HT_{2A}$ Receptor

Radioligand binding competition experiments were performed in a total assay volume of 200 µl using standard 96-well microtiter plates. The final assay ingredients comprised assay buffer (20 mM HEPES and 10 mM $MgCl_2$), 1 nM [$^3$H]LSD, and 50 µg of the above-defined membranes (COS7 with AP-1). Nonspecific [$^3$H]LSD binding was defined in the presence of 100 µM serotonin. Incubations were performed for 1 hour at 37° C. Receptor bound radioligand was resolved from free radioligand by rapid filtration of the assay mixture over a Wallac Filtermat™ Type B filter, followed by washing with ice-cold assay buffer using a Skatron™ cell harvester. Radioactivity was counted using a Wallac 1205 BetaPlate™ counter. Each assay plate contained five negative control wells (membranes expressing receptor and no candidate compound addition) and three positive control wells (containing 100 µM mianserin). For one concentration tests, candidate compounds were diluted into assay buffer and screened at a final concentration of 10 µM in triplicate. For $IC_{50}$ determinations, candidate compounds were diluted in assay buffer and eight different concentrations were evaluated in triplicate. A total of 16 wells were designated for an eight concentration serotonin dose response curve evaluation for both assays.

Example 9d

Receptor-Mediated Inositol Phosphate Accumulation

Candidate compound identified in the assays of Examples 9a–9c were then evaluated for inositol phosphate accumulation, following the protocol of Example 5 (COS7 cells expressing human mutated $5HT_{2A}$ receptor, AP-3), modified as follows: tube A was prepared by mixing 16 µg DNA (e.g., pCMV vector; pCMV vector AP-1 cDNA, etc.) in 1.0 ml serum free DMEM (Irvine Scientific, Irvine, Calif.); tube B was prepared by mixing 60 µl lipofectamine (Gibco BRL) in 1.0 ml serum free DMEM. Tubes A and B were then admixed by inversions (several times), followed by incubation at room temperature for 30 min. The admixture is referred to as the "transfection mixture". Plated 293 cells were washed with 10 ml Serum Free DMEM, followed by addition of 11 ml Serum Free DMEM. 2.0 ml of the transfection mixture was then added to the cells, followed by incubation for 5 hrs at 37° C./5% $CO_2$. On day 3, cells were trypsinized and counted, followed by plating of $1 \times 10^6$ cells/well (12-well plates). Cells were permitted to adhere to the wells for 8 hrs, followed by one wash with 1xPBS. Thereafter, 0.5 µCi $^3$H-inositol in 1 ml inositol-free DMEM was added per well.

On day 4, the cells were washed with 1.5 ml PBS and then 0.9 ml of assay medium was added containing inositol-free/serum free media, 10 µM pargyline, 10 mM lithium chloride, for 5 min in 37° C./5% $CO_2$ followed by 100 µl addition of candidate compound diluted in the same material. The cells were then incubated for 120 minutes at 37° C. Then the cells were washed with 1.5 ml PBS and 200 µl of fresh/icecold stop solution (1M KOH; 18 mM Na-borate; 3.8 mM EDTA) was added/well. The solution was kept on ice for 5–10 minutes or until the cells were lysed and then neutralized by 200 µl of fresh/ice cold neutralization sol. (7.5% HCL). The lysate was then transferred into 1.5 ml micro-centrifuge tubes and 1 ml of chloroform/methanol (1:2) was added/tube. The solution was vortexed for 15 seconds and the upper phase was applied to a Biorad AG1-X8 anion exchange resin (100–200 mesh). The resin was washed with water and 0.9 ml of the upper phase was loaded onto the column. The column was washed with 10 mls of 5 mM myo-inositol and 10 ml of 5 mM Na-borate/60 mM Na-formate. The inositol trisphosphates were eluted into scintillation vials containing 10 ml of scintillation cocktail with 2 ml of 0.1 M formic acid/1 M ammonium formate. The columns were regenerated by washing with 10 ml of 0.1 M formic acid/3M ammonium formate and rinsed twice with dd $H_2O$ and stored at room temperature in water.

Following this round of assaying, candidate compounds having an $IC_{50}$ value of less than 10 µM were considered as potential leads for the development of pharmaceutical compositions.

Example 10

Screening Candidate Compounds

Following the protocols set forth above, one compound, 103487 (Example 8, supra) evidenced the following results:

| Compound No. | GTPγS AP-1 Percent Inhibition Relative To Positive Control (Primary) | GTPγS AP-1 Percent Inhibition Relative To Positive Control (Reconfirm) | Competitive Binding AP-1 ([$^3$H]mesulergine) $IC_{50}$ Value (nM) | Competitive Binding WT 5HT2A ([$^3$H]LSD) $IC_{50}$ Value (nM) | Inositol Phosphate Accumulation AP-3 $IC_{50}$ Value (nM) |
|---|---|---|---|---|---|
| 103487 | −1% | 31% | 2100<br>850 | 46 | 52<br>90 |

Based upon these results, structure activity analysis of the 103487 compound suggested that a series of derivatives of 3-(4-bromo-1-methylpyrazole-3-yl)phenylamine would exhibit similar $5\text{-HT}_{2A}$ activity and selectivity. A series of derivatives of 3-(4-bromo-1-methylpyrazole-3-yl) phenylamine were synthesized. These "directed" library compounds (Tripos, Inc.) were then analyzed in accordance with the protocols of Examples 9c(1), 9c(2) and 9d.

A preferred series of compounds possessing $5\text{-HT}_{2A}$ receptor activity that are useful as inverse agonists at such receptors is designated by the general Formula (A):

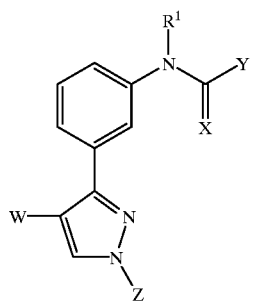

(A)

wherein:
W is F, Cl, Br, I, $C_{1-8}$ straight chain or branched alkyl, $C_{3-8}$ cycloalkyl, $C_{4-9}$ alkylcycloalkyl, or $C_{2-8}$ alkenyl;

X is O or S or $NR^2$;

Y is $NR^3R^4$, or $(CH_2)_mR^5$, or $O(CH_2)_nR^6$ m is an integer between 0 and 4, inclusive;

n is an integer between 0 and 4, inclusive;

Z is H, $C_{1-8}$ straight chain or branched alkyl, $C_{3-8}$ cycloalkyl, $C_{4-9}$ alkylcycloalkyl, or $C_{2-8}$ alkenyl;

$R^1$, $R^2$, $R^3$ and $R^{10}$ are each independently selected from: H, $C_{1-8}$ straight chain or branched alkyl, $C_{3-8}$ cycloalkyl, $C_{4-9}$ alkylcycloalkyl, or $C_{2-8}$ alkenyl;

$R^4$, $R^5$, and $R^6$ is each independently selected from: $C_{1-8}$ straight chain or branched alkyl, $C_{2-8}$ alkenyl or cycloalkyl, or alkylcycloalkyl, or aryl, or $CH_2$aryl, wherein each moiety within said $C_{1-8}$ straight chain or branched alkyl, $C_{2-8}$ alkenyl or cycloalkyl, or alkylcycloalkyl, or aryl or $CH_2$aryl may be optionally substituted by up to four substituents in any position, whereby each substituent is independently selected from: H, F, Cl, Br, I, $R^7$, $CF_3$, $CF_2R^7$, $CF_2CF_2$, $CCl_3$, $CCl_2R^7$, $CCl_2CCl_2R^7$, $NR^8R^9$, $NR^{10}COR^7$, $NR^{10}SO_2R^7$, $OR^7$, $OCF_3$, $OCF_2R^7$, $OCF_2CF_2R^7$, $OCOR^7$, $OSO_2R^7$, $OPO(OR^7)_2$, $SR^7$, $SCF_3$, $SCF_2R^7$, $SCF_2CF_2R^7$, $SCOR^7$, $SO_3R^7$, $SO_2NR^8R^9$, $PO(OR^7)_3$, $PO(OR^7)_2R^7$, $NO_2$, CN, $CNR^{10}(NR^8R^9)$, $CNR^{10}(SR^7)$, $COOR^7$, $COSR^7$, $CONR^8R^9$, with the proviso that when $R^4$, $R^5$, or $R^6$ contains an aryl ring substituted at at least two adjacent positions on said aryl ring, then said two adjacent positions can together be selected from $SCH_2S$, $SCH_2CH_2S$, $OCH_2O$, or $OCH_2CH_2O$ to form a bi-cyclic structure;

$R^7$ is H, $C_{1-8}$ straight chain or branched alkyl, $C_{3-8}$ cycloalkyl, $C_{4-9}$ alkylcycloalkyl, $C_{2-8}$ alkenyl, aryl or alkylaryl; and $R^8$ and $R^9$ are each independently selected from H, $C_{1-8}$ straight chain or branched alkyl, $C_{2-8}$ alkenyl or cycloalkyl, or alkylcycloalkyl, or aryl, or $CH_2$aryl, wherein each moiety within said $C_{1-8}$ straight chain or branched alkyl, $C_{2-8}$ alkenyl or cycloalkyl, or alkylcycloalkyl, or aryl or $CH_2$aryl may be optionally substituted by up to four substituents in any position, whereby each substituent is independently selected from: F, Cl, Br, I, $CF_3$, $CCl_3$, $CH_3$, $C_2H_5$, $C_3H_7$, $C_4H_9$, $NH_2$, $NHCH_3$, $N(CH_3)_2$, $NHC_2H_5$, $N(C_2H_5)_2$, $NHC_3H_7$, $N(C_3H_7)_2$, $NHC_4H_9$, $N(C_4H_9)_2$, NHCOH, $NHCOCH_3$, $NHCOC_2H_5$, $NHCOC_3H_7$, $NHCOC_4H_9$, $NHSO_2CH_3$, $NHSO_2C_2H_5$, $NHSO_2C_3H_7$, $NHSO_2C_4H_9$, OH, $OCH_3$, $OC_2H_5$, $OC_3H_7$, $OC_4H_7$, $OC_4H_9$, $OC_5H_9$, $OC_5H_{11}$, $OC_6H_{11}$, $OC_6H_{13}$, $OCF_3$, $OCOCH_3$, $OCOC_2H_5$, $OCOC_3H_7$, $OCOC_4H_9$, $OSO_2CH_3$, $OSO_2C_2H_5$, $OSO_2C_3H_7$, $OSO_2C_4H_9$, SH, $SCH_3$, $SC_2H_5$, $SC_3H_7$, $SC_4H_7$, $SC_4H_9$, $SC_5H_9$, $SC_5H_{11}$, $SC_6H_{11}$, $SC_6H_{13}$,, $SCF_3$, $SCOCH_3$, $SCOC_2H_5$, $SCOC_3H_7$, $SCOC_4H_9$, $SO_3CH_3$, $SO_3C_2H_5$, $SO_3C_3H_7$, $SO_3C_4H_9$, $SO_2NH$, $SO_2NH_2$, $SO_2NHCH_3$, $SO_2N(CH_3)_2$, $SO_2NHC_2H_5$, $SO_2N(C_2H_5)_2$, $SO_2NHC_3H_7$, $SO_2N(C_3H_7)_2$, $SO_2NHC_4H_9$, $SO_2N(C_4H_9)_2$, $NO_2$, CN, $COOCH_3$, $COOC_2H_5$, $COOC_3H_7$, $COOC_4H_9$, $COSCH_3$, $COSC_2H_5$, $COSC_3H_7$, $COSC_4H_9$, $CONH_2$, $CONHCH_3$, $CON(CH_3)_2$, $CONHC_2H_5$, $CON(C_2H_5)_2$, $CONHC_3H_7$, $CON(C_3H_7)_2$, $CONHC_4H_9$, $CON(C_4H_9)_2$, and with the proviso that when either or both of $R^8$ or $R^9$ contain an aryl ring substituted at at least two adjacent positions on said aryl ring, then said two adjacent positions can together be selected from $SCH_2S$, $SCH_2CH_2S$, $OCH_2O$, or $OCH_2CH_2O$ to form a bi-cyclic structure;

or $R^8$ and $R^9$ may together form part of a 5, 6 or 7 membered cyclic structure, with said structure being saturated or unsaturated, and further with said structure containing up to four heteroatoms selected from O, N or S, and further wherein each moiety within said cyclic structure being optionally substituted by up to four substituents in any position independently selected from: F, Cl, Br, I, $CF_3$, $CCl_3$, $CH_3$, $C_2H_5$, $C_3H_7$, $C_4H_9$, $NH_2$, $NHCH_3$, $N(CH_3)_2$, $NHC_2H_5$, $N(C_2H_5)_2$, $NHC_3H_7$, $N(C_3H_7)_2$, $NHC_4H_9$, $N(C_4H_9)_2$, NHCOH, $NHCOCH_3$, $NHCOC_2H_5$, $NHCOC_3H_7$, $NHCOC_4H_9$, $NHSO_2CH_3$, $NHSO_2C_2H_5$, $NHSO_2C_3H_7$, $NHSO_2C_4H_9$, OH, $OCH_3$, $OC_2H_5$, $OC_3H_7$, $OC_4H_7$, $OC_4H_9$, $OC_5H_9$, $OC_5H_{11}$, $OC_6H_{11}$, $OC_6H_{13}$, $OCF_3$, $OCOCH_3$, $OCOC_2H_5$, $OCOC_3H_7$, $OCOC_4H_9$, $OSO_2CH_3$, $OSO_2C_2H_5$, $OSO_2C_3H_7$, $OSO_2C_4H_9$, SH, $SCH_3$, $SC_2H_5$, $SC_3H_7$, $SC_4H_7$, $SC_4H_9$, $SC_5H_9$, $SC_5H_{11}$, $SC_6H_{11}$, $SC_6H_{13}$,, $SCF_3$, $SCOCH_3$, $SCOC_2H_5$, $SCOC_3H_7$, $SCOC_4H_9$, $SO_3CH_3$, $SO_3C_2H_5$, $SO_3C_3H_7$, $SO_3C_4H_9$, $SO_2NH$, $SO_2NH_2$, $SO_2NHCH_3$, $SO_2N(CH_3)_2$, $SO_2NHC_2H_5$, $SO_2N(C_2H_5)_2$, $SO_2NHC_3H_7$, $SO_2N(C_3H_7)_2$, $SO_2NHC_4H_9$, $SO_2N(C_4H_9)_2$, $NO_2$, CN, $COOCH_3$, $COOC_2H_5$, $COOC_3H_7$, $COOC_4H_9$, $COSCH_3$, $COSC_2H_5$, $COSC_3H_7$, $COSC_4H_9$, $CONH_2$, $CONHCH_3$, $CON(CH_3)_2$, $CONHC_2H_5$, $CON(C_2H_5)_2$, $CONHC_3H_7$, $CON(C_3H_7)_2$, $CONHC_4H_9$, $CON(C_4H_9)_2$, and with the proviso that wherein when $R^8$ and $R^9$ form an aryl ring substituted at at least two adjacent positions on said aryl ring, then said two adjacent positions can together be selected from $SCH_2S$, $SCH_2CH_2S$, $OCH_2O$, or $OCH_2CH_2O$ to form a bi-cyclic structure.

An aryl moiety can be a 5 or 6 membered aromatic heterocyclic ring (containing up to 4 hetero atoms independently selected from N, O, or S) or a 6 membered aromatic non-heterocyclic ring or a polycycle;

Examples of suitable $C_{1-8}$ alkyl groups include but are not limited to methyl, ethyl, n-propyl, i-propyl, n-butyl, and t-butyl.

Examples of 5 or 6 membered ring moieties include, but are not restricted to, phenyl, furanyl, thienyl, imidazolyl, pyridyl, pyrrolyl, oxazolyl, isoxazolyl, triazolyl, pyrazolyl, tetrazolyl, thiazolyl, and isothiazolyl. Examples of polycycle moieties include, but are not restricted to, naphthyl, benzothiazolyl, benzofuranyl, benzimidazolyl, quinolyl, isoquinolyl, indolyl, quinoxalinyl, quinazolinyl, and benzothienyl.

Preferred compounds falling within the scope of general Formula (A) as Class (1) compounds where Y=$NR^3R^4$ are as follows:

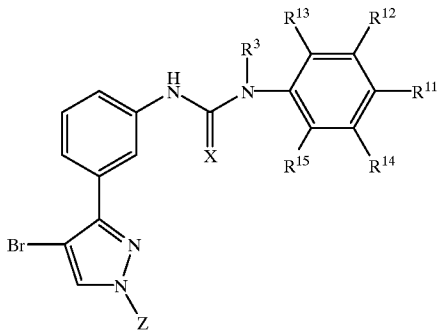

(1)

wherein:
X is O or S or $NR^2$;
Z is H or $CH_3$;
$R^2$, $R^3$ and $R^{10}$ are each independently selected from H, $C_{1-8}$ straight chain or branched alkyl, $C_{3-8}$ cycloalkyl, $C_{4-9}$ alkylcycloalkyl, or $C_{2-8}$ alkenyl;
$R^{11}$ is H, F, Cl, Br, I, $R^7$, $CF_3$, $CF_2R^7$, $CF_2CF_2$, $CCl_3$, $CCl_2R^7$, $CCl_2CCl_2R^7$, $NR^8R^9$, $NR^{10}COR^7$, $NR^{10}SO_2R^7$, $OR^7$, $OCF_3$, $OCF_2R^7$, $OCF_2CF_2R^7$, $OCOR^7$, $OSO_2R^7$, $OPO(OR^7)_2$, $SR^7$, $SCF_3$, $SCF_2R^7$, $SCF_2CF_2R^7$, $SCOR^7$, $SO_3R^7$, $SO_2NR^8R^9$, $PO(OR^7)_3$, $PO(OR^7)_2R^7$, $NO_2$, CN, $CNR^{10}(NR^8R^9)$, $CNR^{10}(SR^7)$, $COOR^7$, $COSR^7$, $CONR^8R^9$, with the proviso that when a position adjacent to $R^{11}$ is substituted, then $R^{11}$ and said adjacent position can together be selected from $SCH_2S$, $SCH_2CH_2S$, $OCH_2O$, or $OCH_2CH_2O$ to form a bi-cyclic structure;

$R^7$ is H, $C_{1-8}$ straight chain or branched alkyl, $C_{3-8}$ cycloalkyl, $C_{4-9}$ alkylcycloalkyl, $C_{2-8}$ alkenyl, aryl or alkylaryl;

$R^8$ and $R^9$ are each independently selected from: H, $C_{1-8}$ straight chain or branched alkyl, $C_{2-8}$ alkenyl or cycloalkyl, or alkylcycloalkyl, or aryl or $CH_2$aryl wherein each moiety within said $C_{1-8}$ straight chain or branched alkyl, $C_{2-8}$ alkenyl or cycloalkyl, or alkylcycloalkyl, or aryl or $CH_2$aryl may be optionally substituted by up to four substituents in any position, whereby each substituent is independently selected from: F, Cl, Br, I, $CF_3$, $CCl_3$, $CH_3$, $C_2H_5$, $C_3H_7$, $C_4H_9$, $NH_2$, $NHCH_3$, $N(CH_3)_2$, $NHC_2H_5$, $N(C_2H_5)_2$, $NHC_3H_7$, $N(C_3H_7)_2$, $NHC_4H_9$, $N(C_4H_9)_2$, NHCOH, $NHCOCH_3$, $NHCOC_2H_5$, $NHCOC_3H_7$, $NHCOC_4H_9$, $NHSO_2CH_3$, $NHSO_2C_2H_5$, $NHSO_2C_3H_7$, $NHSO_2C_4H_9$, OH, $OCH_3$, $OC_2H_5$, $OC_3H_7$, $OC_4H_7$, $OC_4H_9$, $OC_5H_9$, $OC_5H_{11}$, $OC_6H_{11}$, $OC_6H_{13}$, $OCF_3$, $OCOCH_3$, $OCOC_2H_5$, $OCOC_3H_7$, $OCOC_4H_9$, $OSO_2CH_3$, $OSO_2C_2H_5$, $OSO_2C_3H_7$, $OSO_2C_4H_9$, SH, $SCH_3$, $SC_2H_5$, $SC_3H_7$, $SC_4H_7$, $SC_4H_9$, $SC_5H_9$, $SC_5H_{11}$, $SC_6H_{11}$, $SC_6H_{13}$, $SCF_3$, $SCOCH_3$, $SCOC_2H_5$, $SCOC_3H_7$, $SCOC_4H_9$, $SO_3CH_3$, $SO_3C_2H_5$, $SO_3C_3H_7$, $SO_3C_4H_9$, $SO_2NH$, $SO_2NH_2$, $SO_2NHCH_3$, $SO_2N(CH_3)_2$, $SO_2NHC_2H_5$, $SO_2N(C_2H_5)_2$, S $O_2NHC_3H_7$, $SO_2N(C_3H_7)_2$, $SO_2NHC_4H_9$, $SO_2N(C_4H_9)_2$, $NO_2$, CN, $COOCH_3$, $COOC_2H_5$, $COOC_3H_7$, $COOC_4H_9$, $COSCH_3$, $COSC_2H_5$, $COSC_3H_7$, $COSC_4H_9$, $CONH_2$, $CONHCH_3$, $CON(CH_3)_2$, $CONHC_2H_5$, $CON(C_2H_5)_2$, $CONHC_3H_7$, $CON(C_3H_7)_2$, $CONHC_4H_9$, $CON(C_4H_9)_2$, with the proviso that when either of $R^8$ or $R^9$ contain an aryl ring substituted at at least two adjacent positions on said aryl ring, then said two adjacent positions can together be selected from $SCH_2S$, $SCH_2CH_2S$, $OCH_2O$, or $OCH_2CH_2O$ to form a bi-cyclic structure;

$R^{12}$, $R^{13}$, $R^{14}$, and $R^{15}$ are each independently selected from the following: F, Cl, Br, I, $CF_3$, $CCl_3$, $CH_3$, $C_2H_5$, $C_3H_7$, $C_4H_9$, $NH_2$, $NHCH_3$, $N(CH_3)_2$, $NHC_2H_5$, $N(C_2H_5)_2$, $NHC_3H_7$, $N(C_3H_7)_2$, $NHC_4H_9$, $N(C_4H_9)_2$, NHCOH, $NHCOCH_3$, $NHCOC_2H_5$, $NHCOC_3H_7$, $NHCOC_4H_9$, $NHSO_2CH_3$, $NHSO_2C_2H_5$, $NHSO_2C_3H_7$, $NHSO_2C_4H_9$, OH, $OCH_3$, $OC_2H_5$, $OC_3H_7$, $OC_4H_7$, $OC_4H_9$, $OC_5H_9$, $OC_5H_{11}$, $OC_6H_{11}$, $OC_6H_{13}$, $OCF_3$, $OCOCH_3$, $OCOC_2H_5$, $OCOC_3H_7$, $OCOC_4H_9$, $OSO_2CH_3$, $OSO_2C_2H_5$, $OSO_2C_3H_7$, $OSO_2C_4H_9$, SH, $SCH_3$, $SC_2H_5$, $SC_3H_7$, $SC_4H_7$, $SC_4H_9$, $SC_5H_9$, $SC_5H_{11}$, $SC_6H_{11}$, $SC_6H_{13}$, $SCF_3$, $SCOCH_3$, $SCOC_2H_5$, $SCOC_3H_7$, $SCOC_4H_9$, $SO_3CH_3$, $SO_3C_2H_5$, $SO_3C_3H_7$, $SO_3C_4H_9$, $SO_2NH$, $SO_2NH_2$, $SO_2NHCH_3$, $SO_2N(CH_3)_2$, $SO_2NHC_2H_5$, $SO_2N(C_2H_5)_2$, $SO_2NHC_3H_7$, $SO_2N(C_3H_7)_2$, $SO_2NHC_4H_9$, $SO_2N(C_4H_9)_2$, $NO_2$, CN, $COOCH_3$, $COOC_2H_5$, $COOC_3H_7$, $COOC_4H_9$, $COSCH_3$, $COSC_2H_5$, $COSC_3H_7$, $COSC_4H_9$, $CONH_2$, $CONHCH_3$, $CON(CH_3)_2$, $CONHC_2H_5$, $CON(C_2H_5)_2$, $CONHC_3H_7$, $CON(C_3H_7)_2$, $CONHC_4H_9$, $CON(C_4H_9)_2$, and with the proviso that when any two adjacent positions of $R^{12}$, $R^{13}$, $R^{14}$, and $R^{15}$ are substituted, said two adjacent positions can together be further selected from $SCH_2S$, $SCH_2CH_2S$, $OCH_2O$, or $OCH_2CH_2O$ to form a bi-cyclic structure; and with the proviso that at least one of $R^{12}$, $R^{13}$, $R^{14}$, and $R^{15}$ must be H.

More preferred compounds falling within the scope of Class (1) compounds are defined as follows:

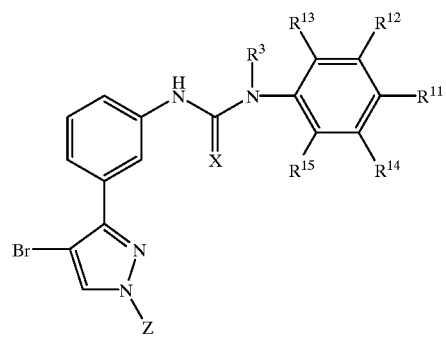

wherein:
X is O or S;
Z is H or $CH_3$;
$R^3$ and $R^{10}$ are each independently selected from H, $C_{1-8}$ straight chain or branched alkyl, $C_{3-8}$ cycloalkyl, $C_{4-9}$ alkylcycloalkyl, or $C_{2-8}$ alkenyl;
$R^{11}$ is H, F, Cl, Br, I, $R^7$, $CF_3$, $CCl_3$, $NR^8R^9$, $NR^{10}COR^7$, $NR^{10}SO_2R^7$, $OR^7$, $OCF_3$, $OCOR^7$, $OSO_2R^7$, $SR^7$, $SCF_3$, $SCOR^7$, $SO_3R^7$, $SO_2NR^8R^9$, $NO_2$, CN, $COOR^7$, $COSR^7$, $CONR^8R^9$, with the proviso that when a position adjacent to $R^{11}$ is substituted, then $R^{11}$ and said adjacent position can together be selected from $SCH_2S$, $SCH_2CH_2S$, $OCH_2O$, or $OCH_2CH_2O$ to form a bi-cyclic structure;

$R^7$ is H, $C_{1-8}$ straight chain or branched alkyl, $C_{3-8}$ cycloalkyl, $C_{4-9}$ alkylcycloalkyl, $C_{2-8}$ alkenyl, aryl or alkylaryl;

$R^8$ and $R^9$ are independently selected from H, $C_{1-8}$ straight chain or branched alkyl, $C_{2-8}$ alkenyl or cycloalkyl, or alkylcycloalkyl, or aryl or $CH_2$aryl wherein each moiety within said $C_{1-8}$ straight chain or branched alkyl, $C_{2-8}$ alkenyl or cycloalkyl, or alkylcycloalkyl, or aryl or $CH_2$aryl may be optionally substituted by up to four substituents in any position, whereby each substituent is independently selected from: F, Cl, Br, I, $CF_3$, $CCl_3$, $CH_3$, $C_2H_5$, $C_3H_7$, $C_4H_9$, $NH_2$, $NHCH_3$, $N(CH_3)_2$, $NHC_2H_5$, $N(C_2H_5)_2$, NHC$_3$H$_7$, N(C$_3$H$_7$)$_2$, NHC$_4$H$_9$, N(C$_4$H$_9$)$_2$, NHCOH, NHCOCH$_3$, NHCOC$_2$H$_5$, NHCOC$_3$H$_7$, NHCOC$_4$H$_9$, NHSO$_2$CH$_3$, NHSO$_2$C$_2$H$_5$, NHSO$_2$C$_3$H$_7$, NHSO$_2$C$_4$H$_9$, OH, OCH$_3$, OC$_2$H$_5$, OC$_3$H$_7$, OC$_4$H$_7$, OC$_4$H$_9$, OC$_5$H$_9$, OC$_5$H$_{11}$, OC$_6$H$_{11}$, OC$_6$H$_{13}$, OCF$_3$, OCOCH$_3$, OCOC$_2$H$_5$, OCOC$_3$H$_7$, OCOC$_4$H$_9$, OSO$_2$CH$_3$, OSO$_2$C$_2$H$_5$, OSO$_2$C$_3$H$_7$, OSO$_2$C$_4$H$_9$, SH, SCH$_3$, SC$_2$H$_5$, SC$_3$H$_7$, SC$_4$H$_7$, SC$_4$H$_9$, SC$_5$H$_9$, SC$_5$H$_{11}$, SC$_6$H$_{11}$, SC$_6$H$_{13}$,, SCF$_3$, SCOCH$_3$, SCOC$_2$H$_5$, SCOC$_3$H$_7$, SCOC$_4$H$_9$, SO$_3$CH$_3$, SO$_3$C$_2$H$_5$, SO$_3$C$_3$H$_7$, SO$_3$C$_4$H$_9$, SO$_2$NH, SO$_2$NH$_2$, SO$_2$NHCH$_3$, SO$_2$N(CH$_3$)$_2$, SO$_2$NHC$_2$H$_5$, SO$_2$N(C$_2$H$_5$)$_2$, SO$_2$NHC$_3$H$_7$, SO$_2$N(C$_3$H$_7$)$_2$, SO$_2$NHC$_4$H$_9$, SO$_2$N(C$_4$H$_9$)$_2$, NO$_2$, CN, COOCH$_3$, COOC$_2$H$_5$, COOC$_3$H$_7$, COOC$_4$H$_9$, COSCH$_3$, COSC$_2$H$_5$, COSC$_3$H$_7$, COSC$_4$H$_9$, CONH$_2$, CONHCH$_3$, CON(CH$_3$)$_2$, CONHC$_2$H$_5$, CON(C$_2$H$_5$)$_2$, CONHC$_3$H$_7$, CON(C$_3$H$_7$)$_2$, CONHC$_4$H$_9$, CON(C$_4$H$_9$)$_2$, and with the proviso that when either of $R^8$ or $R^9$ contain an aryl ring substituted at at least two adjacent positions on said aryl ring, then said two adjacent positions can together be selected from SCH$_2$S, SCH$_2$CH$_2$S, OCH$_2$O, or OCH$_2$CH$_2$O to form a bi-cyclic structure;

$R^{12}$, $R^{13}$, $R^{14}$, and $R^{15}$ are each independently selected from: F, Cl, Br, I, CF$_3$, CCl$_3$, CH$_3$, C$_2$H$_5$, C$_3$H$_7$, C$_4$H$_9$, NH$_2$, NHCH$_3$, N(CH$_3$)$_2$, NHC$_2$H$_5$, N(C$_2$H$_5$)$_2$, NHC$_3$H$_7$, N(C$_3$H$_7$)$_2$, NHC$_4$H$_9$, N(C$_4$H$_9$)$_2$, NHCOH, NHCOCH$_3$, NHCOC$_2$H$_5$, NHCOC$_3$H$_7$, NHCOC$_4$H$_9$, NHSO$_2$CH$_3$, NHSO$_2$C$_2$H$_5$, NHSO$_2$C$_3$H$_7$, NHSO$_2$C$_4$H$_9$, OH, OCH$_3$, OC$_2$H$_5$, OC$_3$H$_7$, OC$_4$H$_7$, OC$_4$H$_9$, OC$_5$H$_9$, OC$_5$H$_{11}$, OC$_6$H$_{11}$, OC$_6$H$_{13}$, OCF$_3$, OCOCH$_3$, OCOC$_2$H$_5$, OCOC$_3$H$_7$, OCOC$_4$H$_9$, OSO$_2$CH$_3$, OSO$_2$C$_2$H$_5$, OSO$_2$C$_3$H$_7$, OSO$_2$C$_4$H$_9$, SH, SCH$_3$, SC$_2$H$_5$, SC$_3$H$_7$, SC$_4$H$_7$, SC$_4$H$_9$, SC$_5$H$_9$, SC$_5$H$_{11}$, SC$_6$H$_{11}$, SC$_6$H$_{13}$,, SCF$_3$, SCOCH$_3$, SCOC$_2$H$_5$, SCOC$_3$H$_7$, SCOC$_4$H$_9$, SO$_3$CH$_3$, SO$_3$C$_2$H$_5$, SO$_3$C$_3$H$_7$, SO$_3$C$_4$H$_9$, SO$_2$NH, SO$_2$NH$_2$, SO$_2$NHCH$_3$, SO$_2$N(CH$_3$)$_2$, SO$_2$NHC$_2$H$_5$, SO$_2$N(C$_2$H$_5$)$_2$, SO$_2$NHC$_3$H$_7$, SO$_2$N(C$_3$H$_7$)$_2$, SO$_2$NHC$_4$H$_9$, SO$_2$N(C$_4$H$_9$)$_2$, NO$_2$, CN, COOCH$_3$, COOC$_2$H$_5$, COOC$_3$H$_7$, COOC$_4$H$_9$, COSCH$_3$, COSC$_2$H$_5$, COSC$_3$H$_7$, COSC$_4$H$_9$, CONH$_2$, CONHCH$_3$, CON(CH$_3$)$_2$, CONHC$_2$H$_5$, CON(C$_2$H$_5$)$_2$, CONHC$_3$H$_7$, CON(C$_3$H$_7$)$_2$, CONHC$_4$H$_9$, CON(C$_4$H$_9$)$_2$, and with the proviso that when any two adjacent positions of $R^{12}$, $R^{13}$, $R^{14}$, and $R^{15}$ are substituted, said two adjacent positions can together be further selected from SCH$_2$S, SCH$_2$CH$_2$S, OCH$_2$O, or OCH$_2$CH$_2$O to form a bi-cyclic structure; and with the proviso that at least two of $R^{12}$, $R^{13}$, $R^{14}$, and $R^{15}$ must be H.

Exemplary compounds of general Formula (A), Class (1) are set forth below. Based upon in vivo data developed (as set forth below), Compounds 116081 and 116082 are particularly preferred.

Inositol phosphate accumulation assays evidence the activity of test compounds. Both single concentration percentages of control values and IC$_{50}$ determinations indicate activity. In the tables below the column legends have the following meanings:

IP$_3$ % Control: The values in this column reflect an IP Accumulation Assay where the test compounds were evaluated at one concentration of 10 μM. For these assays, the compound was diluted into inositol-free Dulbecco's Eagle Media containing 10 μM pargyline and 10 mM LiCl and tested at a final assay concentration of 10 μM, in triplicate. The percent control value was calculated based on the control in which no test compound was added.

IP$_3$ AP-3 IC$_{50}$ nM: The values in this column reflect an IP accumulation assay in which the test compound was evaluated at several different concentrations whereby an IC$_{50}$ could be determined. This column corresponds to the column appearing in the tables above which is labeled: Inositol Phosphate Accumulation, AP-3, IC$_{50}$ Value (μM).

WT 5HT$_{2A}$ LSD IC$_{50}$ nM: The values in this column reflect a competitive binding assay using LSD. This column corresponds to the column appearing in the tables above which is labeled: Competitive Binding, WT 5HT$_{2A}$, ([$^3$H] LSD), IC$_{50}$ Value (μM).

(Note: A "dash" in the table indicates that no value was determined.)

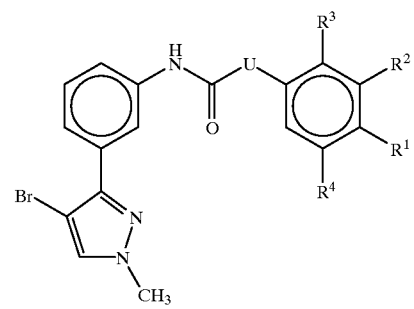

| Compound No. | $R^1$ | $R^2$ | $R^3$ | $R^4$ | X | U | IP$_3$ % of Control | IP$_3$ AP-3 IC$_{50}$ nM | WT 5HT$_{2A}$ LSD IC$_{50}$ nM |
|---|---|---|---|---|---|---|---|---|---|
| N-[3-(4-bromo-1-methylpyrazol-3-yl)phenyl][(4-methylthiophenyl)amino]carboxamide | | | | | | | | | |
| 116079 | SCH$_3$ | H | H | H | O | NH | 16 | 17 | 4 |
| N-[3-(4-bromo-1-methylpyrazol-3-yl)phenyl][(4-chlorophenyl)amino]carboxamide | | | | | | | | | |
| 116081 | Cl | H | H | H | O | NH | 10 | 3.2 | 11 |
| {[3-(4-bromo-1-methylpyrazol-3-yl)phenyl]amino}-N-(4-fluorophenyl)carboxamide | | | | | | | | | |
| 116082 | F | H | H | H | O | NH | 11 | — | 7 |

-continued

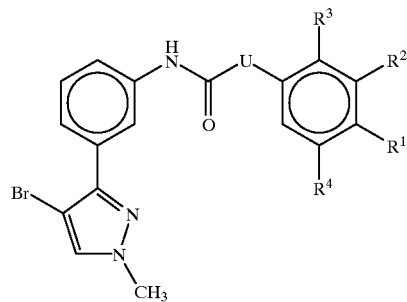

| Compound No. | R¹ | R² | R³ | R⁴ | X | U | IP$_3$ % of Control | IP$_3$ AP-3 IC$_{50}$ nM | WT 5HT$_{2A}$ LSD IC$_{50}$ nM |
|---|---|---|---|---|---|---|---|---|---|
| {[3-(4-bromo-1-methylpyrazol-3-yl)phenyl]amino}-N-[2-(trifluoromethoxy)phenyl]carboxamide | | | | | | | | | |
| 116087 | H | H | CF$_3$O | H | O | NH | 11 | — | 200 |
| {[3-(4-bromo-1-methylpyrazol-3-yl)phenyl]amino}-N-(2-nitrophenyl)carboxamide | | | | | | | | | |
| 116089 | H | H | NO$_2$ | H | O | NH | 27 | — | 238 |
| {[3-(4-bromo-1-methylpyrazol-3-yl)phenyl]amino}-N-(4-methoxyphenyl)carboxamide | | | | | | | | | |
| 116091 | MeO | H | H | H | O | NH | 12 | — | 19 |
| {[3-(4-bromo-1-methylpyrazol-3-yl)phenyl]amino}-N-(2-methylphenyl)carboxamide | | | | | | | | | |
| 116092 | H | H | Me | H | O | NH | 32 | — | 131 |
| {[3-(4-bromo-1-methylpyrazol-3-yl)phenyl]amino}-N-[4-(trifluoromethyl)phenyl]carboxamide | | | | | | | | | |
| 116097 | CF$_3$ | H | H | H | O | NH | 11 | — | 65 |
| {[3-(4-bromo-1-methylpyrazol-3-yl)phenyl]amino}-N-(3-chlorophenyl)carboxamide | | | | | | | | | |
| 116105 | H | Cl | H | H | O | NH | 11 | — | 39 |
| {[3-(4-bromo-1-methylpyrazol-3-yl)phenyl]amino}-N-(2-chlorophenyl)carboxamide | | | | | | | | | |
| 116108 | H | H | Cl | H | O | NH | 6 | — | 249 |
| {[3-(4-bromo-1-methylpyrazol-3-yl)phenyl]amino}-N-[4-(methylethyl)phenyl]carboxamide | | | | | | | | | |
| 116110 | isopropyl | H | H | H | O | NH | 7 | — | 338 |
| {[3-(4-bromo-1-methylpyrazol-3-yl)phenyl]amino}-N-(3-methoxyphenyl)carboxamide | | | | | | | | | |
| 116111 | H | MeO | H | H | O | NH | 7 | — | 106 |
| {[3-(4-bromo-1-methylpyrazol-3-yl)phenyl]amino}-N-(3-methylphenyl)carboxamide | | | | | | | | | |
| 116112 | H | Me | H | H | O | NH | 14 | — | 57 |
| [{3-(4-bromo-1-methylpyrazol-3-yl)phenyl}amino]-N-methyl-N-[4-(trifluoromethoxy)phenyl]carboxamide | | | | | | | | | |
| 116113 | CF$_3$O | H | H | H | O | NCH$_3$ | — | 193 | 2 |
| N-[4-(tert-butyl)phenyl]{[3-(4-bromo-1-methylpyrazol-3-yl)phenyl]amino}carboxamide | | | | | | | | | |
| 116119 | t-butyl | H | H | H | O | NH | 17 | — | 476 |
| N-[4-(dimethylamino)phenyl]{[3-(4-bromo-1-methylpyrazol-3-yl)phenyl]amino}carboxamide | | | | | | | | | |
| 116122 | NMe$_2$ | H | H | H | O | NH | 9 | — | 309 |
| N-(3,5-dichloro-4-methylphenyl){[3-(4-bromo-1-methylpyrazol-3-yl)phenyl]amino}carboxamide | | | | | | | | | |
| 116138 | Me | Cl | H | Cl | O | NH | 23 | — | 122 |
| {[3-(4-bromo-1-methylpyrazol-3-yl)phenyl]amino}-N-[4-(trifluoromethylthio)phenyl]carboxamide | | | | | | | | | |
| 116139 | CF$_3$S | H | H | H | O | NH | 12 | — | 56 |
| {[3-(4-bromo-1-methylpyrazol-3-yl)phenyl]amino}-N-(2-fluorophenyl)carboxamide | | | | | | | | | |
| 116144 | H | H | F | H | O | NH | 12 | — | 37 |
| 2-({[3-(4-bromo-1-methylpyrazol-3-yl)phenyl]amino}carbonylamino)benzamide | | | | | | | | | |
| 116145 | H | H | CONH$_2$ | H | O | NH | 31 | — | 7473 |
| {[3-(4-bromo-1-methylpyrazol-3-yl)phenyl]amino}-N-(4-cyanophenyl)carboxamide | | | | | | | | | |
| 116147 | CN | H | H | H | O | NH | 12 | — | 2 |
| {[3-(4-bromo-1-methylpyrazol-3-yl)phenyl]amino}-N-(2-cyanophenyl)carboxamide | | | | | | | | | |
| 116148 | H | H | CN | H | O | NH | 30 | — | 348 |

Additional compounds falling under the defined parameters of class (1) are as follows:

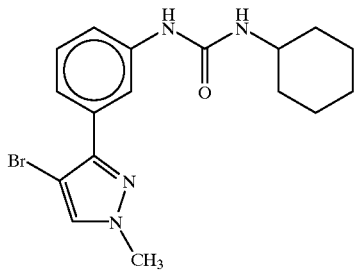

| Compound No. | IP$_3$ AP-3 IC$_{50}$ nM | WT 5HT$_{2A}$ LSD IC$_{50}$ nM |
|---|---|---|
| 116141 N-[3-(4-bromo-1-methylpyrazol-3-yl)phenyl][cyclohexylamino]carboxamide | 114 | 81 |

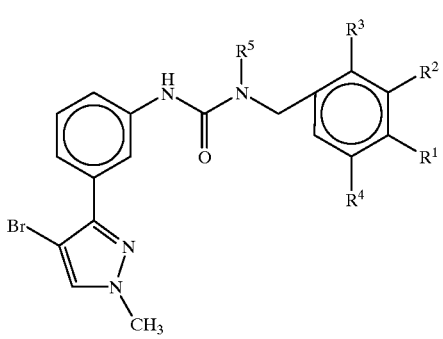

| Compound No. | R$^1$ | R$^2$ | R$^3$ | R$^4$ | R$^5$ | IP$_3$ AP-3 IC$_{50}$ nM | WT 5HT$_{2A}$ LSD IC$_{50}$ nM |
|---|---|---|---|---|---|---|---|
| N-[3-(4-bromo-1-methylpyrazol-3-yl)phenyl][phenylmethylamino]carboxamide | | | | | | | |
| 116143 | H | H | H | H | H | 120 | 47 |
| N-[3-(4-bromo-1-methylpyrazol-3-yl)phenyl][{(4-fluorophenyl)methyl}amino]carboxamide | | | | | | | |
| 116182 | F | H | H | H | H | 89 | 132 |
| N-[3-(4-bromo-1-methylpyrazol-3-yl)phenyl][{(3,4-dimethoxyphenyl)methyl}amino]carboxamide | | | | | | | |
| 116183 | OMe | OMe | H | H | H | — | 1010 |
| N-[3-(4-bromo-1-methylpyrazol-3-yl)phenyl][{(3,4,5-trimethoxyphenyl)methyl}amino]carboxamide | | | | | | | |
| 116184 | OMe | OMe | H | OMe | H | — | 2960 |
| N-[3-(4-bromo-1-methylpyrazol-3-yl)phenyl][{(2-methylphenyl)methyl}amino]carboxamide | | | | | | | |
| 116185 | H | H | Me | H | H | — | 769 |
| N-[3-(4-bromo-1-methylpyrazol-3-yl)phenyl][{(4-methoxyphenyl)methyl}amino]carboxamide | | | | | | | |
| 116189 | OMe | H | H | H | H | — | 102 |

-continued

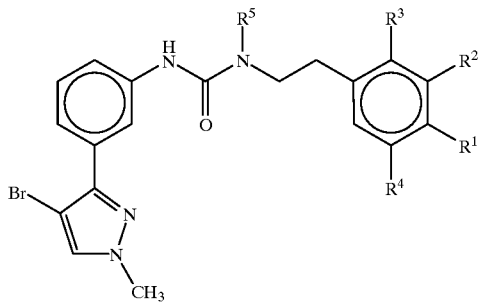

N-[3-(4-bromo-1-methylpyrazol-3-yl)phenyl][{2-(4-methoxyphenyl)ethyl}amino]carboxamide

| 116194 | OMe | H | H | H | H | 32 | 61 |

Example 11

In Vivo Analysis

A. 1-(2,5-dimethoxy-4-iodophenyl)-2-aminopropane ("DOI") Motor Dysfunction Analysis: 116081 and 116082

The profiles of 116082 and 116081 in in vitro functional assays suggested that this compound exhibit selective $5HT_{2A}$ inverse agonist properties. Assessment of 5-HT2 receptor antagonism in vivo was made by using the DOI locomotor activity test in rats as described by Krebs-Thomson (*Psychopharmacology*, 140:69–74, 1998).

The peripheral administration of the hallucinogen and 5HT2 agonist DOI [1-(2,5-dimethoxy-4-iodophenyl)-2-aminopropane] at a dose of 0.3 mg/kg typically produces motor dysfunction in rats as shown by a decrease in ambulation (i.e. walking and running), fine movement of the body at rest (i.e. grooming, licking) and rearing activity (i.e. standing on hindlimbs). Motor function was assessed by using automated locomotor activity cages. The rats were placed in a standard rodent cage surrounded by photocell beams, which allow for automated recording of motor activity. The animals were under no motivational constraints and were free to move around the cage. In this test, male Sprague-Dawley rats (n=6 per dose) were administered with 11081 or 11082 (intraperitoneal injection) followed by a subcutaneous administration of DOI 30 min later. A reversal of DOI-induced motor dysfunction in rats is considered to be predictive of the ability of the test compound to antagonize 5HT2 receptors in vivo.

Figure 3:
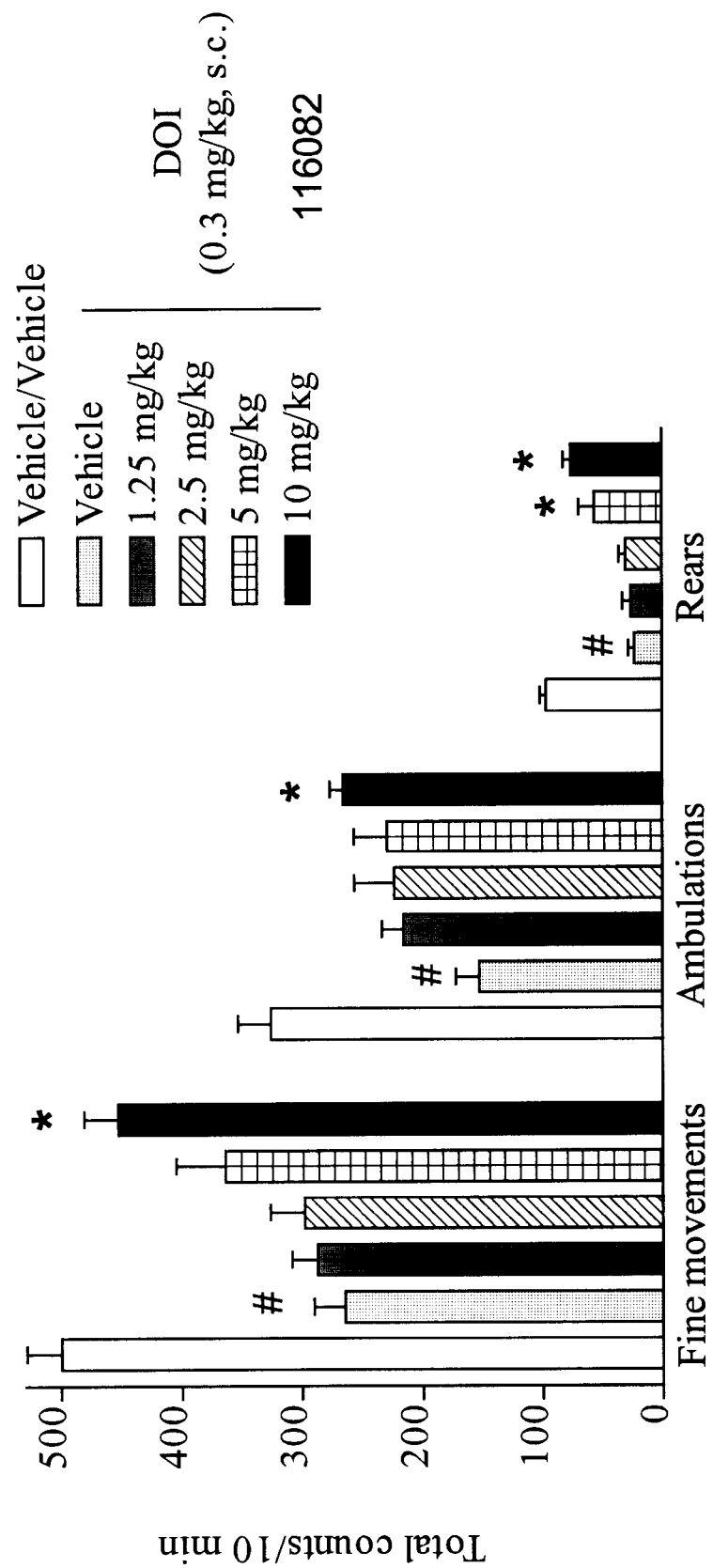
FIG. 3 provides a graphic summary of dose-response results from in vivo analysis of compound 116082 in a 1-(2,5-dimethoxy-4-iodophenyl)-2-aminopropane ("DOI") inhibition study (fine movement; ambulation; and animal rearing outcome measures). 116082 was administered 30 min prior to DOI. Animals were placed in locomotor activity cages 10 min after DOI administration and activity was measured for 10 min. Results are presented as total activity counts over the 10 min of exposure to the locomotor activity apparatus.
Figure 4:
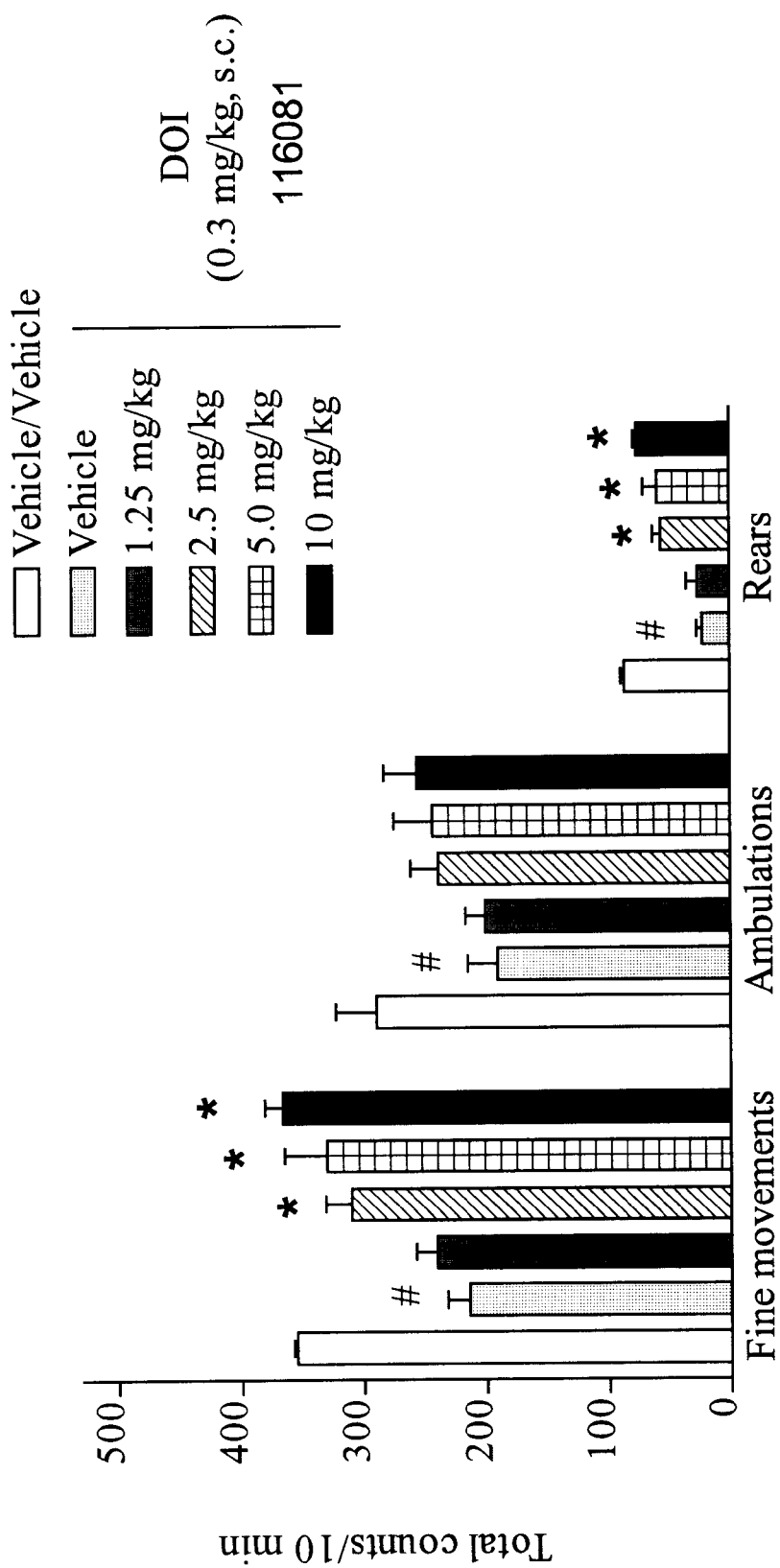
FIG. 4 provides a graphic summary of dose-response results from in vivo analysis of compound 116081 in a DOI inhibition study (fine movement; ambulation; and animal rearing outcome measures). 116081 was administered 30 min prior to DOI. Animals were placed in locomotor activity cages 10 min after DOI administration and activity was measured for 10 min. Results are presented as total activity counts over the 10 min of exposure to the locomotor activity apparatus.

Based upon the results presented in FIGS. 3 and 4, a conclusion that can be drawn from the data is that 116081 and 116082 beneficially reverses DOI-induced motor dysfunction. Based upon the data developed, another conclusion that can be drawn is that 116082 exhibits its serotonin 5HT2 antagonist properties at doses ranging from 5 to 10 mg/kg and that 116081 exhibits its serotonin 5HT2 antagonist properties at dose ranging from 2.5 to 10 mg/kg.

B. Extrapyramidal Side Effect Analysis: 116082

A significant problem of currently marketed typical antipsychotics such as haloperidol is the occurrence of extrapyramidal side effects. The extrapyramidal motor syndrome (EPS) is characterized by Parkinson-like symptoms resulting from the blockade of brain striatal dopamine D2 and D1 receptors (Snyder, S H. *Am. J. Psychiatry*, 138:461–468, 1981).

The propensity of a potential therapeutic to block striatal dopamine receptors can be evaluated by measurement of the induction of catalepsy in rodents (Hoffman and Donavan, *Psychopharmacology* 120:128–133, 1995). Catalepsy is characterized by body rigidity and is commonly measured using the bar test in rats (Prinssen et al., *Psychopharmacology*, 144:20–29,1999). Thus, this test was used to determine the potential EPS side effect liability of116082 in vivo.

In the bar test, the rat's forelimbs were placed on a horizontal, cylindrical metal bar (diameter 0.75 cm, height 10 cm) and the time during which both forelimbs remained on the bar was determined up to a maximum of 30 sec. This test was repeated 3 times consecutively and catalepsy was defined as the average of the three duration measurements. Male Sprague-Dawley (average body weight 300 g) rats were administered 116082 (intraperitoneal injection) 60 min prior to the test. The number of animals tested at each doses was 6 to 8.

Figure 5:
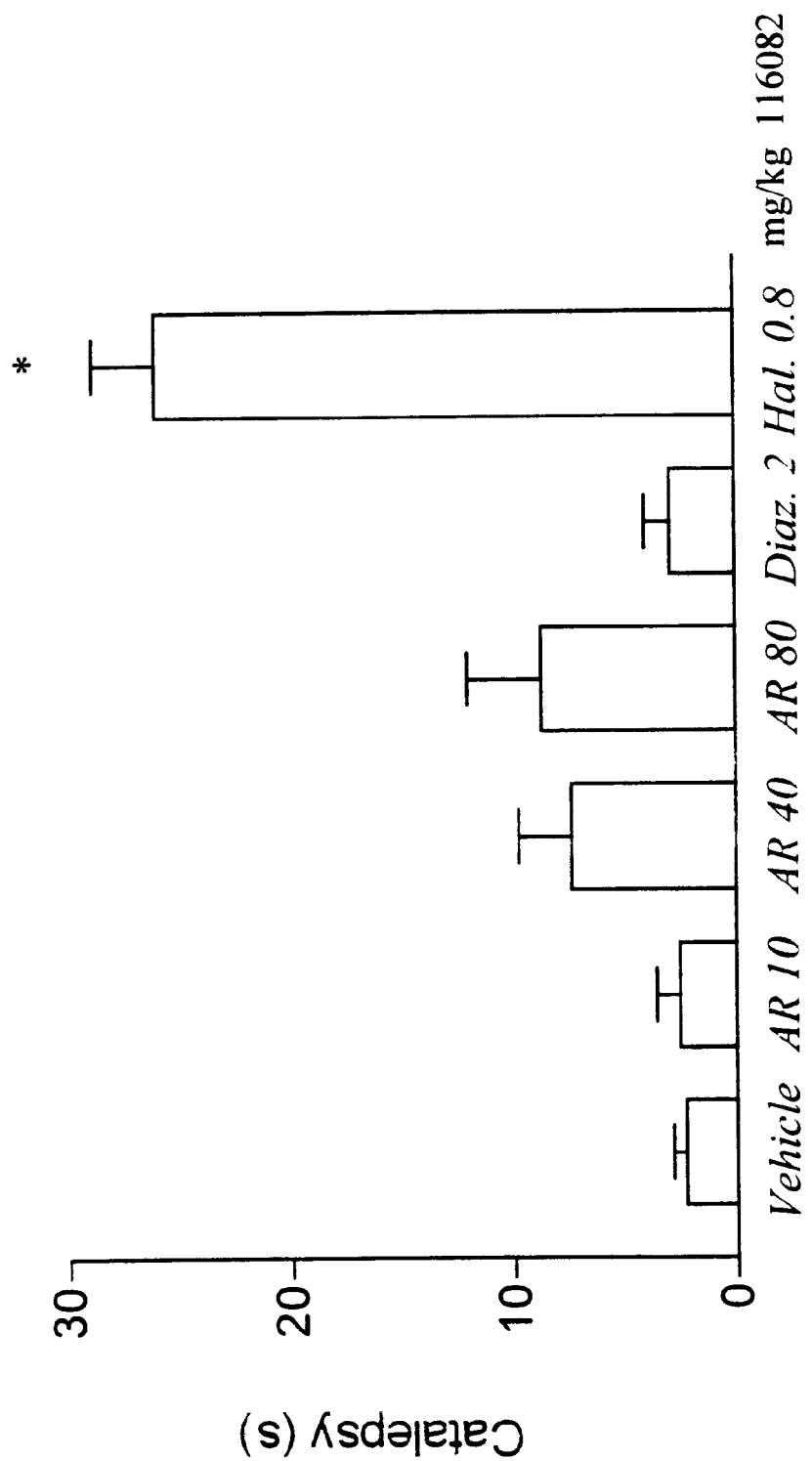
FIG. 5 provides a graphic summary of results from in vivo analysis of compound 116082 in a catalepsy-muscle rigidity study. 116082 (AR10, AR40, and AR80 mg/kg) and haloperidol (Hal.0.8 mg/kg) were compared in the bar catalepsy test in rats. The test compounds were administered intraperitoneally 60 min prior to the test. Time during which both forelimbs remained on the bar was recorded up to a maximum of 30 sec. Values represent the average of 3 consecutive measurements (means±SEMs, n=6–8/group). *P<0.05 vs. vehicle, Student t-test.

The data presented in FIG. 5 support the conclusion that 116082 did not induce a dose-dependent increase in time spent on the bar, thus suggesting that 116082 does not induce catalepsy in rats at doses ranging from 10 to 80 mg/kg. On the other hand, haloperidol induced a significant increase in time spent on the bar indicating that this compound induces catalepsy in rats at a dose of 0.8 mg/kg. The data thus support the conclusion that 116082 does not induce extrapyramidal side effects in rats at a dose 8 times greater than the dose required to block $5HT_{2A}$ receptors in vivo (i.e., see DOI example, supra).

Using the same dosing parameters and protocol, it was further determined that 116081 also did not produce a cataleptic response, under the criteria set forth above (n=10 per dose). Data not shown.

C. Oral Availability: 116081 and 116082

Based upon the in vivo data developed, oral bioavailability of compounds 110681 and 110682 was considered. The compounds were administered by oral gavage at a dose of 50 mg/kg, 30 min prior to DOI in rats (see Example 11A, supra). Animals were placed in the locomotor activity cages 10 min after DOI administration and activity was measured for 10 min. Results, presented in FIG. 6, provide total activity counts over the 10 min of exposure to the locomotor activity apparatus.

Figure 6:
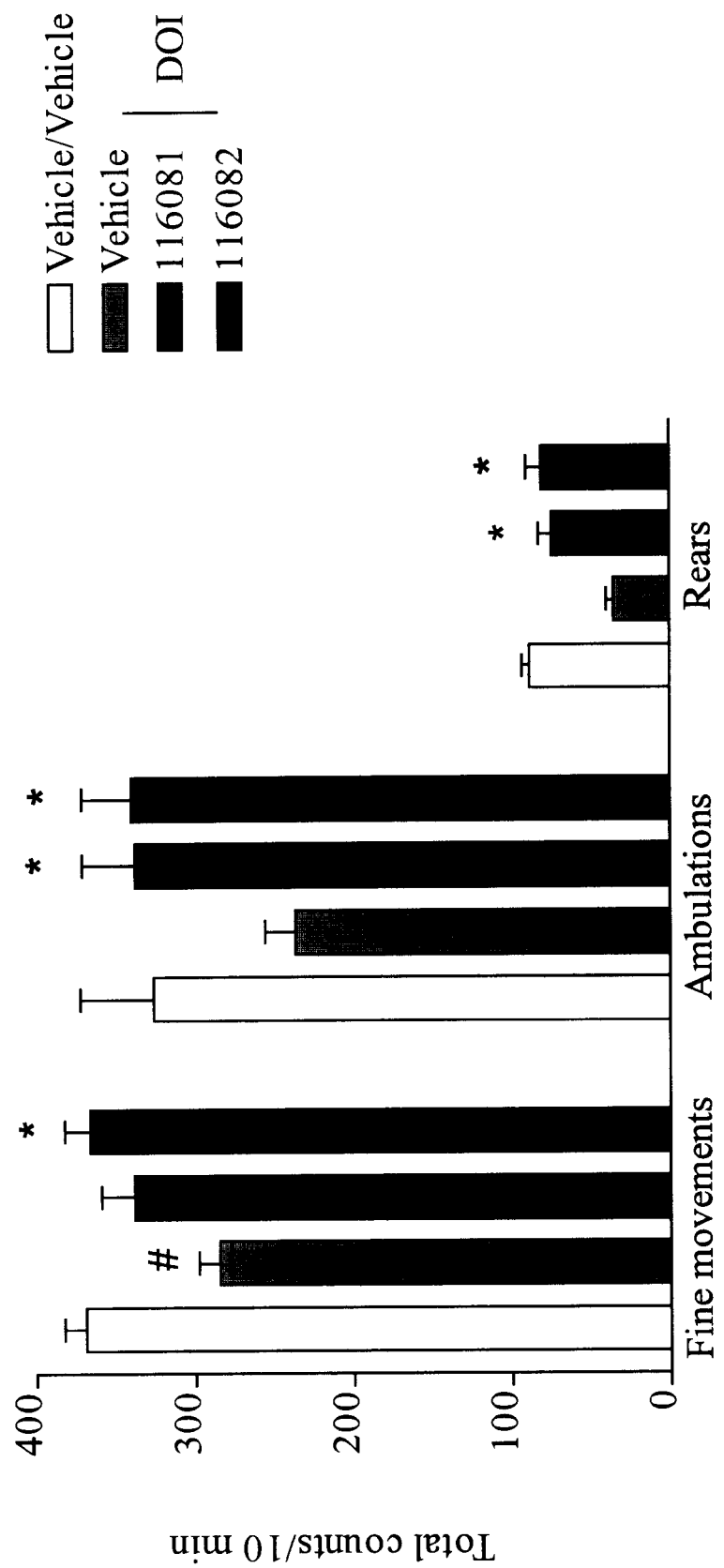
FIG. 6 provides a graphic summary of the effects of oral administration of 116082 and 116081 in a DOI inhibition study in rats. Values represent the mean±SEMs (n=6/group). #P<0.05 vs. vehicle/vehicle, *P<0.05 vs. vehicle/DOI, Student t-test.

The data presented in FIG. 6 support the conclusion that oral administration of 116082 and 116081 at a dose of 50 mg/kg reversed DOI-induced motor dysfunction in rats. The data further support the conclusion that a 50 mg/kg dose of 116082 and 116081 administered orally was as efficacious as a 10 mg/kg dose of the same compounds administered intraperitoneally (FIGS. 3 and 4).

These data support the conclusion that 116082 and 116081 are orally active, with oral bioavailability greater or equal to 20%.

D. Antagonism of MK801-induced hyperlocomotion: a model of potential antipsychotic ("antipositive") activity In rodents, the non-competitive NMDA receptor antagonist MK-801 induces significant increases in locomotor activity and stereotypy. Because part of the symptomatology of schizophrenia may be related to altered glutamate transmission at the NMDA receptor, the reversal of MK-801-induced hyperlocomotor activity in rodents has been used routinely as an animal model for detecting potential antipsychotic activity (O'Neill et al., Pharmacology Biochem. Behav., 63: 237–243, 1999). Thus, this test was used to determine potential antipsychotic properties of 116081 in vivo.

Figure 7:
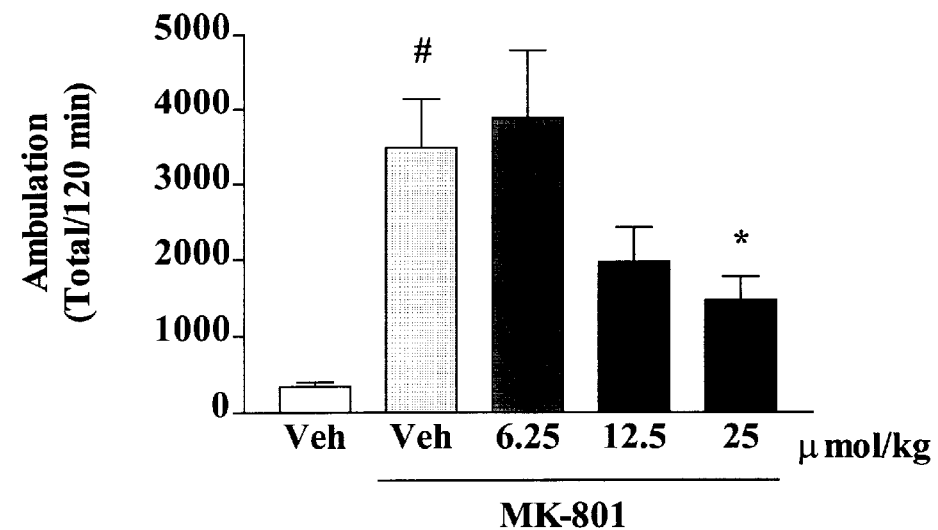
FIG. 7 provides a graphic summary of the reversal of MK-801-induced hyperactivity using 116081 (7A) and clozapine (7B). 116081 and clozapine dose-dependently attenuated MK801-induced hyperactivity as measured by a decrease in ambulations in MK-801-treated animals. 116081 produced a significant reversal of the effect of MK-801 at a dose of 25 µmol/kg (10 mg/kg). Results are presented as total activity counts over the 120 min of exposure to the locomotor activity apparatus after administration of MK-801. Data (mean±SEM) were analyzed by ANOVA followed by Dunnett's test (n=6–8/group).
Figure 7:
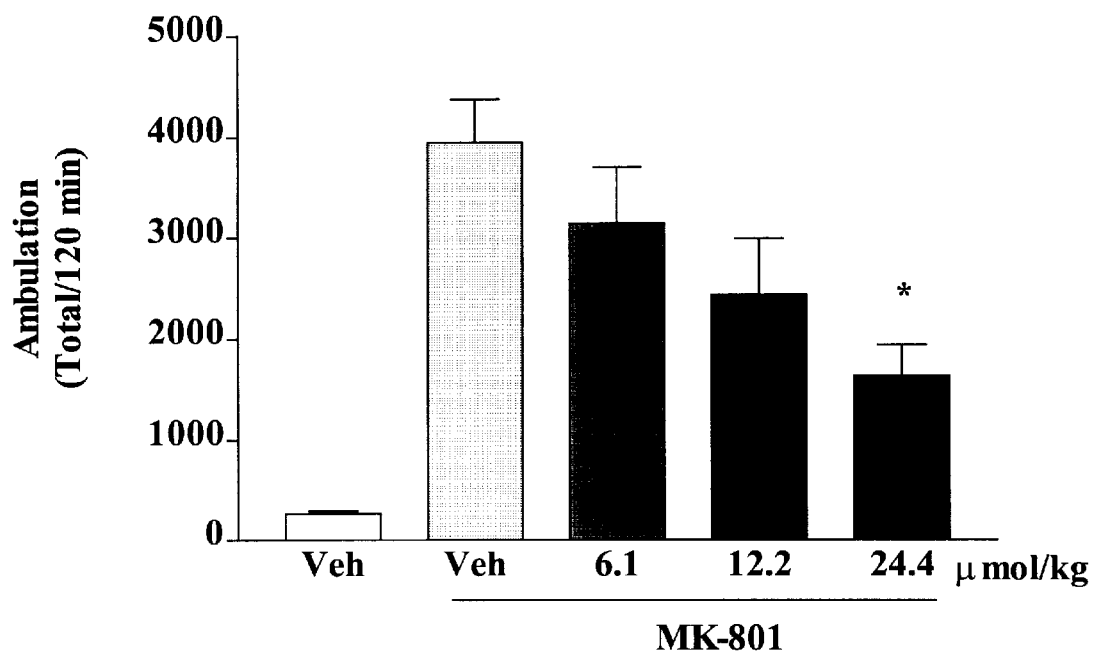

Motor activity was assessed using automated locomotor activity cages as described above (Example 11(A), supra.). Male Sprague-Dawley rats (250–350 g body weight) were administered test compounds (i.p.) and placed in the locomotor activity cages for 30 min of habituation. Following habituation, animals were administered MK-801 (0.5 μmol/kg=0.17 mg/kg, s.c.) and then immediately placed back into the locomotor activity cages, and activity was measured for 120 min. A reversal of MK-801-induced motor activity (as shown by a significant increase of ambulation) in rats is considered to be predictive of the ability of the test compound to reverse psychotic symptoms. Results are presented in FIG. 7.

Based upon the results presented in FIGS. 7A and 7B, 116081 appears to be equiefficacious to the atypical antipsychotic clozapine in reversing the motor activity induced by MK-801. The data, therefore, thus support the conclusion that AR116081 may have antipsychotic properties.

Example 12

Synthetic Approaches

The compounds disclosed in this invention may be readily prepared according to a variety of synthetic manipulations, all of which would be familiar to one skilled in the art. In the general syntheses set forth below, the labeled substituents have the same identifications as set out in the definitions of the compounds above.

Compounds of general formula (I) can be obtained via a variety of synthetic routes all of which would be familiar to one skilled in the art. The reaction of isocyanates with amines is a commonly practiced method for the formation of ureas (see Org. Syn. Coll. Vol. V, (1973), 555). Amine (IV), 3-(4-bromo-1-methylpyrazole-3-yl)phenylamine, commercially available from Maybridge Chemical Company, Catalog No. KM01978, CAS No. 175201-77-1] reacts readily with isocyanates (V) in inert solvents such as halocarbons to yield the desired ureas of general formula (I) wherein $R^1=R^2=H$:

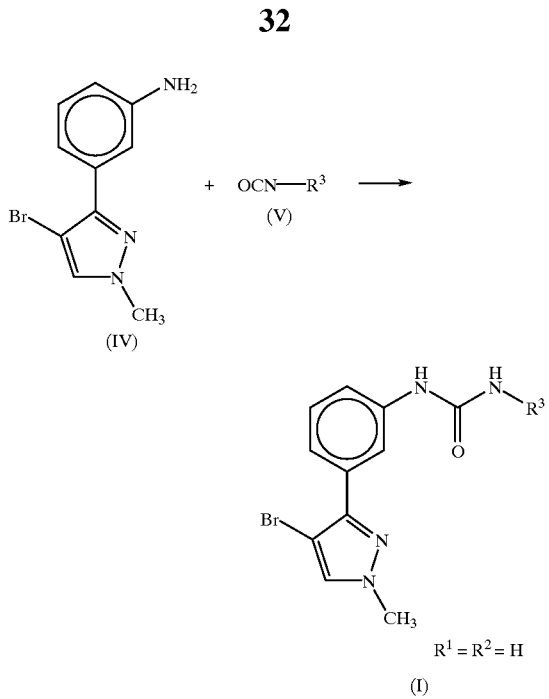

Alternatively the amine (IV) can be converted to the corresponding isocyanate (VI) by the action of phosgene or a suitable phosgene equivalent, e.g. triphosgene, in an inert solvent such as a halocarbon in the presence of an organic base such as triethylamine or ethyldiisopropylamine. Isocyanate (VI) reacts with amines of general formula (VII), in an analogous fashion to that described above for the reaction of (IV) with (V), yielding the desired ureas of general formula (I) wherein $R^1=H$:

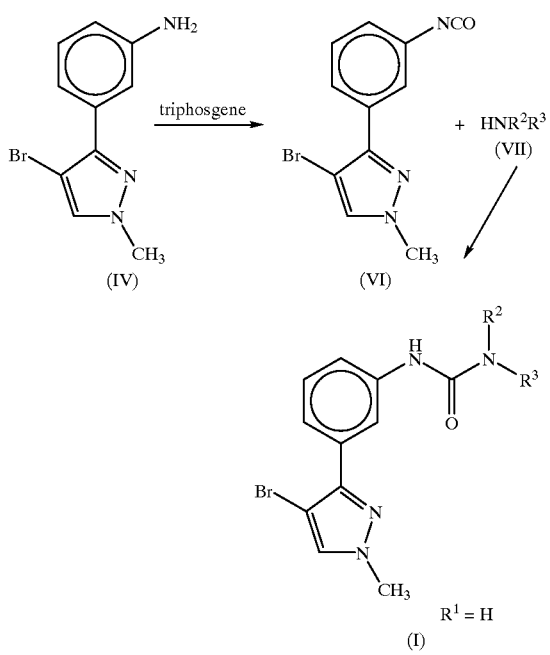

Alternatively wherein the isocyanate of general formula (V) is not commercially available it can be prepared from the corresponding amine of general formula (VIII) in an analogous procedure to that described above for the preparation of (VI). Reaction of these isocyanates with (IV) would again yield the requisite ureas of general formula (I) wherein $R^1=R^2=H$:

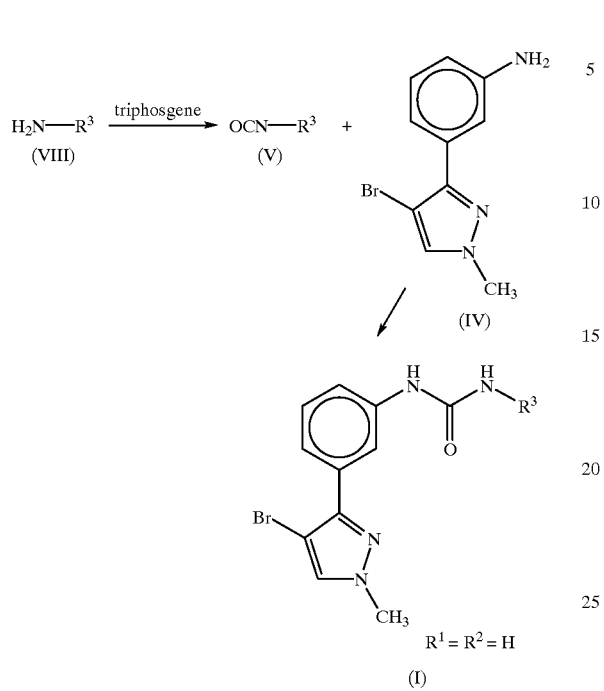

Amines of general formula (VII) are also readily converted to activated isocyanate equivalents of general formula (IX) by the sequential action of carbonyldiimidazole and methyl iodide in tetrahydrofuran and acetonitrile respectively (R. A. Batey et al, *Tetrahedron Lett.*, (1998), 39, 6267–6270.) Reaction of (IX) with (IV) in an inert solvent such as a halocarbon would yield the requisite ureas of general formula (I) wherein $R^1=H$:

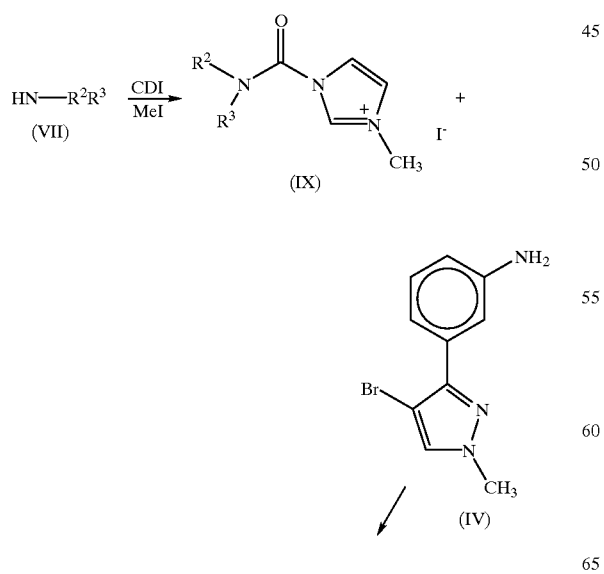

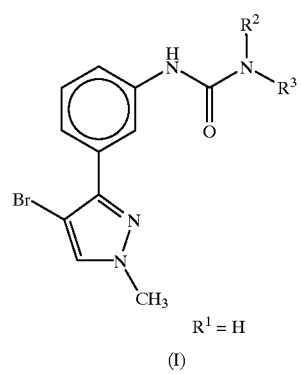

Amine (IV) may be monomethylated according to the procedure of J. Barluenga et al, *J. Chem. Soc., Chem. Commun.*, (1984), 20, 1334–1335, or alkylated according to the procedure of P. Marchini et al, *J. Org. Chem.*, (1975), 40(23), 3453–3456, to yield compounds of general formula (X) wherein $R^1$=lower alkyl. These materials may be reacted as above with reagents of general formula (V) and (IX) as depicted below:

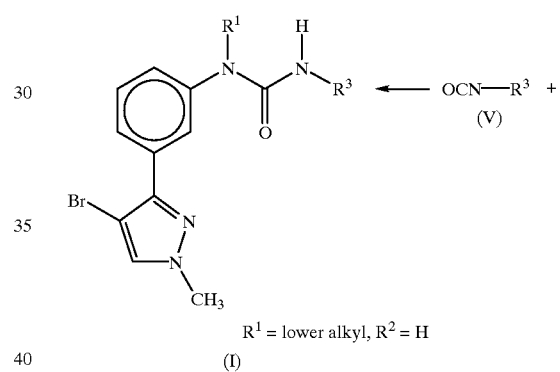

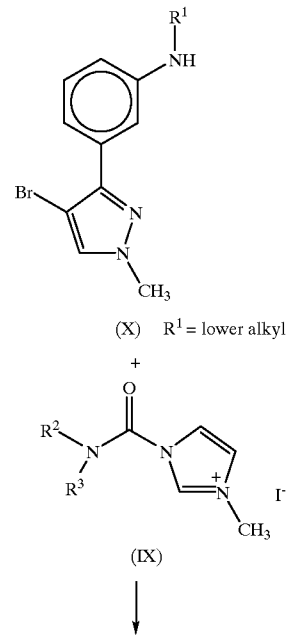

-continued

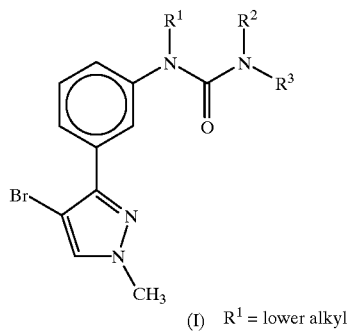

(I)  R¹ = lower alkyl

Compounds of formula (A) or a solvate or physiologically functional derivative thereof for use as a therapeutic agent, specifically as a modifier of the activity of the serotonin 5-HT$_{2A}$ receptor. Modifiers of the activity of the serotonin 5-HT$_{2A}$ receptor are believed to be of potential use for the treatment or prophylaxis of CNS, gastrointestinal, cardiovascular, and inflammatory disorders. Compounds of the formula (A) may be administered by oral, sublingual, parenteral, rectal, or topical administration. In addition to the neutral forms of compounds of formula (A) by appropriate addition of an ionizable substituent, which does not alter the receptor specificity of the compound, physiologically acceptable salts of the compounds may also be formed and used as therapeutic agents. Different amounts of the compounds of formula (A) will be required to achieve the desired biological effect. The amount will depend on factors such as the specific compound, the use for which it is intended, the means of administration, and the condition of the treated individual. A typical dose may be expected to fall in the range of 0.001 to 200 mg per kilogram of body weight of the treated individual. Unit does may contain from 1 to 200 mg of the compounds of formula (A) and may be administered one or more times a day, individually or in multiples. In the case of the salt or solvate of a compound of formulas (A), the dose is based on the cation (for salts) or the unsolvated compound.

Compositions, including, but not limited to, pharmaceutical compositions, comprising at least one compound of formula (A) and/or an acceptable salt or solvate thereof (e.g., a pharmaceutically acceptable salt or solvate) as an active ingredient combined with at least one carrier or excipient (e.g., pharmaceutical carrier or excipient). Pharmaceutical compositions may be used in the treatment of clinical conditions for which a modifier of the activity of the serotonin 5-HT$_{2A}$ receptor is indicated, particularly where the active ingredient is preferentially selective for the 5HT$_{2A}$ receptor over the 5HT$_{2A}$ receptor, and most particularly where the active ingredient is also an inverse agonist at the 5HT$_{2A}$ receptor. At least one compound of formula (A) may be combined with the carrier in either solid or liquid form in a unit dose formulation. The pharmaceutical carrier must be compatible with the other ingredients in the composition and must be tolerated by the individual recipient. Other physiologically active ingredients may be incorporated into the pharmaceutical composition of the invention if desired, and if such ingredients are compatible with the other ingredients in the composition. Formulations may be prepared by any suitable method, typically by uniformly mixing the active compound(s) with liquids or finely divided solid carriers, or both, in the required proportions, and then, if necessary, forming the resulting mixture into a desired shape.

Conventional excipients, such as binding agents, fillers, acceptable wetting agents, tabletting lubricants, and disintegrants may be used in tablets and capsules for oral administration. Liquid preparations for oral administration may be in the form of solutions, emulsions, aqueous or oily suspensions, and syrups. Alternatively, the oral preparations may be in the form of dry powder that can be reconstituted with water or another suitable liquid vehicle before use. Additional additives such as suspending or emulsifying agents, non-aqueous vehicles (including edible oils), preservatives, and flavorings and colorants may be added to the liquid preparations. Parenteral dosage forms may be prepared by dissolving the compound of the invention in a suitable liquid vehicle and filter sterilizing the solution before filling and sealing an appropriate vial or ampoule. These are just a few examples of the many appropriate methods well known in the art for preparing dosage forms.

The fifth aspect of the present invention provides for the use of a compound of formula (A) in the preparation of a medicament for the treatment of a medical condition for which a modifier of the activity of the serotonin 5-HT$_{2A}$ receptor is indicated.

Another aspect of the present invention provides for a method of treatment of a clinical condition of a mammal, such as a human, for which a modifier of the activity of the serotonin 5-HT$_{2A}$ receptor is indicated, which comprises the administration to the mammal of a therapeutically effective amount of a compound of formula (A) or a physiologically acceptable salt, solvate, or physiologically functional derivative thereof.

Example 13

Experimental Data

Mass spectra were recorded on a Micromass Platform™ LC with Gilson HPLC. Infra-red spectra were recorded on a Nicolet Avatar™ 360 FT-IR. Melting points were recorded on a Electrothermal IA9200™ apparatus and are uncorrected. Proton nuclear magnetic resonance spectra were recorded on a Bruker™ 300 MHz machine. Chemical shifts are given with respect to tetramethylsilane. In the text the following abbreviations are used; s (singlet), d (doublet), t (triplet), m (multiplet) or combinations thereof. Chemical shifts are quoted in parts per million (ppm) and with coupling constants in Hertz.

Thin layer chromatography was carried out using aluminium backed silica plates (250 μL; GF$_{254}$). HPLC was recorded either on a HP Chemstation™ 1100 HPLC using a Hichrom 3.5 C18 reverse phase column (50 mm×2.1 mm i.d.). Linear gradient elution over 5 minutes—95% water (+0.1% TFA)/5% acetonitrile (+0.05% TFA) down to 5% water/95% acetonitrile. Flow rate 0.8 mL/min [Method A]; or on a Hichrom 3.5 C18 reverse phase column (100 mm×3.2 mm i.d.). Linear gradient elution over 11 minutes—95% water (+0.1% TFA)/5% acetonitrile (+0.05% TFA) down to 5% water/95% acetonitrile. Flow rate 1 mL/min [Method B]. Samples were routinely monitored at 254 nM unless otherwise stated.

All reagents were purchased from commercial sources.

Experiment 1

Preparation and Analysis of 103487

N-[3-(4-bromo-1-methylpyrazol-3-yl)phenyl][{(4-trifluoromethoxy)phenyl}amino]carboxamide This compound is commercially available from Maybridge Chemical Company, Catalog No. KM04515.

One or the other (as indicated) of the two following synthetic protocols was used to generate each of the compounds below:
Protocol A:

To an isocyanate (1 mmol) in CH$_2$Cl$_2$ (4 mL) was added dropwise a solution of 3-(3-aminophenyl)-4-bromo-1-methylpyrazole (1 mmol) in CH$_2$Cl$_2$ (4 mL). The mixture was stirred for 16 hours and concentrated. Chromatography on flash silica (20%–80% EtOAc/hexane) followed by recrystallisation gave the pure urea.
Protocol B:
To a stirred solution of triphosgene (0.33 mmol) in CH$_2$Cl$_2$ (4 mL) was added dropwise a solution of 3-(3-aminophenyl)-4-bromo-1-methylpyrazole (1 mmol) and triethylamine (2 mmol) in CH$_2$Cl$_2$ (4 mL). After 1 hour, an aniline was added (1 mmol). The reaction mixture was stirred for 16 hours and concentrated. Chromatography on flash silica (20%–80%EtOAc/hexane) followed by recrystallisation gave the pure urea.

Experiment 2

Preparation and Analysis of 116079

N-[3-(4-bromo-1-methylpyrazol-3-yl)phenyl][(4-methylthiophenyl)amino]carboxamide
[Protocol A]—4-(methylthio)phenyl isocyanate
colourless solid (EtOAc/hexane)
MS (ES+): m/z (%)=419 (M+H $^{81}$Br, 100), 417 (M+H $^{79}$Br, 94).
$^1$H-NMR (MeOH d$_4$): δ=2.42 (3H, s, SCH$_3$), 3.81 (3H, s, NCH$_3$), 7.06 (1H, m, ArH), 7.22 (2H, m, ArH), 7.37 (2H, m, ArH), 7.42–7.61 (4H, m, ArH).
HPLC: retention time 3.35 min [Method A].

Experiment 3

Preparation and Analysis of 116081

N-[3-(4-bromo-1-methylpyrazol-3-yl)phenyl][(4-chlorophenyl)amino]carboxamide
[Protocol A]—4-chlorophenyl isocyanate
colourless solid (EtOAc/hexane)
MS (ES+): m/z (%)=409 (M+H $^{81}$Br $^{37}$Cl, 19), 407 (M+H $^{79}$Br $^{37}$Cl ($^{81}$Br $^{35}$Cl), 100), 405 (M+H $^{79}$Br $^{35}$Cl, 81).
$^1$H-NMR (MeOH d$_4$): δ=3.81 (3H, s, CH$_3$), 7.07 (1H, m, ArH), 7.23 (2H, m, ArH), 7.36–7.60 (6H, m, ArH).
HPLC: retention time 3.42 min [Method A].

Experiment 4

Preparation and Analysis of 116082

{[3-(4-bromo-1-methylpyrazol-3-yl)phenyl]amino}-N-(4-fluorophenyl)carboxamide
[Protocol A]—4-fluorophenyl isocyanate
colourless solid (EtOAc/hexane)
MS (ES+): m/z (%)=391 (M+H $^{81}$Br, 96), 389 (M+H $^{79}$Br, 100).
$^1$H-NMR (MeOH d$_4$): δ=3.81 (3H, s, CH$_3$), 6.93–7.11 (3H, m, ArH), 7.37–7.61 (6H, m, ArH).
HPLC: retention time 3.11 min.

Experiment 5

Preparation and Analysis of 116087

{[3-(4-bromo-1-methylpyrazol-3-yl)phenyl]amino}-N-[2-(trifluoromethoxy)phenyl]carboxamide
[Protocol A]—2-(trifluoromethoxy)phenyl isocyanate
colourless solid (EtOAc/hexane)
MS (ES+): m/z (%)=457 (M+H $^{81}$Br, 100), 455 (M+H $^{79}$Br, 95).
$^1$H-NMR (DMSO d$_6$): δ=3.79 (3H, s, CH$_3$), 7.06–7.18 (2H, m, ArH), 7.38–7.49 (2H, m, ArH), 7.51–7.62 (2H, m, ArH), 7.65 (1H, m, ArH), 7.71 (1H, s, ArH), 8.24 (1H, dd, J=1.1, 8.2, ArH), 8.56 (1H, s, NH), 9.49 (1H, s, NH).
HPLC: retention time 3.40 min.

Experiment 6

Preparation and Analysis of 116089

{[3-(4-bromo-1-methylpyrazol-3-yl)phenyl]amino}-N-(2-nitrophenyl)carboxamide
[Protocol A]—2-nitrophenyl isocyanate
yellow solid (EtOAc/hexane)
MS (ES+): m/z (%)=418 (M+H $^{81}$Br, 98), 416 (M+H $^{79}$Br, 100).
$^1$H-NMR (DMSO d$_6$): δ=$^1$H-NMR (DMSO d$_6$): =3.79 (3H, s, NCH$_3$), 7.14 (1H, m, ArH), 7.24 (1H, m, ArH), 7.50 (1H, t, J=7.7, ArH), 7.60 (2H, m, ArH), 7.67 (1H, s, ArH), 7.71 (1H, s, ArH), 8.10 (1H, m, ArH), 8.29 (1H, m, ArH), 9.65 (1H, s, NH), 10.09 (1H, s, NH).
HPLC: retention time 3.10 min [Method A].

Experiment 7

Preparation and Analysis of 116091

{[3-(4-bromo-1-methylpyrazol-3-yl)phenyl]amino}-N-(4-methoxyphenyl)carboxamide
[Protocol A]—4-methoxyphenyl isocyanate
colourless solid (EtOAc/hexane)
MS (ES+): m/z (%)=403 (M+H $^{81}$Br, 100), 401 M+H $^{79}$Br, 96).
$^1$H-NMR (DMSO d$_6$): δ=3.71 (3H, s, OCH$_3$), 3.79 (3H, s, NCH$_3$), 6.87 (2H, d, J=8.9, ArH), 7.06 (1H, d, J=7.5, ArH), 7.39 (2H, d, J=8.9, ArH), 7.45–7.61 (3H, m, ArH), 7.65 (1H, s, ArH), 8.52 (1H, S, NH), 8.84 (1H, s, NH).
HPLC: retention time 3.08 min.

Experiment 8

Preparation and Analysis of 116092

{[3-(4-bromo-1-methylpyrazol-3-yl)phenyl]amino}-N-(2-methylphenyl)carboxamide
[Protocol A]—o-tolyl isocyanate
colourless solid (EtOAc/hexane)
MS (ES+): m/z (%)=387 (M+H $^{81}$Br, 94), 385 (M+H $^{79}$Br, 100).
$^1$H-NMR (MeOH d$_4$): δ=2.29 (3H, s, CH$_3$), 3.81 (3H, s, NCH$_3$), 7.03 (1H, dt, J=1.1, 7.5, ArH), 7.09 (1H, dt, J=1.1, 7.5, ArH), 7.13–7.22 (2H, m, ArH), 7.45 (1H, t, J=7.9, ArH), 7.49–7.57 (2H, m, ArH), 7.60–7.68 (2H, m, ArH).
HPLC: retention time 2.96 min.

Experiment 9

Preparation and Analysis of 116097

{[3-(4-bromo-1-methylpyrazol-3-yl)phenyl]amino}-N-[4-(trifluoromethyl)phenyl]carboxamide
[Protocol A]—4-(trifluoromethyl)phenyl isocyanate
colourless solid (EtOAc/hexane)
MS (ES+): m/z (%)=441 (M+H $^{81}$Br, 94), 439 (M+H $^{79}$Br, 100).
$^1$H-NMR (MeOH d$_4$): δ=3.82 (3H, s, CH$_3$), 7.04–7.16 (3H, m, ArH), 7.20–7.47 (6H, m, ArH).
HPLC: retention time 3.56 min.

Experiment 10

Preparation and Analysis of 116105

{[3-(4-bromo-1-methylpyrazol-3-yl)phenyl]amino}-
  N-(3-chlorophenyl)carboxamide
[Protocol A]—3-chlorophenyl isocyanate
colourless solid (EtOAc/hexane)
MS (ES+): m/z (%)=409 (M+H $^{81}$Br $^{37}$Cl, 26), 407 (M+H $^{79}$Br $^{37}$Cl ($^{81}$Br $^{35}$Cl), 100), 405 (M+H $^{79}$Br $^{35}$Cl, 70).
$^1$H-NMR (MeOH d$_4$): δ=3.81 (3H, s, NCH$_3$), 7.04 (1H, m, ArH), 7.10 (1H, m, ArH), 7.28 (2H, m, ArH), 7.47 (1H, t, J=7.8, ArH), 7.55 (1H, m, ArH), 7.63 (1H, m, ArH), 7.68 (1H, s, ArH), 7.73 (1H, m, ArH), 9.04 (2H, s, NH).
HPLC: retention time 3.20 min [Method A].

Experiment 11

Preparation and Analysis of 116108

{[3-(4-bromo-1-methylpyrazol-3-yl)phenyl]amino}-
  N-(2-chlorophenyl)carboxamide
[Protocol A]—2-chlorophenyl isocyanate
colourless solid (EtOAc/hexane)
MS (ES+): m/z (%)=409 (M+H $^{81}$Br $^{37}$Cl, 24), 407 (M+H $^{79}$Br $^{37}$Cl ($^{81}$Br $^{35}$Cl), 100), 405 (M+H $^{79}$Br $^{35}$Cl, 72).
$^1$H-NMR (MeOH d$_4$): δ=3.81 (3H, s, NCH$_3$), 7.03 (1H, m, ArH), 7.11 (1H, m, ArH), 7.28 (1H, m, ArH), 7.35–7.53 (3H, m, ArH), 7.55 (1H, s, ArH), 7.62 (1H, m, ArH), 8.11 (1H, m, ArH).
HPLC: retention time 3.13 min.

Experiment 12

Preparation and Analysis of 116110

{[3-(4-bromo-1-methylpyrazol-3-yl)phenyl]amino}-
  N-[4-(methylethyl)phenyl]carboxamide
[Protocol A]—4-isopropylphenyl isocyanate
colourless solid (THF/hexane)
MS (ES+): m/z (%)=415 (M+H $^{81}$Br, 100), 413 (M+H $^{79}$Br, 92).
$^1$H-NMR (MeOH d$_4$): δ=1.23 (6H, d, J=6.8, 2×CH$_3$), 2.86 (1H, septet, J=6.8, CH), 3.82 (3H, s, NCH$_3$), 7.09 (1H, m, ArH), 7.16 (2H, d, J=7.6, ArH), 7.31 (2H, d, J=7.6, ArH), 7.42–7.51 (2H, m, ArH), 7.54 (1H, s, ArH), 7.59 (1H, m, ArH).
HPLC: retention time 3.66 min.

Experiment 13

Preparation and Analysis of 116111

{[3-(4-bromo-1-methylpyrazol-3-yl)phenyl]amino}-
  N-(3-methoxyphenyl)carboxamide
[Protocol A]—3-methoxyphenyl isocyanate
colourless solid (EtOAc/hexane)
MS (ES+): m/z (%)=403 (M+H $^{81}$Br, 100), 401 (M+H $^{79}$Br, 96).
$^1$H-NMR (MeOH d$_4$): δ=3.73 (3H, s, OCH$_3$), 3.81 (3H, s, NCH$_3$), 6.59 (1H, m, ArH), 6.91 (1H, m, ArH), 7.08 (1H, m, ArH), 7.14 (2H, m, ArH), 7.39–7.61 (4H, m, ArH).
HPLC: retention time 2.90 min.

Experiment 14

Preparation and Analysis of 116112

{[3-(4-bromo-1-methylpyrazol-3-yl)phenyl]amino}-
  N-(3-methylphenyl)carboxamide
[Protocol A]—m-tolyl isocyanate
colourless solid (EtOAc/hexane)
MS (ES+): m/z (%)=387 (M+H $^{81}$Br, 100), 385 (M+H $^{79}$Br, 96).
$^1$H-NMR (DMSO d$_6$): δ=2.26 (3H, s, CH$_3$), 3.76 (3H, s, NCH$_3$), 6.79 (1H, m, ArH), 7.06–7.22 (3H, m, ArH), 7.29 (1H, m, ArH), 7.43–7.62 (3H, m, ArH), 7.68 (1H, s, ArH), 8.65 (1H, s, NH), 8.89 (1H, s, NH).
HPLC: retention time 3.05 min [Method A].

Experiment 15

Preparation and Analysis of 116113

{[3-(4-bromo-1-methylpyrazol-3-yl)phenyl]amino}-
  N-methyl-N-[4-(trifluoromethoxy)phenyl]
  carboxamide
[Protocol B]—N-methyl-4-(trifluoromethoxy)aniline
pale yellow solid (EtOAc/hexane)
MS (ES+): m/z (%)=471 (M+H $^{81}$Br, 88), 469 (M+H $^{79}$Br, 100).
$^1$H-NMR (MeOH d$_4$): δ=3.35 (3H, s, NCH$_3$), 3.81 (3H, s, NCH$_3$), 7.09 (1H, m, ArH), 7.25–7.51 (8H, m, ArH).
HPLC: retention time 3.56 min [Method A].

Experiment 16

Preparation and Analysis of 116119

N-[4-(tert-butyl)phenyl]{[3-(4-bromo-1-
  methylpyrazol-3-yl)phenyl]amino}carboxamide
[Protocol B]—4-tert-butylaniline
colourless solid (EtOAc/hexane)
MS (ES+): m/z (%)=429 (M+H $^{81}$Br, 98), 427 (M+H $^{79}$Br, 100).
$^1$H-NMR (DMSO d$_6$): δ=1.27 (9H, s, 3×CH$_3$), 3.79 (3H, s, NCH$_3$), 7.07 (1H, d, J=7.5, ArH), 7.29 (2H, d, J=8.7, ArH), 7.37 (2H, d, J=8.7, ArH), 7.45 (1H, t, J=7.5, ArH), 7.51–7.60 (2H, m, ArH), 7.66 (1H, s, ArH), 8.65 (1H, s, NH), 8.83 (1H, s, NH).
HPLC: retention time 3.77 min.

Experiment 17

Preparation and Analysis of 116122

N-[4-(dimethylamino)phenyl]{[3-(4-bromo-1-
  methylpyrazol-3-yl)phenyl]amino}carboxamide
[Protocol B]—N,N-dimethyl-p-phenylenediamine
colourless solid (EtOAc/hexane)
MS (ES+): m/z (%)=416 (M+H $^{81}$Br, 96), 414 (M+H $^{79}$Br, 100).
$^1$H-NMR (DMSO d$_6$): δ=2.86 (6H, s, NCH$_3$), 3.80 (3H, s, NCH$_3$), 6.80 (2H, m, ArH), 7.09 (1H, d, J=7.7, ArH), 7.28 (2H, m, ArH), 7.42 (1H, t, J=7.8, ArH), 7.52 (1H, m, ArH), 7.59 (1H, s, ArH), 7.67 (1H, s, ArH), 8.45 (1H, s, NH), 8.75 (1H, s, NH).
HPLC: retention time 2.07 min [Method A].

Experiment 18

Preparation and Analysis of 116138

N-(3,5-dichloro-4-methylphenyl){[3-(4-bromo-1-methylpyrazol-3-yl)phenyl]amino}carboxamide

[Protocol B]—3,5-dichloro-4-methylphenylamine
colourless solid (EtOAc/hexane)
MS (ES+): m/z (%)=457 (M+H, 35), 455 (M+H, 100), 453 (M+H, 65).
$^1$H-NMR (DMSO d$_6$): δ=2.32 (3H, s, CH$_3$), 3.79 (3H, s, NCH$_3$), 7.11 (1H, d, J=7.4, ArH), 7.46 (1H, t, J=7.8, ArH), 7.50–7.64 (4H, m, ArH), 7.68 (1H, s, ArH), 9.02 (1H, s, NH), 9.09 (1H, s, NH).
HPLC: retention time 3.66 min.

Experiment 19

Preparation and Analysis of 116139

{[3-(4-bromo-1-methylpyrazol-3-yl)phenyl]amino}-N-[4-(trifluoromethylthio)phenyl]carboxamide

[Protocol B]—4-(trifluoromethylthio)aniline
colourless solid (EtOAc/hexane)
MS (ES+): m/z (%)=473 (M+H $^{81}$Br, 100), 471 (M+H $^{79}$Br, 94).
$^1$H-NMR (DMSO d$_6$): δ=3.81 (3H, s, NCH$_3$), 7.11 (1H, d, J=7.5, ArH), 7.47 (1H, t, J=7.9, ArH), 7.51–7.63 (6H, m, ArH), 7.66 (1H, s, ArH), 9.03 (1H, s, NH), 9.16 (1H, s, NH).
HPLC: retention time 3.76 min.

Experiment 20

Preparation and Analysis of 116141

{[3-(4-bromo-1-methylpyrazol-3-yl)phenyl]amino}-N-(cyclohexyl)carboxamide

[Protocol B]—cyclohexylamine
colourless solid, m.p. 155.5–156.3° C. (EtOAc/hexane).
MS (ES+): m/z (%)=379 (M+H $^{81}$Br, 93), 377 (M+H $^{79}$Br, 100).
$^1$H-NMR (DMSO d$_6$): δ=1.07–1.34 (5H, m, 5×CH), 1.52 (1H, m, CH), 1.63 (2H, m, 2×CH), 1.76 (2H, m, 2×CH), 3.48 (1H, m, NCH), 3.74 (3H, s, CH$_3$), 6.15 (1H, d, J=7.8, ArH), 6.98 (1H, d, J=7.5, ArH), 7.32–7.43 (2H, m, ArH), 7.51 (1H, m, NH), 7.62 (1H, s, ArH), 8.50 (1H, s, NH).
HPLC: retention time 3.16 min [Method A].
TLC: retention factor 0.35 (50% EtOAc/hexane).

Experiment 21

Preparation and Analysis of 116143

{[3-(4-bromo-1-methylpyrazol-3-yl)phenyl]amino}-N-(phenylmethyl)carboxamide

[Protocol B]—benzylamine
colourless solid, m.p. 144.5–146.2° C. (EtOAc/hexane).
IR: $_{max}$=1622, 1565, 1467, 1374, 1239, 973, 802, 752, 695 cm$^{-1}$.
MS (ES+): m/z (%)=387 (M+H $^{81}$Br, 89), 385 (M+H $^{79}$Br, 100).
$^1$H-NMR (CD$_3$OD): δ=3.81 (3H, s, CH$_3$), 4.40 (2H, s, CH$_2$), 7.05 (1H, m, ArH), 7.19–7.51 (9H, m, ArH).
HPLC: retention time 3.06 min [Method A].a

Experiment 22

Preparation and Analysis of 116144

{[3-(4-bromo-1-methylpyrazol-3-yl)phenyl]amino}-N-(2-fluorophenyl)carboxamide

[Protocol A]—2-fluorophenyl isocyanate
colourless solid (DCM/hexane)
MS (ES+): m/z (%)=391 (M+H $^{81}$Br, 100), 389 (M+H $^{79}$Br, 90).
$^1$H-NMR (MeOH d$_4$): δ=3.79 (3H, s, NCH$_3$), 7.00–7.11 (4H, m, ArH), 7.40–7.56 (3H, m, ArH), 7.61 (1H, m, ArH), 8.09 (1H, m, ArH).
HPLC: retention time 3.01 min.

Experiment 23

Preparation and Analysis of 116145

2-({{[3-(4-bromo-1-methylpyrazol-3-yl)phenyl]amino}carbonylamino)benzamide

[Protocol B]—2-aminobenzamide
colourless solid (EtOAc/hexane)
MS (ES+): m/z (%)=399 (M+H—17 $^{81}$Br, 100), 397 (M+H—17 $^{79}$Br, 94).
$^1$H-NMR (DMSO d$_6$): δ=3.79 (3H, s, NCH$_3$), 6.93–7.10 (2H, m, ArH), 7.45 (2H, t, J=7.8, ArH), 7.59–7.72 (5H, m, ArH), 8.22 (2H, m), 9.92 (1H, s, NH), 10.69 (1H, s, NH).
HPLC: retention time 2.88 min.

Experiment 24

Preparation and Analysis of 116147

{[3-(4-bromo-1-methylpyrazol-3-yl)phenyl]amino}-N-(4-cyanophenyl)carboxamide

[Protocol B]—4-aminobenzonitrile
colourless solid (EtOAc/hexane)
MS (ES+): m/z (%)=398 (M+H $^{81}$Br, 100), 396 (M+H $^{79}$Br, 96).
$^1$H-NMR (MeOH d$_4$): δ=3.81 (3H, s, NCH$_3$), 7.12 (1H, m, ArH), 7.46–7.57 (3H, m, ArH), 7.62–7.69 (5H, m, ArH).
HPLC: retention time 3.12 min.

Experiment 25

Preparation and Analysis of 116148

{[3-(4-bromo-1-methylpyrazol-3-yl)phenyl]amino}-N-(2-cyanophenyl)carboxamide

[Protocol B]—2-aminobenzonitrile
colourless solid (EtOAc/hexane)
MS (ES+): m/z (%)=398 (M+H $^{81}$Br, 95), 396 (M+H $^{79}$Br, 100).
$^1$H-NMR (CDCl$_3$): δ=3.79 (3H, s, CH$_3$), 7.13–7.28 (2H, m, ArH), 7.49 (1H, t, J=7.8, ArH), 7.57 (1H, m, ArH), 7.62 (1H, m, ArH), 7.65–7.71 (2H, m, ArH), 7.78 (1H, m, ArH), 8.07 (1H, d, J=8.6, ArH), 8.83 (1H, s, NH), 9.62 (1H, s, NH).
HPLC: retention time 3.05 min [Method A].

Experiment 26

Preparation and Analysis of 116182

{[3-(4-bromo-1-methylpyrazol-3-yl)phenyl]amino}-N-(4-fluorophenylmethyl)carboxamide

[Protocol B]—4-fluorobenzylamine
colourless solid, m.p. 185.5–186.6° C. (EtOAc/hexane).
MS (ES+): m/z (%)=405 (M+H $^{81}$Br, 97), 403 (M+H $^{79}$Br, 100).

¹H-NMR (DMSO d₆): δ=3.75 (3H, s, CH₃), 4.28 (2H, d, J=6.0, CH₂), 6.73 (1H, t, J=5.9, NH), 7.01 (1H, d, J=7.5, ArH), 7.10–7.18 (2H, m, ArH), 7.27–7.41 (4H, m, ArH), 7.56 (1H, s, ArH), 7.62 (1H, s, ArH), 8.82 (1H, s, NH).

HPLC: retention time 3.10 min [Method A].

TLC: retention factor 0.25 (50% EtOAc/hexane).

Experiment 27

Preparation and Analysis of 116183

{[3-(4-bromo-1-methylpyrazol-3-yl)phenyl]amino}-N-(3,4-dimethoxyphenylmethyl)carboxamide

[Protocol B]—3,4-dimethoxybenzylamine colourless solid, m.p. 174.9–175.5° C. (EtOAc/hexane).

MS (CI+): m/z (%)=447 (M+H ⁸¹Br, 100), 445 (M+H ⁷⁹Br, 92).

¹H-NMR (DMSO d₆): δ=3.71 (3H, s, CH₃), 3.73 (3H, s, CH₃), 3.76 (3H, s, CH₃), 4.22 (2H, d, J=5.8, CH₂), 6.62 (1H, t, J=5.7, NH), 6.80 (1H, m, ArH), 6.89 (2H, m, ArH), 6.98 (1H, m, ArH), 7.36–7.51 (3H, m, ArH), 7.63 (1H, s, ArH), 8.76 (1H, s, NH).

HPLC: retention time 2.86 min [Method A].

TLC: retention factor 0.20 (50% EtOAc/hexane).

Experiment 28

Preparation and Analysis of 116184

{[3-(4-bromo-1-methylpyrazol-3-yl)phenyl]amino}-N-(3,4,5-trimethoxyphenylmethyl)carboxamide

[Protocol B]—3,4,5-trimethoxybenzylamine colourless solid (EtOAc/hexane).

MS (CI+): m/z (%)=477 (M+H ⁸¹Br, 100), 475 (M+H ⁷⁹Br, 95).

¹H-NMR (DMSO d₆): δ=3.63 (3H, s, OCH₃), 3.75 (9H, s, 3×CH₃), 4.21 (1H, d, J=5.9, CH₂), 6.61 (2H, s, ArH), 6.65 (1H, t, J=5.9, NH), 6.99 (1H, m, ArH), 7.40 (1H, t, J=7.7, ArH), 7.45 (1H, m, ArH), 7.56 (1H, m, ArH), 7.64 (1H, s, ArH), 8.77 (1H, s, NH).

HPLC: retention time 5.91 min [Method B].

TLC: retention factor 0.50 (50% EtOAc/hexane).

Experiment 29

Preparation and Analysis of 116185

{[3-(4-bromo-1-methylpyrazol-3-yl)phenyl]amino}-N-(2-methylphenylmethyl)carboxamide

[Protocol B]—2-methylbenzylamine colourless solid (EtOAc/hexane).

MS (CI+): m/z (%)=401 (M+H ⁸¹Br, 96), 399 (M+H ⁷⁹Br, 100).

¹H-NMR (DMSO d₆): δ=2.28 (3H, s, CH₃), 3.76 (3H, s, NCH₃), 4.28 (1H, d, J=5.8, CH₂), 6.60 (1H, t, J=5.8, NH), 7.01 (1H, m, ArH), 7.15 (3H, m, ArH), 7.24 (1H, m, ArH), 7.38–7.50 (2H, m, ArH), 7.57 (1H, m, ArH), 7.65 (1H, s, ArH), 8.77 (1H, s, NH).

HPLC: retention time 2.74 min [Method A].

TLC: retention factor 0.20 (50% EtOAc/hexane).

Experiment 30

Preparation and Analysis of 116189

{[3-(4-bromo-1-methylpyrazol-3-yl)phenyl]amino}-N-(4-methoxyphenylmethyl)carboxamide

[Protocol B]—4-methoxybenzylamine colourless solid (EtOAc/hexane).

MS (CI+): m/z (%)=417 (M+H ⁸¹Br, 94), 415 (M+H ⁷⁹Br, 100).

¹H-NMR (DMSO d₆): δ=3.72 (3H, s, CH₃), 3.77 (3H, s, NCH₃), 4.22 (1H, d, J=5.9, CH₂), 6.62 (1H, t, J=5.9, NH), 6.90 (2H, d, J=8.8, ArH), 7.00 (1H, m, ArH), 7.23 (2H, d, J=8.8, ArH), 7.39 (1H, t, J=7.8, ArH), 7.43 (1H, m, ArH), 7.56 (1H, m, ArH), 7.64 (1H, s, ArH), 8.73 (1H, s, NH).

HPLC: retention time 6.41 min [Method B].

TLC: retention factor 0.25 (50% EtOAc/hexane).

Experiment 31

Preparation and Analysis of 116194

{[3-(4-bromo-1-methylpyrazol-3-yl)phenyl]amino}-N-[2-(4-methoxy)phenylethyl]carboxamide

[Protocol B]—2-(4-methoxyphenyl)ethylamine colourless solid (EtOAc/hexane).

MS (ES+): m/z (%)=431 (M+H ⁸¹Br, 95), 429 (M+H ⁷⁹Br, 100).

¹H-NMR (DMSO d₆): δ=2.68 (2H, t, J=7.1, CH₂), 3.31 (2H, m, CH₂), 3.71 (3H, s, CH₃), 3.77 (3H, s, CH₃), 6.16 (1H, t, J=5.8, NH), 6.87 (2H, d, J=8.6, ArH), 6.99 (1H, dt, J=1.4, 7.3, ArH), 7.16 (2H, d, J=8.6, ArH), 7.33–7.48 (2H, m, ArH), 7.52 (1H, m, ArH), 7.63 (1H, s, ArH), 8.71 (1H, s, NH).

HPLC: retention time 6.62 min [Method B].

An important point that can be derived from the foregoing data is that by using a constitutively activated form of the receptor in the direct identification of candidate compounds, the selectivity of the compounds is exceptional: as those in the art appreciate, the homology between the human $5HT_{2A}$ and $5HT_{2C}$ receptors is about 95%, and even with such homology, certain of the directly identified compounds, e.g., 116081 and 116082 evidence a 100-fold difference in selectivity preference (as measured by $IC_{50}$ values) for the $5HT_{2A}$ receptor compared with the $5HT_{2C}$ receptor. This is important for pharmaceutical compositions in that such selectivity can help to reduce side-effects associated with interaction of a drug with a non-target receptor.

Different embodiments of the invention will consist of different constitutively activated receptors, different expression systems, different assays, and different compounds. Those skilled in the art will understand which receptors to use with which expression systems and assay methods. All are considered within the scope of the teaching of this invention. In addition, those skilled in the art will recognize that various modifications, additions, substitutions, and variations to the illustrative examples set forth herein can be made without departing from the spirit of the invention and are, therefore, considered within the scope of the invention. All documents referenced above, including, but not limited to, provisional and regular patent applications, are fully incorporated herein by reference.

We claim:

1. A compound structurally represented as follows:

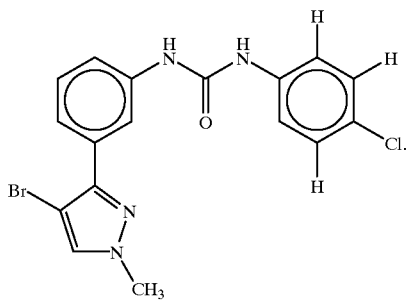

2. A compound structurally represented as follows:

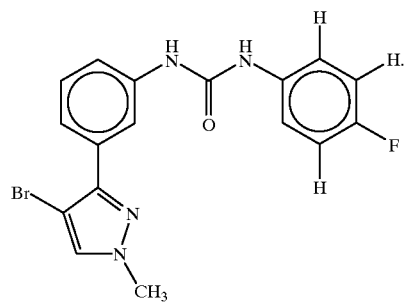

3. A composition comprising the compound of claim 1.
4. A composition comprising the compound of claim 2.
5. A compound structurally represented as follows:

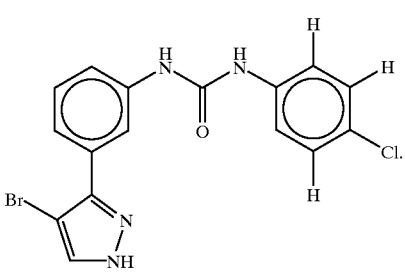

6. A compound structurally represented as follows:

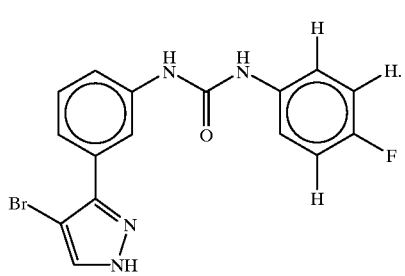

7. A composition comprising the compound of claim 5.
8. A composition comprising the compound of claim 6.

9. A compound structurally represented as follows:

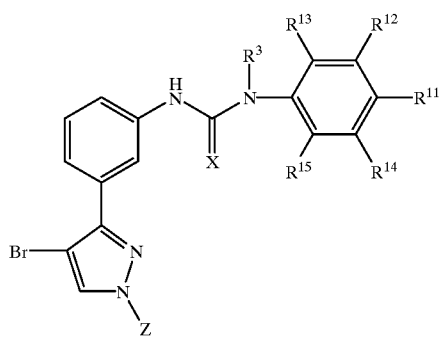

wherein:

X is O or S;

Z is H or $CH_3$;

$R^3$ and $R^{10}$ are each independently selected from H, $C_{1-8}$ straight chain or branched alkyl, $C_{3-8}$ cycloalkyl, $C_{4-9}$ alkylcycloalkyl, and $C_{2-8}$ alkenyl;

$R^{11}$ is H, F, Cl, Br, I, $R^7$, $CF_3$, $CCl_3$, $NR^8R^9$, $NR^{10}COR^7$, $NR^{10}SO_2R^7$, $OR^7$, $OCF_3$, $OCOR^7$, $OSO_2R^7$, $SR^7$, $SCF_3$, $SCOR^7$, $SO_3R^7$, $SO_2NR^8R^9$, $NO_2$, CN, $COOR^7$, $COSR^7$, or $CONR^8R^9$, with the proviso that when a position adjacent to $R^{11}$ is substituted, then $R^{11}$ and said adjacent position can together be selected from $SCH_2S$, $SCH_2CH_2S$, $OCH_2O$, and $OCH_2CH_2O$ to form a bi-cyclic structure;

$R^7$ is H, $C_{1-8}$ straight chain or branched alkyl, $C_{3-8}$ cycloalkyl, $C_{4-9}$ alkylcycloalkyl, $C_{2-8}$ alkenyl, aryl or alkylaryl;

$R^8$ and $R^9$ are independently selected from H, $C_{1-8}$ straight chain or branched alkyl, and $C_{2-8}$ alkenyl or cycloalkyl, or alkylcycloalkyl, or aryl or $CH_2$aryl wherein each moiety within said $C_{1-8}$ straight chain or branched alkyl, $C_{2-8}$ alkenyl or cycloalkyl, or alkylcycloalkyl, or aryl or $CH_2$aryl may be optionally substituted by up to four substituents in any position, whereby each substituent is independently selected from: F, Cl, Br, I, $CF_3$, $CCl_3$, $CH_3$, $C_2H_5$, $C_3H_7$, $C_4H_9$, $NH_2$, $NHCH_3$, $N(CH_3)_2$, $NHC_2H_5$, $N(C_2H_5)_2$, $NHC_3H_7$, $N(C_3H_7)_2$, $NHC_4H_9$, $N(C_4H_9)_2$, NHCOH, $NHCOCH_3$, $NHCOC_2H_5$, $NHCOC_3H_7$, $NHCOC_4H_9$, $NHSO_2CH_3$, $NHSO_2C_2H_5$, $NHSO_2C_3H_7$, $NHSO_2C_4H_9$, OH, $OCH_3$, $OC_2H_5$, $OC_3H_7$, $OC_4H_7$, $OC_4H_9$, $OC_5H_9$, $OC_5H_{11}$, $OC_6H_{11}$, $OC_6H_{13}$, $OCF_3$, $OCOCH_3$, $OCOC_2H_5$, $OCOC_3H_7$, $OCOC_4H_9$, $OSO_2CH_3$, $OSO_2C_2H_5$, $OSO_2C_3H_7$, $OSO_2C_4H_9$, SH, $SCH_3$, $SC_2H_5$, $SC_3H_7$, $SC_4H_7$, $SC_4H_9$, $SC_5H_9$, $SC_5H_{11}$, $SC_6H_{11}$, $SC_6H_{13}$, $SCF_3$, $SCOCH_3$, $SCOC_2H_5$, $SCOC_3H_7$, $SCOC_4H_9$, $SO_3CH_3$, $SO_3C_2H_5$, $SO_3C_3H_7$, $SO_3C_4H_9$, $SO_2NH$, $SO_2NH_2$, $SO_2NHCH_3$, $SO_2N(CH_3)_2$, $SO_2NHC_2H_5$, $SO_2N(C_2H_5)_2$, $SO_2NHC_3H_7$, $SO_2N(C_3H_7)_2$, $SO_2NHC_4H_9$, $SO_2N(C_4H_9)_2$, $NO_2$, CN, $COOCH_3$, $COOC_2H_5$, $COOC_3H_7$, $COOC_4H_9$, $COSCH_3$, $COSC_2H_5$, $COSC_3H_7$, $COSC_4H_9$, $CONH_2$, $CONHCH_3$, $CON(CH_3)_2$, $CONHC_2H_5$, $CON(C_2H_5)_2$, $CONHC_3H_7$, $CON(C_3H_7)_2$, $CONHC_4H_9$, and $CON(C_4H_9)_2$, and with the proviso that when either of $R^8$ or $R^9$ contain an aryl ring substituted at at least two adjacent positions on said aryl ring, then said two adjacent positions can together be selected from $SCH_2S$, $SCH_2CH_2S$, $OCH_2O$, or $OCH_2CH_2O$ to form a bi-cyclic structure;

$R^{12}$, $R^{13}$, $R^{14}$, and $R^{15}$ are each independently selected from: F, Cl, Br, I, $CF_3$, $CCl_3$, $CH_3$, $C_2H_5$, $C_3H_7$, $C_4H_9$, $NH_2$, $NHCH_3$, $N(CH_3)_2$, $NHC_2H_5$, $N(C_2H_5)_2$, $NHC_3H_7$, $N(C_3H_7)_2$, $NHC_4H_9$, $N(C_4H_9)_2$, NHCOH, $NHCOCH_3$, $NHCOC_2H_5$, $NHCOC_3H_7$, $NHCOC_4H_9$, $NHSO_2CH_3$, $NHSO_2C_2H_5$, $NHSO_2C_3H_7$, $NHSO_2C_4H_9$, OH, $OCH_3$, $OC_2H_5$, $OC_3H_7$, $OC_4H_7$, $OC_4H_9$, $OC_5H_9$, $OC_5H_{11}$, $OC_6H_{11}$, $OC_6H_{13}$, $OCF_3$, $OCOCH_3$, $OCOC_2H_5$, $OCOC_3H_7$, $OCOC_4H_9$, $OSO_2CH_3$, $OSO_2C_2H_5$, $OSO_2C_3H_7$, $OSO_2C_4H_9$, SH, $SCH_3$, $SC_2H_5$, $SC_3H_7$, $SC_4H_7$, $SC_4H_9$, $SC_5H_9$, $SC_5H_{11}$, $SC_6H_{11}$, $SC_6H_{13}$, $SCF_3$, $SCOCH_3$, $SCOC_2H_5$, $SCOC_3H_7$, $SCOC_4H_9$, $SO_3CH_3$, $SO_3C_2H_5$, $SO_3C_3H_7$, $SO_3C_4H_9$, $SO_2NH$, $SO_2NH_2$, $SO_2NHCH_3$, $SO_2N(CH_3)_2$, $SO_2NHC_2H_5$, $SO_2N(C_2H_5)_2$, $SO_2NHC_3H_7$, $SO_2N(C_3H_7)_2$, $SO_2NHC_4H_9$, $SO_2N(C_4H_9)_2$, $NO_2$, CN, $COOCH_3$, $COOC_2H_5$, $COOC_3H_7$, $COOC_4H_9$, $COSCH_3$, $COSC_2H_5$, $COSC_3H_7$, $COSC_4H_9$, $CONH_2$, $CONHCH_3$, $CON(CH_3)_2$, $CONHC_2H_5$, $CON(C_2H_5)_2$, $CONHC_3H_7$, $CON(C_3H_7)_2$, $CONHC_4H_9$, and $CON(C_4H_9)_2$, and with the proviso that when any two adjacent positions of $R^{12}$, $R^{13}$, $R^{14}$, and $R^{15}$ are substituted, said two adjacent positions can together be further selected from $SCH_2S$, $SCH_2CH_2S$, $OCH_2O$, and $OCH_2CH_2O$ to form a bi-cyclic structure; and with the proviso that at least two of $R^{12}$, $R^{13}$, $R^{14}$, and $R^{15}$ must be H.

10. The compound of claim 9 structurally represented as follows:

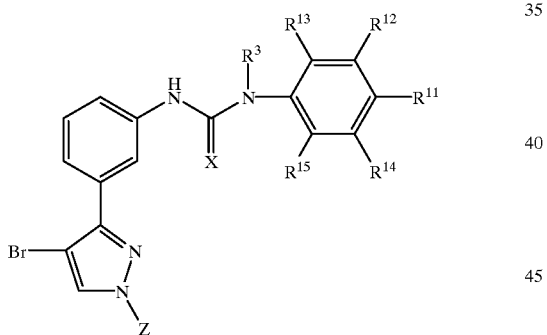

wherein:

X is O or S;

Z is H or $CH_3$;

$R^3$ and $R^{10}$ are each independently selected from H, $C_{1-8}$ straight chain or branched alkyl, $C_{3-8}$ cycloalkyl, $C_{4-9}$ alkylcycloalkyl, and $C_{2-8}$ alkenyl;

$R^{11}$ is H, F, Cl, Br, I, $R^7$, $CF_3$, $CCl_3$, $NR^8R^9$, $NR^{10}COR^7$, $NR^{10}SO_2R^7$, $OR^7$, $OCF_3$, $OCOR^7$, $OSO_2R^7$, $SR^7$, $SCF_3$, $SCOR^7$, $SO_3R^7$, $SO_2NR^8R^9$, $NO_2$, CN, $COOR^7$, $COSR^7$, or $CONR^8R^9$, with the proviso that when a position adjacent to $R^{11}$ is substituted, then $R^{11}$ and said adjacent position can together be selected from $SCH_2S$, $SCH_2CH_2S$, $OCH_2O$, or $OCH_2CH_2O$ to form a bi-cyclic structure;

$R^7$ is H, $C_{1-8}$ straight chain or branched alkyl, $C_{3-8}$ cycloalkyl, $C_{4-9}$ alkylcycloalkyl, $C_{2-8}$ alkenyl, aryl or alkylaryl;

$R^8$ and $R^9$ are independently selected from H, $C_{1-8}$ straight chain or branched alkyl, and $C_{2-8}$ alkenyl or cycloalkyl, or alkylcycloalkyl, or aryl or $CH_2$aryl wherein each moiety within said $C_{1-8}$ straight chain or branched alkyl, $C_{2-8}$ alkenyl or cycloalkyl, or alkylcycloalkyl, or aryl or $CH_2$aryl may be optionally substituted by up to four substituents in any position, whereby each substituent is independently selected from: F, Cl, Br, I, $CF_3$, $CCl_3$, $CH_3$, $C_2H_5$, $C_3H_7$, $C_4H_9$, $NH_2$, $NHCH_3$, $N(CH_3)_2$, $NHC_2H_5$, $N(C_2H_5)_2$, $NHC_3H_7$, $N(C_3H_7)_2$, $NHC_4H_9$, $N(C_4H_9)_2$, NHCOH, $NHCOCH_3$, $NHCOC_2H_5$, $NHCOC_3H_7$, $NHCOC_4H_9$, $NHSO_2CH_3$, $NHSO_2C_2H_5$, $NHSO_2C_3H_7$, $NHSO_2C_4H_9$, OH, $OCH_3$, $OC_2H_5$, $OC_3H_7$, $OC_4H_7$, $OC_4H_9$, $OC_5H_9$, $OC_5H_{11}$, $OC_6H_{11}$, $OC_6H_{13}$, $OCF_3$, $OCOCH_3$, $OCOC_2H_5$, $OCOC_3H_7$, $OCOC_4H_9$, $OSO_2CH_3$, $OSO_2C_2H_5$, $OSO_2C_3H_7$, $OSO_2C_4H_9$, SH, $SCH_3$, $SC_2H_5$, $SC_3H_7$, $SC_4H_7$, $SC_4H_9$, $SC_5H_9$, $SC_5H_{11}$, $SC_6H_{11}$, $SC_6H_{13}$, $SCF_3$, $SCOCH_3$, $SCOC_2H_5$, $SCOC_3H_7$, $SCOC_4H_9$, $SO_3CH_3$, $SO_3C_2H_5$, $SO_3C_3H_7$, $SO_3C_4H_9$, $SO_2NH$, $SO_2NH_2$, $SO_2NHCH_3$, $SO_2N(CH_3)_2$, $SO_2NHC_2H_5$, $SO_2N(C_2H_5)_2$, $SO_2NHC_3H_7$, $SO_2N(C_3H_7)_2$, $SO_2NHC_4H_9$, $SO_2N(C_4H_9)_2$, $NO_2$, CN, $COOCH_3$, $COOC_2H_5$, $COOC_3H_7$, $COOC_4H_9$, $COSCH_3$, $COSC_2H_5$, $COSC_3H_7$, $COSC_4H_9$, $CONH_2$, $CONHCH_3$, $CON(CH_3)_2$, $CONHC_2H_5$, $CON(C_2H_5)_2$, $CONHC_3H_7$, $CON(C_3H_7)_2$, $CONHC_4H_9$, and $CON(C_4H_9)_2$, and with the proviso that when either of $R^8$ or $R^9$ contain an aryl ring substituted at at least two adjacent positions on said aryl ring, then said two adjacent positions can together be selected from $SCH_2S$, $SCH_2CH_2S$, $OCH_2O$, and $OCH_2CH_2O$ to form a bi-cyclic structure;

$R^{12}$, $R^{13}$, $R^{14}$, and $R^{15}$ are each independently selected from: F, Cl, Br, I, $CF_3$, $CCl_3$, $CH_3$, $C_2H_5$, $C_3H_7$, $C_4H_9$, $NH_2$, $NHCH_3$, $N(CH_3)_2$, $NHC_2H_5$, $N(C_2H_5)_2$, $NHC_3H_7$, $N(C_3H_7)_2$, $NHC_4H_9$, $N(C_4H_9)_2$, NHCOH, $NHCOCH_3$, $NHCOC_2H_5$, $NHCOC_3H_7$, $NHCOC_4H_9$, $NHSO_2CH_3$, $NHSO_2C_2H_5$, $NHSO_2C_3H_7$, $NHSO_2C_4H_9$, OH, $OCH_3$, $OC_2H_5$, $OC_3H_7$, $OC_4H_7$, $OC_4H_9$, $OC_5H_9$, $OC_5H_{11}$, $OC_6H_{11}$, $OC_6H_{13}$, $OCF_3$, $OCOCH_3$, $OCOC_2H_5$, $OCOC_3H_7$, $OCOC_4H_9$, $OSO_2CH_3$, $OSO_2C_2H_5$, $OSO_2C_3H_7$, $OSO_2C_4H_9$, SH, $SCH_3$, $SC_2H_5$, $SC_3H_7$, $SC_4H_7$, $SC_4H_9$, $SC_5H_9$, $SC_5H_{11}$, $SC_6H_{11}$, $SC_6H_{13}$, $SCF_3$, $SCOCH_3$, $SCOC_2H_5$, $SCOC_3H_7$, $SCOC_4H_9$, $SO_3CH_3$, $SO_3C_2H_5$, $SO_3C_3H_7$, $SO_3C_4H_9$, $SO_2NH$, $SO_2NH_2$, $SO_2NHCH_3$, $SO_2N(CH_3)_2$, $SO_2NHC_2H_5$, $SO_2N(C_2H_5)_2$, $SO_2NHC_3H_7$, $SO_2N(C_3H_7)_2$, $SO_2NHC_4H_9$, $SO_2N(C_4H_9)_2$, $NO_2$, CN, $COOCH_3$, $COOC_2H_5$, $COOC_3H_7$, $COOC_4H_9$, $COSCH_3$, $COSC_2H_5$, $COSC_3H_7$, $COSC_4H_9$, $CONH_2$, $CONHCH_3$, $CON(CH_3)_2$, $CONHC_2H_5$, $CON(C_2H_5)_2$, $CONHC_3H_7$, $CON(C_3H_7)_2$, $CONHC_4H_9$, and $CON(C_4H_9)_2$, and with the proviso that when any two adjacent positions of $R^{12}$, $R^{13}$, $R^{14}$, and $R^{15}$ are substituted, said two adjacent positions can together be further selected from $SCH_2S$, $SCH_2CH_2S$, $OCH_2O$, and $OCH_2CH_2O$ to form a bi-cyclic structure; and with the proviso that at least two of $R^{12}$, $R^{13}$, $R^{14}$, and $R^{15}$ must be H.

11. A composition comprising a compound of claim 9.

12. A composition comprising a compound of claim 10.

* * * * *

SEQUENCE LISTING (1) GENERAL INFORMATION:

(iii) NUMBER OF SEQUENCES: 27

(2) INFORMATION FOR SEQ ID NO:1:

(i) SEQUENCE CHARACTERISTICS:
       (A) LENGTH: 28 base pairs
       (B) TYPE: nucleic acid
       (C) STRANDEDNESS: single
       (D) TOPOLOGY: linear (ii) MOLECULE TYPE: DNA (genomic)

(iv) ANTI-SENSE: NO (xi) SEQUENCE DESCRIPTION: SEQ ID NO:1:

GACCTCGAGG TTGCTTAAGA CTGAAGCA                                       28

(2) INFORMATION FOR SEQ ID NO:2:

(i) SEQUENCE CHARACTERISTICS:
       (A) LENGTH: 28 base pairs
       (B) TYPE: nucleic acid
       (C) STRANDEDNESS: single
       (D) TOPOLOGY: linear (ii) MOLECULE TYPE: DNA (genomic)

(iv) ANTI-SENSE: YES (xi) SEQUENCE DESCRIPTION: SEQ ID NO:2:

ATTTCTAGAC ATATGTAGCT TGTACCGT                                       28

(2) INFORMATION FOR SEQ ID NO:3:

(i) SEQUENCE CHARACTERISTICS:
       (A) LENGTH: 50 base pairs
       (B) TYPE: nucleic acid
       (C) STRANDEDNESS: single
       (D) TOPOLOGY: linear (ii) MOLECULE TYPE: DNA (genomic)

(iv) ANTI-SENSE: NO (xi) SEQUENCE DESCRIPTION: SEQ ID NO:3:

CTAGGGGCAC CATGCAGGCT ATCAACAATG AAAGAAAAGC TAAGAAAGTC               50

(2) INFORMATION FOR SEQ ID NO:4:

(i) SEQUENCE CHARACTERISTICS:
       (A) LENGTH: 50 base pairs
       (B) TYPE: nucleic acid
       (C) STRANDEDNESS: single
       (D) TOPOLOGY: linear (ii) MOLECULE TYPE: DNA (genomic)

(iv) ANTI-SENSE: YES (xi) SEQUENCE DESCRIPTION: SEQ ID NO:4:

CAAGGACTTT CTTAGCTTTT CTTTCATTGT TGATAGCCTG CATGGTGCCC               50

(2) INFORMATION FOR SEQ ID NO:5:

(i) SEQUENCE CHARACTERISTICS:

(A) LENGTH: 26 base pairs
        (B) TYPE: nucleic acid
        (C) STRANDEDNESS: single
        (D) TOPOLOGY: linear (ii) MOLECULE TYPE: DNA (genomic)

(iv) ANTI-SENSE: NO (xi) SEQUENCE DESCRIPTION: SEQ ID NO:5:

GACCTCGAGT CCTTCTACAC CTCATC                            26

(2) INFORMATION FOR SEQ ID NO:6:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(iv) ANTI-SENSE: YES (xi) SEQUENCE DESCRIPTION: SEQ ID NO:6:

TGCTCTAGAT TCCAGATAGG TGAAAACTTG                         30

(2) INFORMATION FOR SEQ ID NO:7:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(iv) ANTI-SENSE: YES (xi) SEQUENCE DESCRIPTION: SEQ ID NO:7:

CAAAGAAAGT ACTGGGCATC GTCTTCTTCC T                       31

(2) INFORMATION FOR SEQ ID NO:8:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(iv) ANTI-SENSE: NO (xi) SEQUENCE DESCRIPTION: SEQ ID NO:8:

CCGCTCGAGT ACTGCGCCGA CAAGCTTTGA T                       31

(2) INFORMATION FOR SEQ ID NO:9:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (genomic)

(iv) ANTI-SENSE: YES (xi) SEQUENCE DESCRIPTION: SEQ ID NO:9:

-continued

```
CGATGCCCAG CACTTTCGAA GCTTTTCTTT CATTGTTG                    38
```

(2) INFORMATION FOR SEQ ID NO:10:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(iv) ANTI-SENSE: NO (xi) SEQUENCE DESCRIPTION: SEQ ID NO:10:

```
AAAAGCTTCG AAAGTGCTGG GCATCGTCTT CTTCCT                      36
```

(2) INFORMATION FOR SEQ ID NO:11:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(iv) ANTI-SENSE: YES (xi) SEQUENCE DESCRIPTION: SEQ ID NO:11:

```
TGCTCTAGAT TCCAGATAGG TGAAAACTTG                             30
```

(2) INFORMATION FOR SEQ ID NO:12:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iv) ANTI-SENSE: NO (xi) SEQUENCE DESCRIPTION: SEQ ID NO:12:

```
CGTGTCTCTC CTTACTTCA                                         19
```

(2) INFORMATION FOR SEQ ID NO:13:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(iv) ANTI-SENSE: YES (xi) SEQUENCE DESCRIPTION: SEQ ID NO:13:

```
TCGGCGCAGT ACTTTGATAG TTAGAAAGTA GGTGAT                      36
```

(2) INFORMATION FOR SEQ ID NO:14:

(i) SEQUENCE CHARACTERISTICS:
        (A) LENGTH: 38 base pairs
        (B) TYPE: nucleic acid
        (C) STRANDEDNESS: single
        (D) TOPOLOGY: linear -continued (ii) MOLECULE TYPE: DNA (genomic)

(iv) ANTI-SENSE: NO (xi) SEQUENCE DESCRIPTION: SEQ ID NO:14:

TTCTAACTAT CAAAGTACTG CGCCGACAAG CTTTGATG                      38

(2) INFORMATION FOR SEQ ID NO:15:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (genomic)

(iv) ANTI-SENSE: NO (xi) SEQUENCE DESCRIPTION: SEQ ID NO:15:

TTCAGCAGTC AACCCACTAG TCTATACTCT GTTCAACAAA ATT                43

(2) INFORMATION FOR SEQ ID NO:16:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(iv) ANTI-SENSE: YES (xi) SEQUENCE DESCRIPTION: SEQ ID NO:16:

ATTTCTAGAC ATATGTAGCT TGTACCGT                                28

(2) INFORMATION FOR SEQ ID NO:17:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iv) ANTI-SENSE: NO (xi) SEQUENCE DESCRIPTION: SEQ ID NO:17:

ATCACCTACT TTCTAACTA                                        19

(2) INFORMATION FOR SEQ ID NO:18:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(iv) ANTI-SENSE: YES (xi) SEQUENCE DESCRIPTION: SEQ ID NO:18:

CCATAATCGT CAGGGGAATG AAAAATGACA CAA                          33

(2) INFORMATION FOR SEQ ID NO:19:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: DNA (genomic)

(iv) ANTI-SENSE: NO (xi) SEQUENCE DESCRIPTION: SEQ ID NO:19:

ATTTTTCATT CCCCTGACGA TTATGGTGAT TAC                              33

(2) INFORMATION FOR SEQ ID NO:20:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: DNA (genomic)

(iv) ANTI-SENSE: YES (xi) SEQUENCE DESCRIPTION: SEQ ID NO:20:

TGATGAAGAA AGGGCACCAC ATGATCAGAA ACA                              33

(2) INFORMATION FOR SEQ ID NO:21:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: DNA (genomic)

(iv) ANTI-SENSE: NO (xi) SEQUENCE DESCRIPTION: SEQ ID NO:21:

GATCATGTGG TGCCCTTTCT TCATCACAAA CAT                              33

(2) INFORMATION FOR SEQ ID NO:22:

(i) SEQUENCE CHARACTERISTICS:
            (A) LENGTH: 1377 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:22:

ATGGTGAACC TGAGGAATGC GGTGCATTCA TTCCTTGTGC ACCTAATTGG CCTATTGGTT     60

TGGCAATGTG ATATTTCTGT GAGCCCAGTA GCAGCTATAG TAACTGACAT TTTCAATACC    120

TCCGATGGTG GACGCTTCAA ATTCCCAGAC GGGGTACAAA ACTGGCCAGC ACTTTCAATC    180

GTCATCATAA TAATCATGAC AATAGGTGGC AACATCCTTG TGATCATGGC AGTAAGCATG    240

GAAAAGAAAC TGCACAATGC CACCAATTAC TTCTTAATGT CCCTAGCCAT TGCTGATATG    300

CTAGTGGGAC TACTTGTCAT GCCCCTGTCT CTCCTGGCAA TCCTTTATGA TTATGTCTGG    360

CCACTACCTA GATATTTGTG CCCCGTCTGG ATTTCTTTAG ATGTTTTATT TTCAACAGCG    420

TCCATCATGC ACCTCTGCGC TATATCGCTG GATCGGTATG TAGCAATACG TAATCCTATT    480

GAGCATAGCC GTTTCAATTC GCGGACTAAG GCCATCATGA AGATTGCTAT TGTTTGGGCA    540

```
ATTTCTATAG GTGTATCAGT TCCTATCCCT GTGATTGGAC TGAGGGACGA AGAAAAGGTG      600

TTCGTGAACA ACACGACGTG CGTGCTCAAC GACCCAAATT TCGTTCTTAT TGGGTCCTTC      660

GTAGCTTTCT TCATACCGCT GACGATTATG GTGATTACGT ATTGCCTGAC CATCTACGTT      720

CTGCGCCGAC AAGCTTTGAT GTTACTGCAC GGCCACACCG AGGAACCGCC TGGACTAAGT      780

CTGGATTTCC TGAAGTGCTG CAAGAGGAAT ACGGCCGAGG AAGAGAACTC TGCAAACCCT      840

AACCAAGACC AGAACGCACG CCGAAGAAAG AAGAAGGAGA GACGTCCTAG GGGCACCATG      900

CAGGCTATCA ACAATGAAAG AAAAGCTAAG AAAGTCCTTG GGATTGTTTT CTTTGTGTTT      960

CTGATCATGT GGTGCCCATT TTTCATTACC AATATTCTGT CTGTTCTTTG TGAGAAGTCC     1020

TGTAACCAAA AGCTCATGGA AAAGCTTCTG AATGTGTTTG TTTGGATTGG CTATGTTTGT     1080

TCAGGAATCA ATCCTCTGGT GTATACTCTG TTCAACAAAA TTTACCGAAG GCATTCTCC      1140

AACTATTTGC GTTGCAATTA TAAGGTAGAG AAAAAGCCTC CTGTCAGGCA GATTCCAAGA     1200

GTTGCCGCCA CTGCTTTGTC TGGGAGGGAG CTTAATGTTA ACATTTATCG GCATACCAAT     1260

GAACCGGTGA TCGAGAAAGC CAGTGACAAT GAGCCCGGTA TAGAGATGCA AGTTGAGAAT     1320

TTAGAGTTAC CAGTAAATCC CTCCAGTGTG GTTAGCGAAA GGATTAGCAG TGTGTGA      1377
```

(2) INFORMATION FOR SEQ ID NO:23:

(i) SEQUENCE CHARACTERISTICS:
        (A) LENGTH: 458 amino acids
        (B) TYPE: amino acid
        (C) STRANDEDNESS:
        (D) TOPOLOGY: Not Relevant (ii) MOLECULE TYPE: protein (xi) SEQUENCE DESCRIPTION: SEQ ID NO:23:

```
Met Val Asn Leu Arg Asn Ala Val His Ser Phe Leu Val His Leu Ile
1               5                  10                  15

Gly Leu Leu Val Trp Gln Cys Asp Ile Ser Val Ser Pro Val Ala Ala
                20                  25                  30

Ile Val Thr Asp Ile Phe Asn Thr Ser Asp Gly Gly Arg Phe Lys Phe
            35                  40                  45

Pro Asp Gly Val Gln Asn Trp Pro Ala Leu Ser Ile Val Ile Ile
        50                  55                  60

Ile Met Thr Ile Gly Gly Asn Ile Leu Val Ile Met Ala Val Ser Met
65                  70                  75                  80

Glu Lys Lys Leu His Asn Ala Thr Asn Tyr Phe Leu Met Ser Leu Ala
                85                  90                  95

Ile Ala Asp Met Leu Val Gly Leu Leu Val Met Pro Leu Ser Leu Leu
            100                 105                 110

Ala Ile Leu Tyr Asp Tyr Val Trp Pro Leu Pro Arg Tyr Leu Cys Pro
        115                 120                 125

Val Trp Ile Ser Leu Asp Val Leu Phe Ser Thr Ala Ser Ile Met His
    130                 135                 140

Leu Cys Ala Ile Ser Leu Asp Arg Tyr Val Ala Ile Arg Asn Pro Ile
145                 150                 155                 160

Glu His Ser Arg Phe Asn Ser Arg Thr Lys Ala Ile Met Lys Ile Ala
                165                 170                 175

Ile Val Trp Ala Ile Ser Ile Gly Val Ser Val Pro Ile Pro Val Ile
            180                 185                 190

Gly Leu Arg Asp Glu Glu Lys Val Phe Val Asn Asn Thr Thr Cys Val
        195                 200                 205
```

```
Leu Asn Asp Pro Asn Phe Val Leu Ile Gly Ser Phe Val Ala Phe Phe
    210                 215                 220
Ile Pro Leu Thr Ile Met Val Ile Thr Tyr Cys Leu Thr Ile Tyr Val
225                 230                 235                 240
Leu Arg Arg Gln Ala Leu Met Leu Leu His Gly His Thr Glu Glu Pro
                245                 250                 255
Pro Gly Leu Ser Leu Asp Phe Leu Lys Cys Cys Lys Arg Asn Thr Ala
                260                 265                 270
Glu Glu Glu Asn Ser Ala Asn Pro Asn Gln Asp Gln Asn Ala Arg Arg
                275                 280                 285
Arg Lys Lys Lys Glu Arg Arg Pro Arg Gly Thr Met Gln Ala Ile Asn
    290                 295                 300
Asn Glu Arg Lys Ala Lys Lys Val Leu Gly Ile Val Phe Phe Val Phe
305                 310                 315                 320
Leu Ile Met Trp Cys Pro Phe Phe Ile Thr Asn Ile Leu Ser Val Leu
                325                 330                 335
Cys Glu Lys Ser Cys Asn Gln Lys Leu Met Glu Lys Leu Leu Asn Val
                340                 345                 350
Phe Val Trp Ile Gly Tyr Val Cys Ser Gly Ile Asn Pro Leu Val Tyr
                355                 360                 365
Thr Leu Phe Asn Lys Ile Tyr Arg Arg Ala Phe Ser Asn Tyr Leu Arg
    370                 375                 380
Cys Asn Tyr Lys Val Glu Lys Lys Pro Pro Val Arg Gln Ile Pro Arg
385                 390                 395                 400
Val Ala Ala Thr Ala Leu Ser Gly Arg Glu Leu Asn Val Asn Ile Tyr
                405                 410                 415
Arg His Thr Asn Glu Pro Val Ile Glu Lys Ala Ser Asp Asn Glu Pro
                420                 425                 430
Gly Ile Glu Met Gln Val Glu Asn Leu Glu Leu Pro Val Asn Pro Ser
                435                 440                 445
Ser Val Val Ser Glu Arg Ile Ser Ser Val
    450                 455
```

(2) INFORMATION FOR SEQ ID NO:24:

(i) SEQUENCE CHARACTERISTICS:
        (A) LENGTH: 1437 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:24:

```
ATGGATATTC TTTGTGAAGA AAATACTTCT TTGAGCTCAA CTACGAACTC CCTAATGCAA      60

TTAAATGATG ACAACAGGCT CTACAGTAAT GACTTTAACT CCGGAGAAGC TAACACTTCT     120

GATGCATTTA ACTGGACAGT CGACTCTGAA AATCGAACCA ACCTTTCCTG TGAAGGGTGC     180

CTCTCACCGT CGTGTCTCTC CTTACTTCAT CTCCAGGAAA AAACTGGTC TGCTTTACTG      240

ACAGCCGTAG TGATTATTCT AACTATTGCT GGAAACATAC TCGTCATCAT GGCAGTGTCC     300

CTAGAGAAAA AGCTGCAGAA TGCCACCAAC TATTTCCTGA TGTCACTTGC CATAGCTGAT     360

ATGCTGCTGG GTTTCCTTGT CATGCCCGTG TCCATGTTAA CCATCCTGTA TGGGTACCGG     420

TGGCCTCTGC CGAGCAAGCT TTGTGCAGTC TGGATTTACC TGGACGTGCT CTTCTCCACG     480

GCCTCCATCA TGCACCTCTG CGCCATCTCG CTGGACCGCT ACGTCGCCAT CCAGAATCCC     540
```

-continued

```
ATCCACCACA GCCGCTTCAA CTCCAGAACT AAGGCATTTC TGAAAATCAT TGCTGTTTGG      600

ACCATATCAG TAGGTATATC CATGCCAATA CCAGTCTTTG GGCTACAGGA CGATTCGAAG      660

GTCTTTAAGG AGGGGAGTTG CTTACTCGCC GATGATAACT TTGTCCTGAT CGGCTCTTTT      720

GTGTCATTTT TCATTCCCTT AACCATCATG GTGATCACCT ACTTTCTAAC TATCAAGGTT      780

CTGCGCCGAC AAGCTTTGAT GTTACTGCAC GGCCACACCG AGGAACCGCC TGGACTAAGT      840

CTGGATTTCC TGAAGTGCTG CAAGAGGAAT ACGGCCGAGG AAGAGAACTC TGCAAACCCT      900

AACCAAGACC AGAACGCACG CCGAAGAAAG AAGAAGGAGA GACGTCCTAG GGGCACCATG      960

CAGGCTATCA ACAATGAAAG AAAAGCTTCG AAGGTACTGG GCATCGTCTT CTTCCTGTTT     1020

GTGGTGATGT GGTGCCCTTT CTTCATCACA ACATCATGG CCGTCATCTG CAAAGAGTCC     1080

TGCAATGAGG ATGTCATTGG GGCCCTGCTC AATGTGTTTG TTTGGATCGG TTATCTCTCT     1140

TCAGCAGTCA ACCCACTAGT CTATACTCTG TTCAACAAAA TTTACCGAAG GCATTCTCC      1200

AACTATTTGC GTTGCAATTA TAAGGTAGAG AAAAAGCCTC CTGTCAGGCA GATTCCAAGA     1260

GTTGCCGCCA CTGCTTTGTC TGGGAGGGAG CTTAATGTTA ACATTTATCG GCATACCAAT     1320

GAACCGGTGA TCGAGAAAGC CAGTGACAAT GAGCCCGGTA TAGAGATGCA AGTTGAGAAT     1380

TTAGAGTTAC CAGTAAATCC CTCCAGTGTG GTTAGCGAAA GGATTAGCAG TGTGTGA       1437
```

(2) INFORMATION FOR SEQ ID NO:25:

(i) SEQUENCE CHARACTERISTICS:
        (A) LENGTH: 478 amino acids
        (B) TYPE: amino acid
        (C) STRANDEDNESS:
        (D) TOPOLOGY: Not Relevant (ii) MOLECULE TYPE: protein (xi) SEQUENCE DESCRIPTION: SEQ ID NO:25:

```
Met Asp Ile Leu Cys Glu Glu Asn Thr Ser Leu Ser Ser Thr Thr Asn
1               5                   10                  15

Ser Leu Met Gln Leu Asn Asp Asp Asn Arg Leu Tyr Ser Asn Asp Phe
            20                  25                  30

Asn Ser Gly Glu Ala Asn Thr Ser Asp Ala Phe Asn Trp Thr Val Asp
        35                  40                  45

Ser Glu Asn Arg Thr Asn Leu Ser Cys Glu Gly Cys Leu Ser Pro Ser
    50                  55                  60

Cys Leu Ser Leu Leu His Leu Gln Glu Lys Asn Trp Ser Ala Leu Leu
65                  70                  75                  80

Thr Ala Val Val Ile Ile Leu Thr Ile Ala Gly Asn Ile Leu Val Ile
                85                  90                  95

Met Ala Val Ser Leu Glu Lys Lys Leu Gln Asn Ala Thr Asn Tyr Phe
            100                 105                 110

Leu Met Ser Leu Ala Ile Ala Asp Met Leu Leu Gly Phe Leu Val Met
        115                 120                 125

Pro Val Ser Met Leu Thr Ile Leu Tyr Gly Tyr Arg Trp Pro Leu Pro
    130                 135                 140

Ser Lys Leu Cys Ala Val Trp Ile Tyr Leu Asp Val Leu Phe Ser Thr
145                 150                 155                 160

Ala Ser Ile Met His Leu Cys Ala Ile Ser Leu Asp Arg Tyr Val Ala
                165                 170                 175

Ile Gln Asn Pro Ile His His Ser Arg Phe Asn Ser Arg Thr Lys Ala
            180                 185                 190
```

```
Phe Leu Lys Ile Ile Ala Val Trp Thr Ile Ser Val Gly Ile Ser Met
            195                 200                 205

Pro Ile Pro Val Phe Gly Leu Gln Asp Asp Ser Lys Val Phe Lys Glu
    210                 215                 220

Gly Ser Cys Leu Leu Ala Asp Asp Asn Phe Val Leu Ile Gly Ser Phe
225                 230                 235                 240

Val Ser Phe Phe Ile Pro Leu Thr Ile Met Val Ile Thr Tyr Phe Leu
                245                 250                 255

Thr Ile Lys Val Leu Arg Arg Gln Ala Leu Met Leu Leu His Gly His
            260                 265                 270

Thr Glu Glu Pro Pro Gly Leu Ser Leu Asp Phe Leu Lys Cys Cys Lys
        275                 280                 285

Arg Asn Thr Ala Glu Glu Asn Ser Ala Asn Pro Asn Gln Asp Gln
    290                 295                 300

Asn Ala Arg Arg Arg Lys Lys Glu Arg Pro Arg Gly Thr Met
305                 310                 315                 320

Gln Ala Ile Asn Asn Glu Arg Lys Ala Ser Lys Val Leu Gly Ile Val
                325                 330                 335

Phe Phe Leu Phe Val Val Met Trp Cys Pro Phe Phe Ile Thr Asn Ile
            340                 345                 350

Met Ala Val Ile Cys Lys Glu Ser Cys Asn Glu Asp Val Ile Gly Ala
        355                 360                 365

Leu Leu Asn Val Phe Val Trp Ile Gly Tyr Leu Ser Ser Ala Val Asn
    370                 375                 380

Pro Leu Val Tyr Thr Leu Phe Asn Lys Ile Tyr Arg Arg Ala Phe Ser
385                 390                 395                 400

Asn Tyr Leu Arg Cys Asn Tyr Lys Val Glu Lys Lys Pro Pro Val Arg
                405                 410                 415

Gln Ile Pro Arg Val Ala Ala Thr Ala Leu Ser Gly Arg Glu Leu Asn
            420                 425                 430

Val Asn Ile Tyr Arg His Thr Asn Glu Pro Val Ile Glu Lys Ala Ser
        435                 440                 445

Asp Asn Glu Pro Gly Ile Glu Met Gln Val Glu Asn Leu Glu Leu Pro
    450                 455                 460

Val Asn Pro Ser Ser Val Val Ser Glu Arg Ile Ser Ser Val
465                 470                 475

(2) INFORMATION FOR SEQ ID NO:26:

(i) SEQUENCE CHARACTERISTICS:
        (A) LENGTH: 1437 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:26:

ATGGATATTC TTTGTGAAGA AAATACTTCT TGAGCTCAA CTACGAACTC CCTAATGCAA      60

TTAAATGATG ACAACAGGCT CTACAGTAAT GACTTTAACT CCGGAGAAGC TAACACTTCT    120

GATGCATTTA ACTGGACAGT CGACTCTGAA AATCGAACCA ACCTTTCCTG TGAAGGGTGC    180

CTCTCACCGT CGTGTCTCTC CTTACTTCAT CTCCAGGAAA AAAACTGGTC TGCTTTACTG    240

ACAGCCGTAG TGATTATTCT AACTATTGCT GGAAACATAC TCGTCATCAT GGCAGTGTCC    300

CTAGAGAAAA AGCTGCAGAA TGCCACCAAC TATTTCCTGA TGTCACTTGC CATAGCTGAT    360
```

-continued

```
ATGCTGCTGG GTTTCCTTGT CATGCCCGTG TCCATGTTAA CCATCCTGTA TGGGTACCGG    420

TGGCCTCTGC CGAGCAAGCT TTGTGCAGTC TGGATTTACC TGGACGTGCT CTTCTCCACG    480

GCCTCCATCA TGCACCTCTG CGCCATCTCG CTGGACCGCT ACGTCGCCAT CCAGAATCCC    540

ATCCACCACA GCCGCTTCAA CTCCAGAACT AAGGCATTTC TGAAAATCAT TGCTGTTTGG    600

ACCATATCAG TAGGTATATC CATGCCAATA CCAGTCTTTG GCTACAGGA CGATTCGAAG     660

GTCTTTAAGG AGGGGAGTTG CTTACTCGCC GATGATAACT TTGTCCTGAT CGGCTCTTTT    720

GTGTCATTTT TCATTCCCCT GACGATTATG GTGATTACGT ATTGCCTGAC CATCTACGTT    780

CTGCGCCGAC AAGCTTTGAT GTTACTGCAC GGCCACACCG AGGAACCGCC TGGACTAAGT    840

CTGGATTTCC TGAAGTGCTG CAAGAGGAAT ACGGCCGAGG AAGAGAACTC TGCAAACCCT    900

AACCAAGACC AGAACGCACG CCGAAGAAAG AAGAAGGAGA GACGTCCTAG GGGCACCATG    960

CAGGCTATCA CAATGAAAG AAAAGCTAAG AAAGTCCTTG GGATTGTTTT CTTTGTGTTT     1020

CTGATCATGT GGTGCCCTTT CTTCATCACA AACATCATGG CCGTCATCTG CAAAGAGTCC    1080

TGCAATGAGG ATGTCATTGG GGCCCTGCTC AATGTGTTTG TTTGGATCGG TTATCTCTCT    1140

TCAGCAGTCA ACCCACTAGT CTATACTCTG TTCAACAAAA TTTACCGAAG GCATTCTCC    1200

AACTATTTGC GTTGCAATTA TAAGGTAGAG AAAAAGCCTC CTGTCAGGCA GATTCCAAGA    1260

GTTGCCGCCA CTGCTTTGTC TGGGAGGGAG CTTAATGTTA ACATTTATCG GCATACCAAT    1320

GAACCGGTGA TCGAGAAAGC CAGTGACAAT GAGCCCGGTA TAGAGATGCA AGTTGAGAAT    1380

TTAGAGTTAC CAGTAAATCC CTCCAGTGTG GTTAGCGAAA GGATTAGCAG TGTGTGA      1437
```

(2) INFORMATION FOR SEQ ID NO:27:

(i) SEQUENCE CHARACTERISTICS:
        (A) LENGTH: 478 amino acids
        (B) TYPE: amino acid
        (C) STRANDEDNESS:
        (D) TOPOLOGY: Not Relevant (ii) MOLECULE TYPE: protein (xi) SEQUENCE DESCRIPTION: SEQ ID NO:27:

```
Met Asp Ile Leu Cys Glu Glu Asn Thr Ser Leu Ser Ser Thr Thr Asn
1               5                   10                  15

Ser Leu Met Gln Leu Asn Asp Asp Asn Arg Leu Tyr Ser Asn Asp Phe
            20                  25                  30

Asn Ser Gly Glu Ala Asn Thr Ser Asp Ala Phe Asn Trp Thr Val Asp
        35                  40                  45

Ser Glu Asn Arg Thr Asn Leu Ser Cys Glu Gly Cys Leu Ser Pro Ser
    50                  55                  60

Cys Leu Ser Leu Leu His Leu Gln Glu Lys Asn Trp Ser Ala Leu Leu
65                  70                  75                  80

Thr Ala Val Val Ile Ile Leu Thr Ile Ala Gly Asn Ile Leu Val Ile
                85                  90                  95

Met Ala Val Ser Leu Glu Lys Lys Leu Gln Asn Ala Thr Asn Tyr Phe
            100                 105                 110

Leu Met Ser Leu Ala Ile Ala Asp Met Leu Leu Gly Phe Leu Val Met
        115                 120                 125

Pro Val Ser Met Leu Thr Ile Leu Tyr Gly Tyr Arg Trp Pro Leu Pro
    130                 135                 140

Ser Lys Leu Cys Ala Val Trp Ile Tyr Leu Asp Val Leu Phe Ser Thr
145                 150                 155                 160
```

```
Ala Ser Ile Met His Leu Cys Ala Ile Ser Leu Asp Arg Tyr Val Ala
            165                 170                 175
Ile Gln Asn Pro Ile His His Ser Arg Phe Asn Ser Arg Thr Lys Ala
            180                 185                 190
Phe Leu Lys Ile Ile Ala Val Trp Thr Ile Ser Val Gly Ile Ser Met
            195                 200                 205
Pro Ile Pro Val Phe Gly Leu Gln Asp Asp Ser Lys Val Phe Lys Glu
            210                 215                 220
Gly Ser Cys Leu Leu Ala Asp Asp Asn Phe Val Leu Ile Gly Ser Phe
225                 230                 235                 240
Val Ser Phe Phe Ile Pro Leu Thr Ile Met Val Ile Thr Tyr Cys Leu
            245                 250                 255
Thr Ile Tyr Val Leu Arg Arg Gln Ala Leu Met Leu Leu His Gly His
            260                 265                 270
Thr Glu Glu Pro Pro Gly Leu Ser Leu Asp Phe Leu Lys Cys Cys Lys
            275                 280                 285
Arg Asn Thr Ala Glu Glu Asn Ser Ala Asn Pro Asn Gln Asp Gln
            290                 295                 300
Asn Ala Arg Arg Arg Lys Lys Lys Glu Arg Arg Pro Arg Gly Thr Met
305                 310                 315                 320
Gln Ala Ile Asn Asn Glu Arg Lys Ala Lys Lys Val Leu Gly Ile Val
            325                 330                 335
Phe Phe Val Phe Leu Ile Met Trp Cys Pro Phe Phe Ile Thr Asn Ile
            340                 345                 350
Met Ala Val Ile Cys Lys Glu Ser Cys Asn Glu Asp Val Ile Gly Ala
            355                 360                 365
Leu Leu Asn Val Phe Val Trp Ile Gly Tyr Leu Ser Ser Ala Val Asn
            370                 375                 380
Pro Leu Val Tyr Thr Leu Phe Asn Lys Ile Tyr Arg Arg Ala Phe Ser
385                 390                 395                 400
Asn Tyr Leu Arg Cys Asn Tyr Lys Val Glu Lys Lys Pro Pro Val Arg
            405                 410                 415
Gln Ile Pro Arg Val Ala Ala Thr Ala Leu Ser Gly Arg Glu Leu Asn
            420                 425                 430
Val Asn Ile Tyr Arg His Thr Asn Glu Pro Val Ile Glu Lys Ala Ser
            435                 440                 445
Asp Asn Glu Pro Gly Ile Glu Met Gln Val Glu Asn Leu Glu Leu Pro
            450                 455                 460
Val Asn Pro Ser Ser Val Val Ser Glu Arg Ile Ser Ser Val
465                 470                 475
```